US010076291B2

(12) United States Patent
Arai et al.

(10) Patent No.: US 10,076,291 B2
(45) Date of Patent: Sep. 18, 2018

(54) X-RAY CT IMAGING DEVICE

(71) Applicants: Nihon University, Tokyo (JP); J. Morita Manufacturing Corporation, Kyoto (JP)

(72) Inventors: Yoshinori Arai, Tokyo (JP); Makoto Honjo, Kyoto (JP); Masakazu Suzuki, Kyoto (JP); Susumu Kirimura, Kyoto (JP); Hideki Yoshikawa, Kyoto (JP)

(73) Assignees: Nihon University, Tokyo (JP); J. Morita Manufacturing Corporation, Kyoto (JP)

( * ) Notice: Subject to any disclaimer, the term of this patent is extended or adjusted under 35 U.S.C. 154(b) by 528 days.

(21) Appl. No.: 13/691,158

(22) Filed: Nov. 30, 2012

(65) Prior Publication Data

US 2013/0170610 A1    Jul. 4, 2013

(30) Foreign Application Priority Data

Nov. 30, 2011  (JP) ................................. 2011-262267

(51) Int. Cl.
  *A61B 6/14*   (2006.01)
  *A61B 6/06*   (2006.01)
  *A61B 6/00*   (2006.01)

(52) U.S. Cl.
  CPC .................. *A61B 6/14* (2013.01); *A61B 6/06* (2013.01); *A61B 6/4441* (2013.01); *A61B 6/501* (2013.01); *A61B 6/542* (2013.01); *A61B 6/405* (2013.01)

(58) Field of Classification Search
  CPC .. A61B 6/06; A61B 6/14; A61B 6/441; A61B 6/501; A61B 6/542; A61B 6/405
  (Continued)

(56) References Cited

U.S. PATENT DOCUMENTS

2008/0310584 A1    12/2008  Hey et al.
2009/0196395 A1     8/2009  Gregorio et al.
(Continued)

FOREIGN PATENT DOCUMENTS

DE    10 2005 004 502 A1    8/2006
EP         1 444 952 A1     8/2004
(Continued)

OTHER PUBLICATIONS

Zhang B. et al., "Two-dimensional iterative region-of-interest (ROI) reconstruction from truncated projection data," Medical Physics, vol. 34, No. 3; p. 935-944, Mar. 2007 (10 pages).

*Primary Examiner* — Eliza Osenbaugh-Stewart
(74) *Attorney, Agent, or Firm* — Osha Liang LLP

(57) ABSTRACT

The present invention has an object of providing an X-ray CT imaging device which can direct X-ray to an area of interest appropriately even when, for example, the height of the area of interest with respect to the X-ray detector, which is revolving, varies with respect to the revolution direction, and thus can reduce the amount of unnecessary exposure to the X-ray and can perform X-ray imaging of the area of interest with certainty. In an X-ray CT imaging device for performing X-ray CT imaging of a CT imaging area of a subject, during the X-ray CT imaging when a revolving arm is revolving, the expansion in a length direction of an X-ray cone beam, which is to be restricted by length direction blocking plates, is adapted to the shape of the CT imaging area in accordance with the revolution position of the revolving arm.

14 Claims, 35 Drawing Sheets

(58) Field of Classification Search
USPC .......................... 378/4–20, 38–39, 150–153
See application file for complete search history.

(56) References Cited

U.S. PATENT DOCUMENTS

| | | |
|---|---|---|
| 2010/0246752 A1* | 9/2010 | Heuscher et al. ................. 378/4 |
| 2011/0013742 A1* | 1/2011 | Zaiki et al. ...................... 378/15 |
| 2011/0064188 A1* | 3/2011 | Suzuki et al. ................... 378/21 |
| 2014/0177782 A1* | 6/2014 | Herold .............................. 378/4 |

FOREIGN PATENT DOCUMENTS

| | | |
|---|---|---|
| EP | 2 286 728 A1 | 2/2011 |
| JP | H09-122118 A | 5/1997 |
| JP | 3378401 B2 | 2/2003 |
| JP | 2004-208799 A | 7/2004 |
| JP | 2007-029168 A | 2/2007 |
| JP | 2011-041598 A | 3/2011 |

* cited by examiner

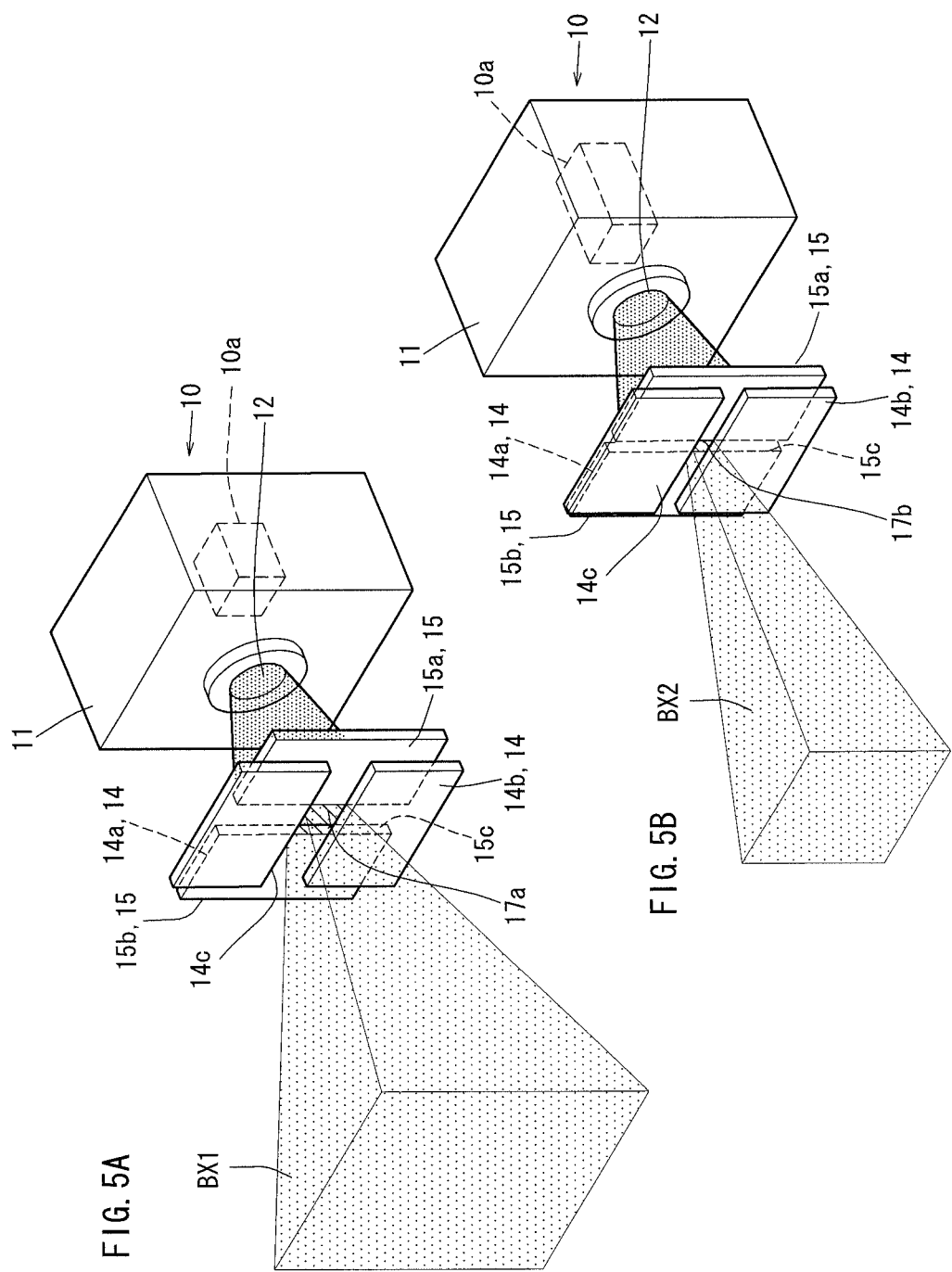

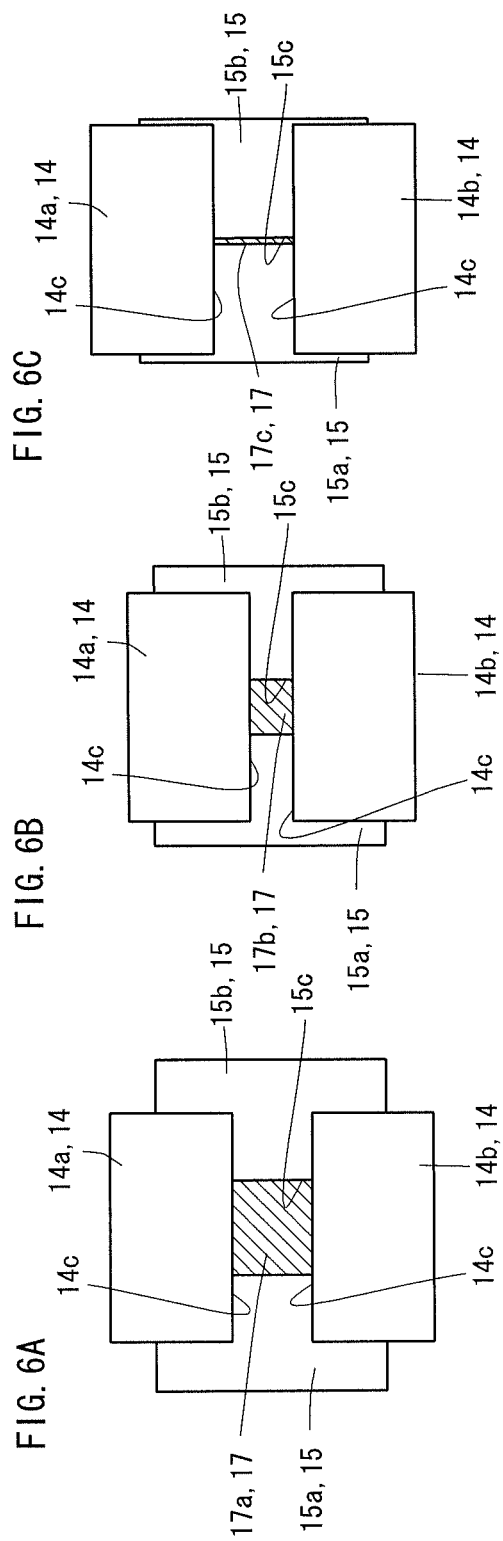

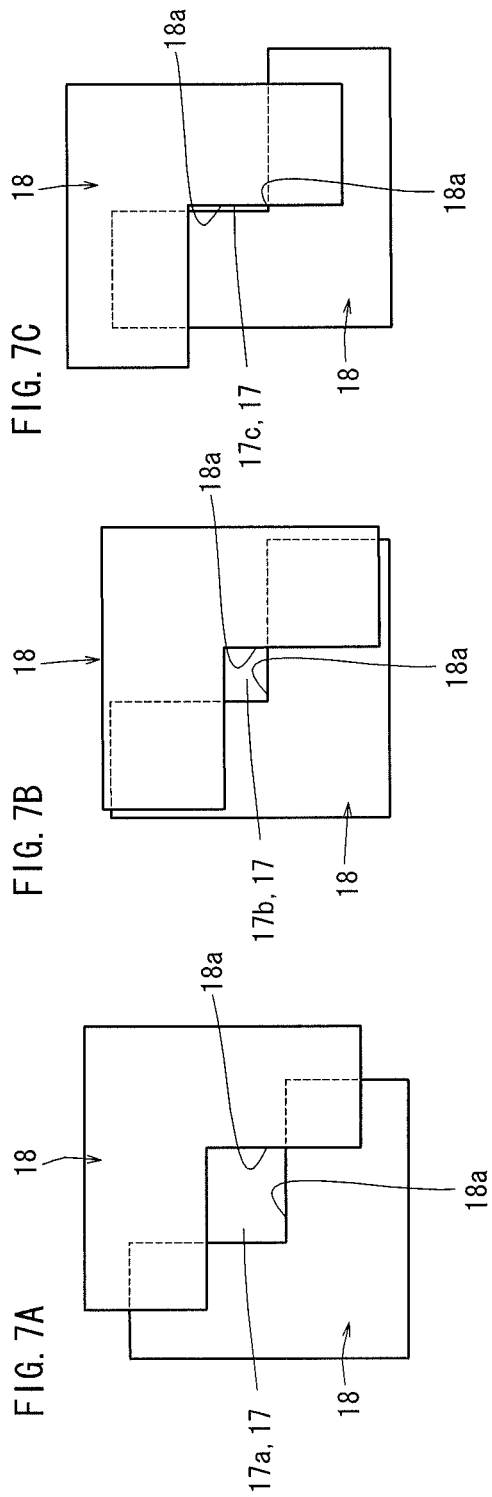

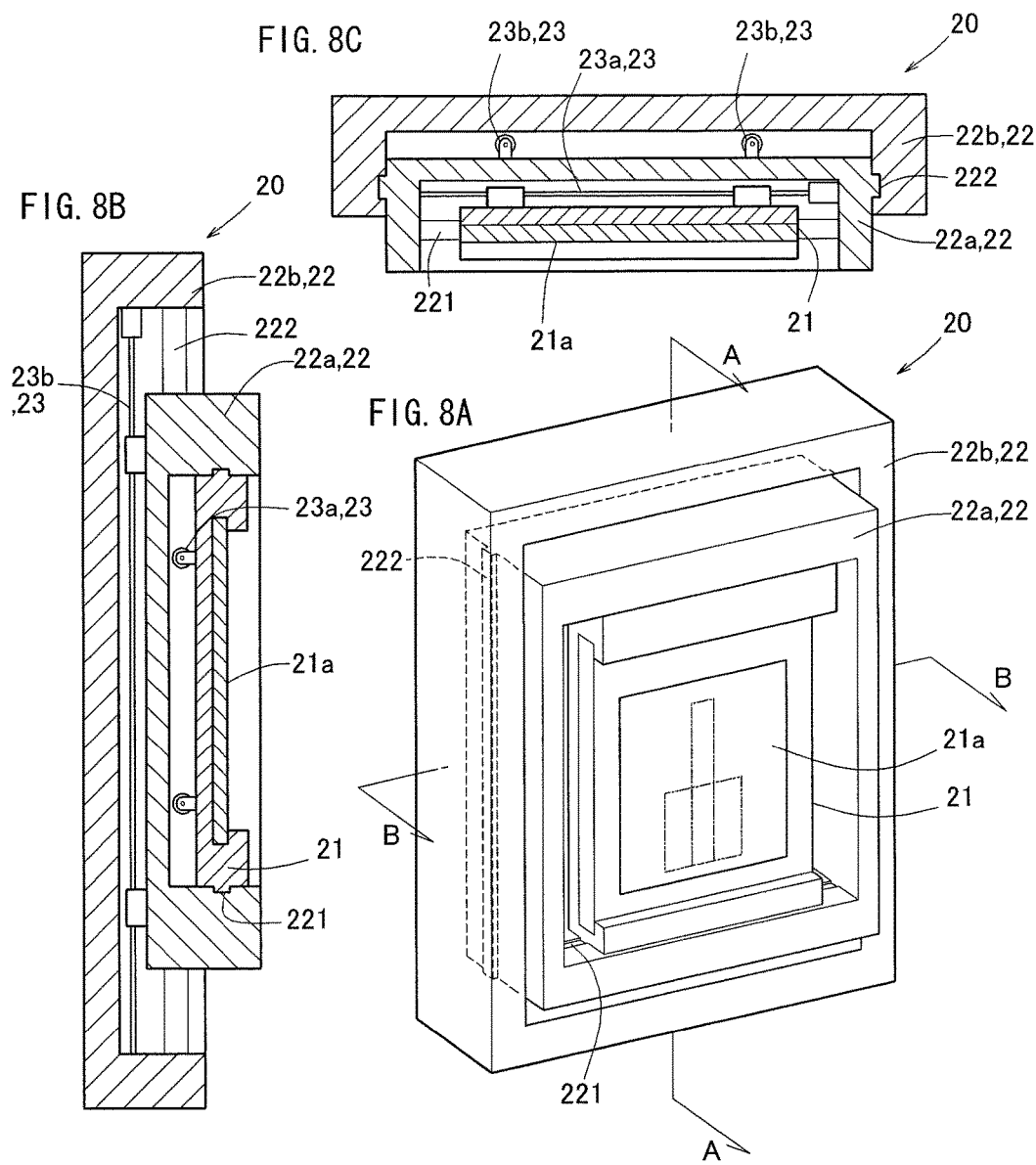

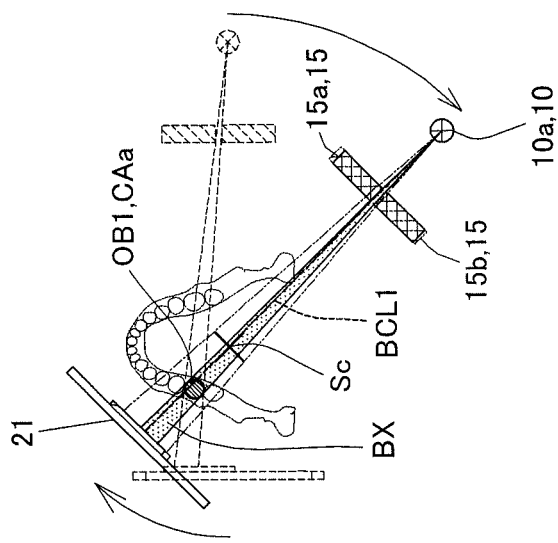
FIG. 9B SECOND REVOLUTION POSITION
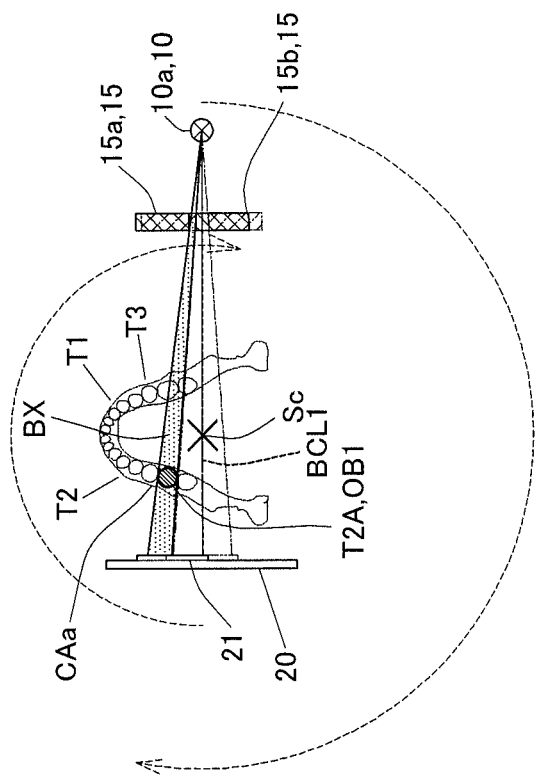
FIG. 9A FIRST REVOLUTION POSITION

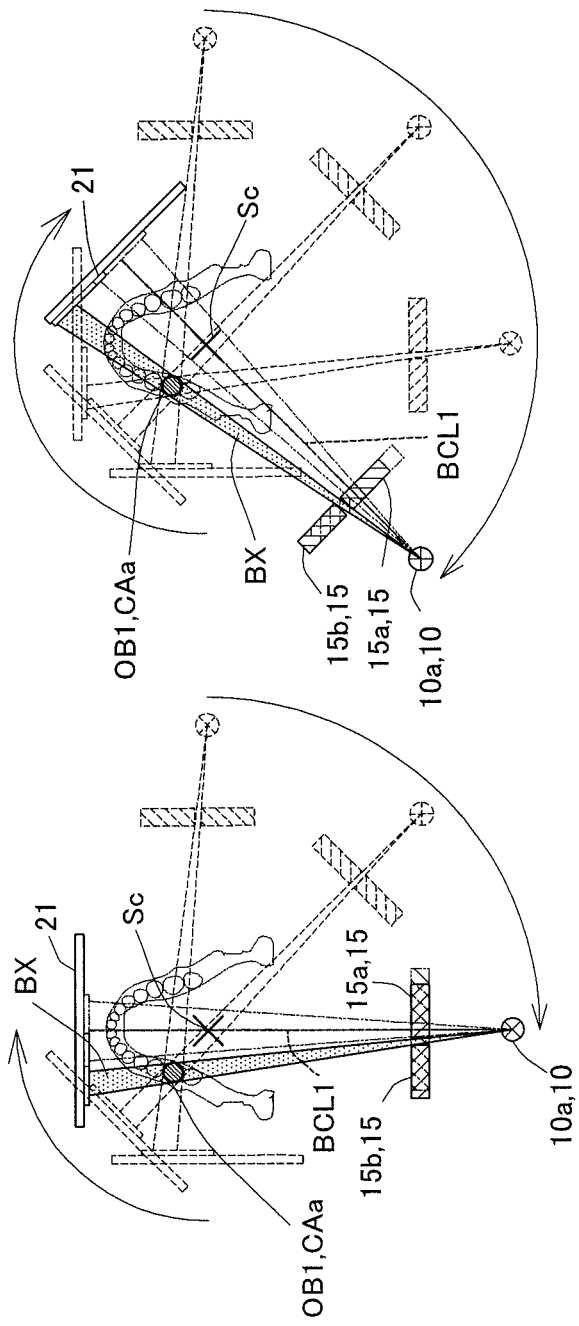

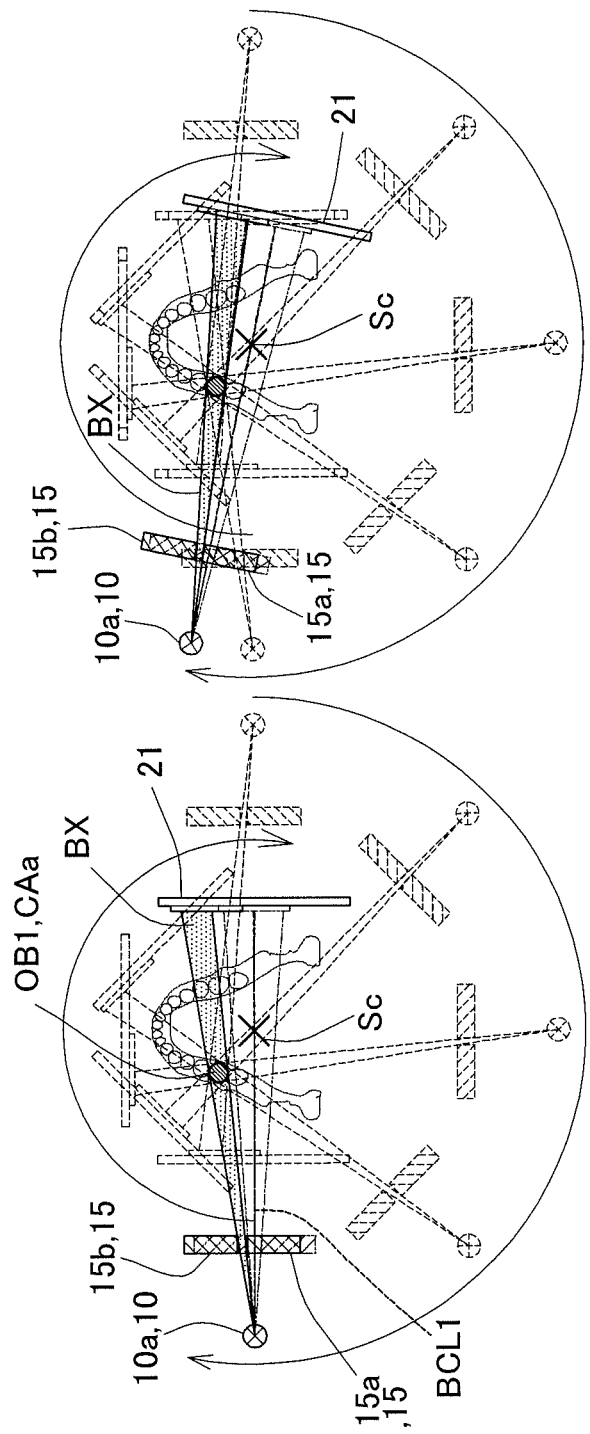

FIRST REVOLUTION
POSITION

SECOND REVOLUTION
POSITION

THIRD REVOLUTION
POSITION

FOURTH REVOLUTION
POSITION

FIFTH REVOLUTION
POSITION

SIXTH REVOLUTION POSITION

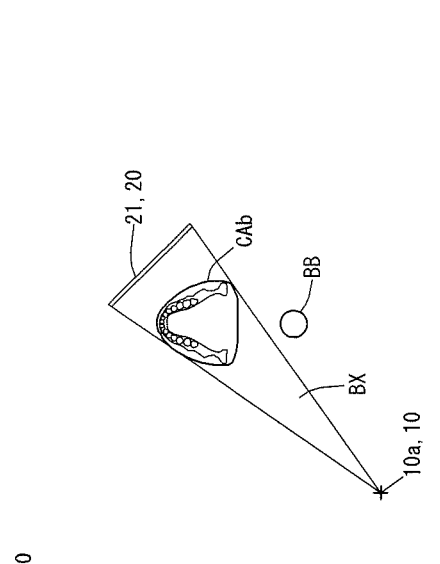
FIG. 23A
FIRST REVOLUTION POSITION
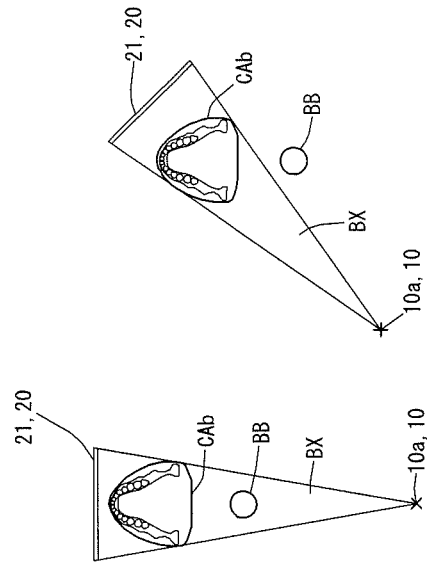
FIG. 23B
SECOND REVOLUTION POSITION
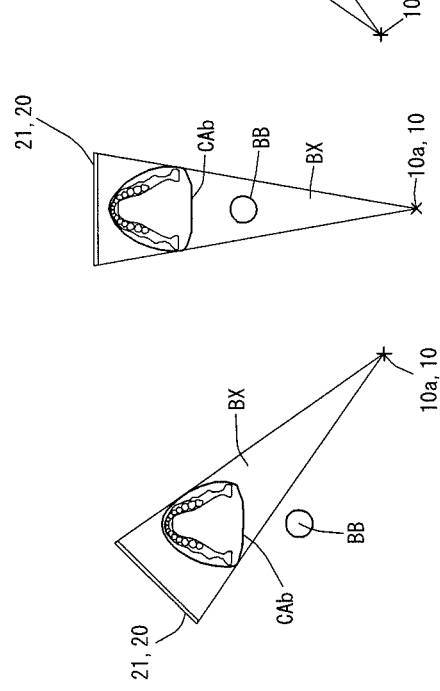
FIG. 23C
THIRD REVOLUTION POSITION
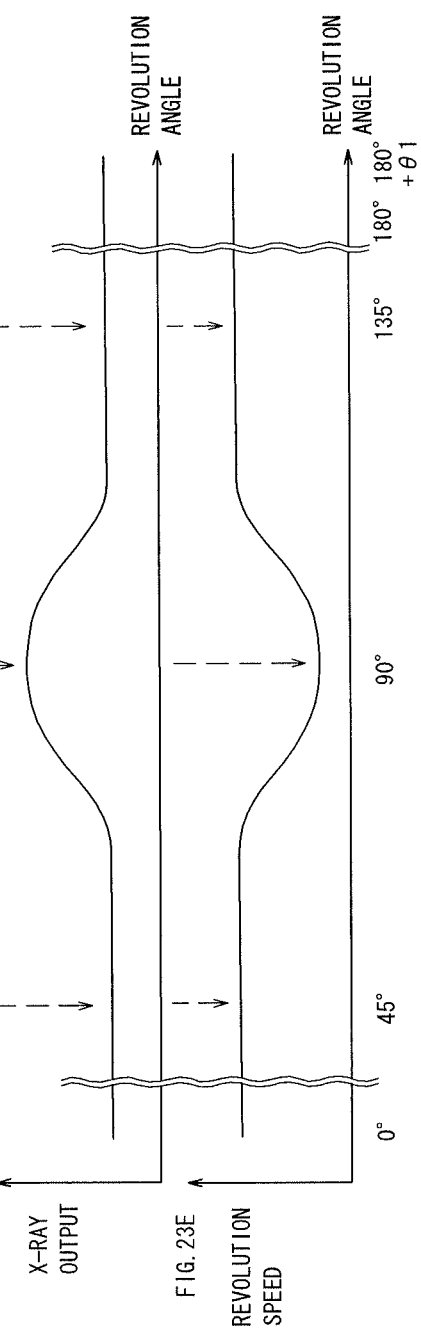
FIG. 23D X-RAY OUTPUT
FIG. 23E REVOLUTION SPEED

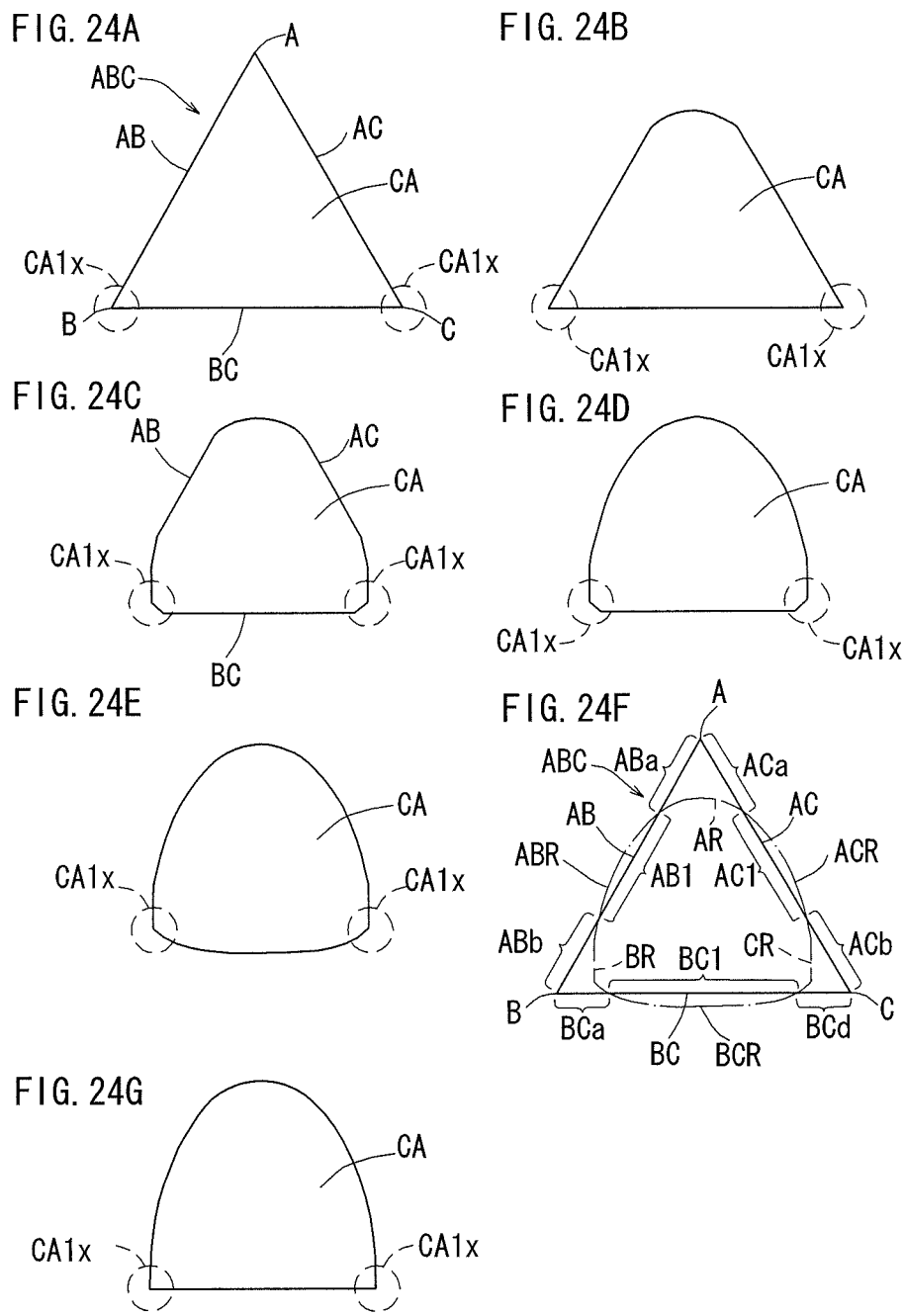

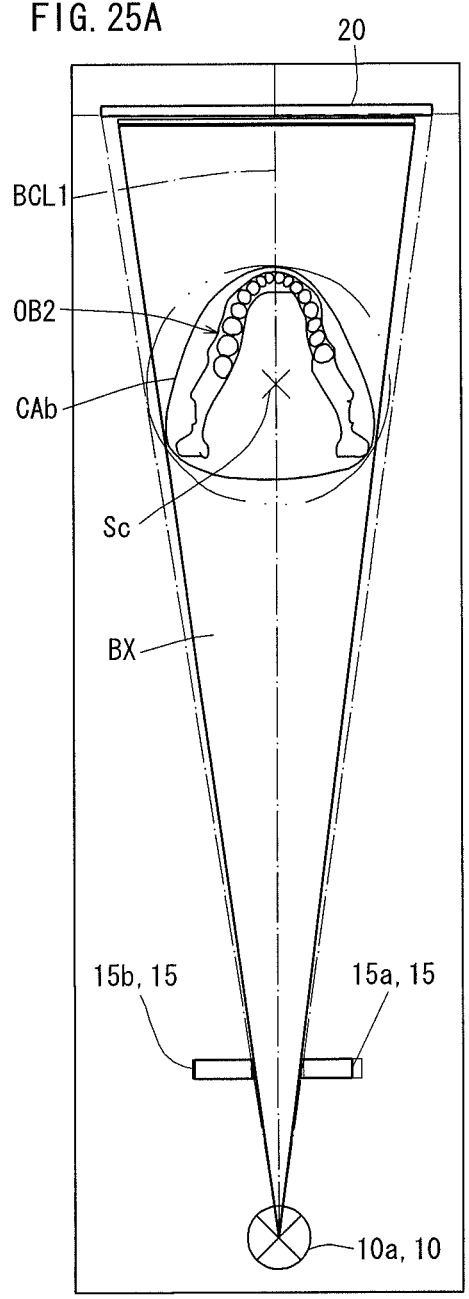
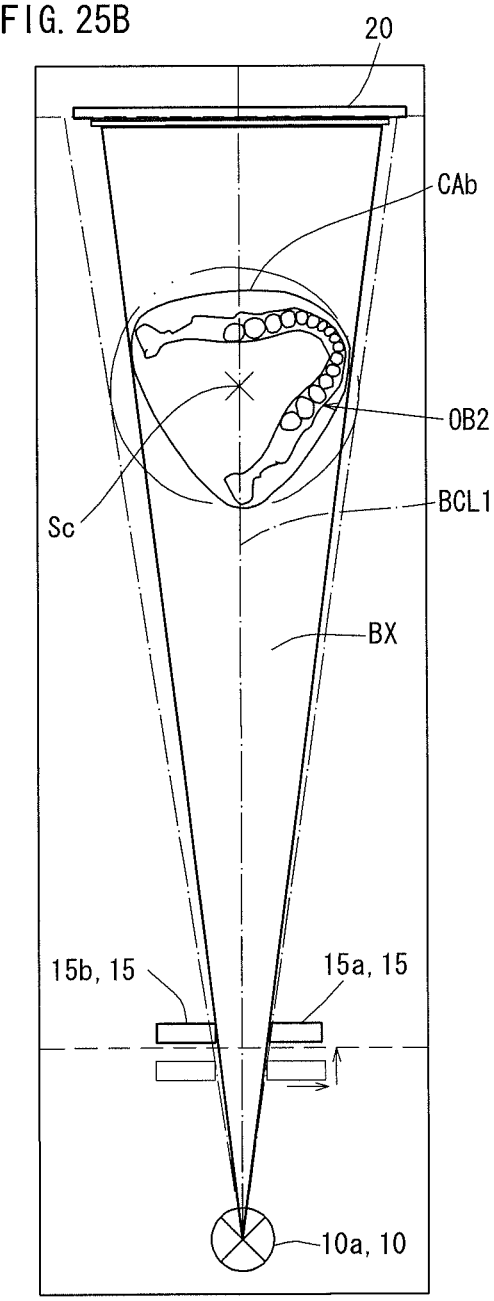
FIG. 25A
FIG. 25B

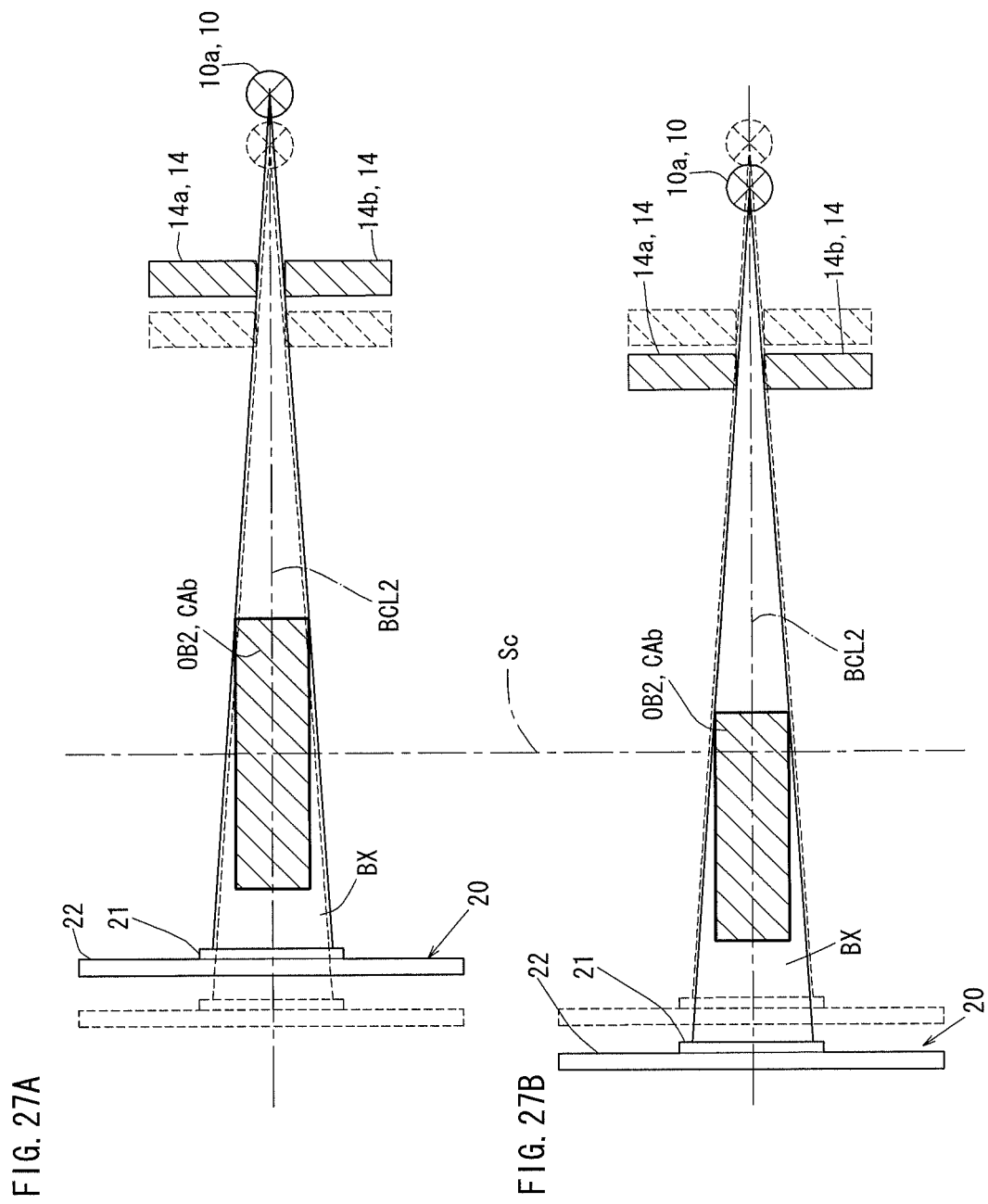

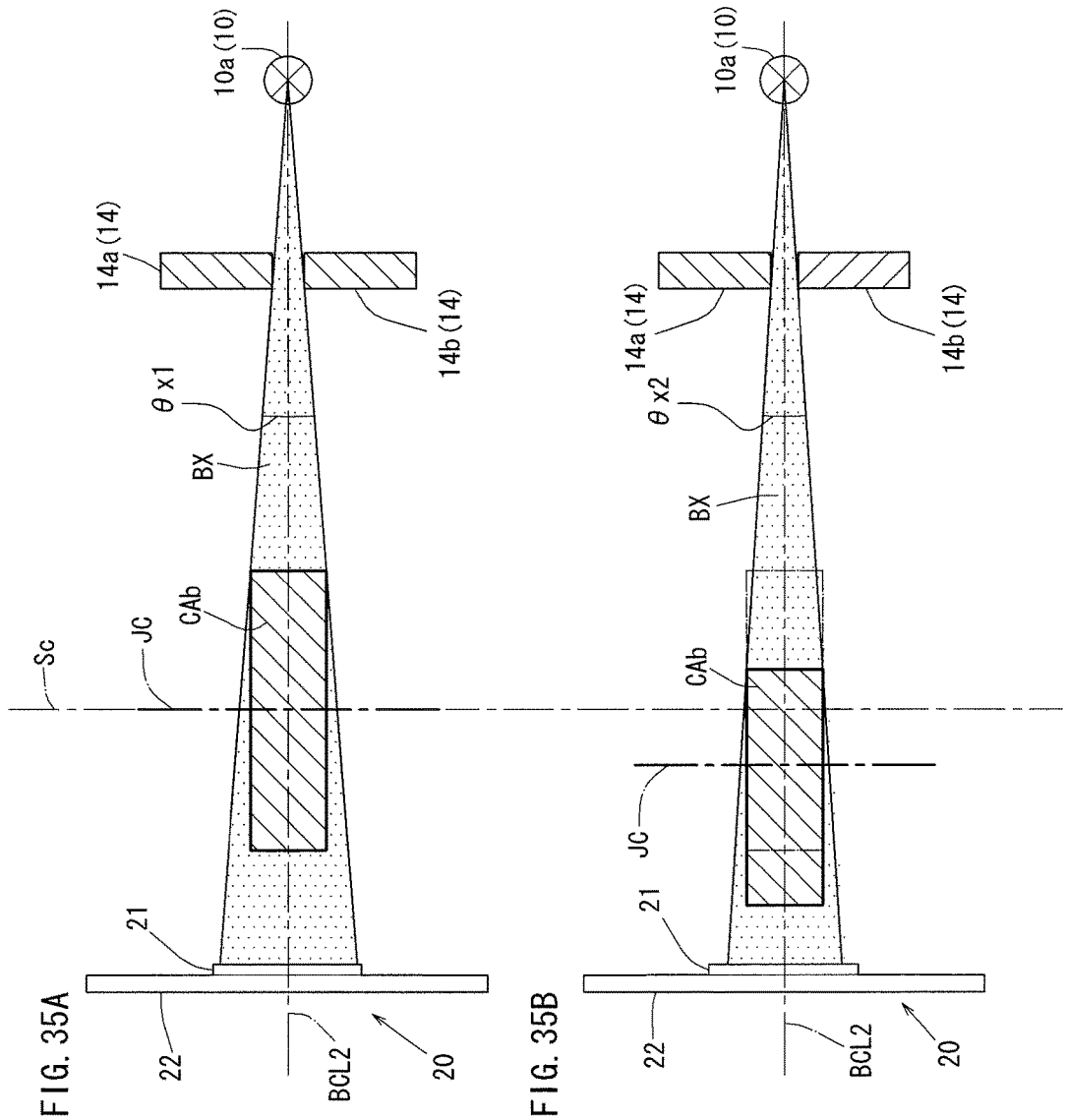

X-RAY CT IMAGING DEVICE

BACKGROUND OF THE INVENTION

1. Field of the Invention

The present invention relates an X-ray CT imaging device for, for example, detecting X-ray output from an X-ray generator by use of an X-ray detector and thus performing X-ray CT imaging of a subject which is located between the X-ray generator and the X-ray detector.

2. Description of the Prior Art

Conventionally in the field of medicine and the like, X-ray CT imaging is performed. According to the X-ray CT imaging, a subject is irradiated with X-ray to collect projection data, and the obtained projection data is reconstructed on, a computer to generate a computerized tomography image (computed tomography (CT) image, volume rendering image, etc.).

Such X-ray imaging is performed as follows. In the state where a subject is located between an X-ray generator and an X-ray detector, a cone-like X-ray beam (X-ray cone beam) is directed from the X-ray generator to the subject while the X-ray generator and the X-rat detector are revolved around the subject. X-ray detection results (projection data) are collected by the X-ray detector, and three-dimensional data is reconstructed based on the collected X-ray detection results (projection data). An example of device for performing such X-ray CT imaging is disclosed in, for example, Patent Document 1.

Patent Document 1 describes that the X-ray imaging device described therein can perform CT imaging of a wider area with a smaller X-ray detection plane by offset scanning. According to the offset scanning, the position to which the X-ray cone beam is directed is offset from the center of the subject, so that a part of the subject is always irradiated with the X-ray cone beam during the imaging.

However, the X-ray imaging device described in Patent Document 1 has the following undesirable possibility. The X-ray expands in a length direction, which is a direction of the axis of revolution, in a uniform manner. Therefore, an area of the subject which is not an area of interest is irradiated with the X-ray to unnecessarily increase the amount of exposure, or the area of interest cannot be irradiated with the X-ray.

PRIOR ART DOCUMENT

Patent Document

Patent Document 1: Japanese Patent No. 3378401

SUMMARY OF THE INVENTION

Problems to be Solved by the Invention

Thus, the present invention has an object of providing an X-ray CT imaging device for directing an X-ray cone beam to an area of interest appropriately to decrease the amount of unnecessary exposure while performing X-ray CT imaging of the area of interest with certainty.

Solutions for the Problems

The present invention is directed to an X-ray CT imaging device for performing X-ray CT imaging of a CT imaging area of a subject. The X-ray CT imaging device includes an imaging mechanism including an X-ray generator for generating X-ray, an X-ray restriction section for blocking and restricting a radiation range of the X-ray generated by the X-ray generator to form an X-ray cone beam to be directed to the CT imaging area, and an X-ray detector for detecting the X-ray cone beam directed to the subject; a support for supporting the X-ray generator and the X-ray detector in the state where the X-ray generator and the X-ray detector have the subject therebetween; an imaging mechanism driving section for revolving the support at least about an axis of a revolution shaft with respect to the subject; and a control section for controlling at least the X-ray generator, the X-ray restriction section and the imaging mechanism driving section. A direction parallel to a direction of the axis of the revolution shaft is a length direction. The X-ray restriction section includes a length direction X-ray blocking section for blocking and restricting the radiation range of the X-ray cone beam in the length direction with respect to the CT imaging area; and a length direction adjusting section for, during the X-ray CT imaging when the support is revolving, adapting an expansion in the length direction of the X-ray cone beam, which is to be restricted by the length direction X-ray blocking section, to a shape of the CT imaging area in accordance with a revolution position of the imaging mechanism driven by the imaging mechanism driving section, the length direction adjusting section being controllable by the control section.

The "imaging mechanism driving section for revolving the support at least about the axis of the revolution shaft with respect to the subject" represents a concept encompassing a driving section in which the revolution shaft is fixed and only the revolution driving is possible, and a driving section capable of relatively moving the revolution shaft with respect to the subject in addition to performing the revolution driving.

The length direction X-ray blocking section for blocking and restricting the radiation range of the X-ray cone beam in the length direction with respect to the CT imaging area blocks at least one of a top part and a bottom part in the length direction of the radiation range of the X-ray generated by the X-ray generator, and blocks the radiation range only in the length direction or in the lateral direction and the length direction.

The expression "during the X-ray CT imaging when the support is revolving" represents a concept encompassing the entirety of a series of operations in the X-ray CT imaging; specifically, encompassing the instant when the X-ray cone beam directed from the X-ray generator of the imaging mechanism is detected by the X-ray detector and also the time duration in which the processing of the imaging mechanism is at a pause and the imaging mechanism driving section revolves the support.

The length direction adjusting section for adapting the expansion in the length direction of the X-ray cone beam, which is to be restricted by the length direction X-ray blocking section, to the shape of the CT imaging area in accordance with the revolution position of the imaging mechanism driven by the imaging mechanism driving section may be a section for moving the length direction X-ray blocking section in at least the length direction with respect to the X-ray generator, a section for adjusting the distance from the length direction X-ray blocking section to the X-ray generator, or a section for adjusting the distance from the imaging mechanism to the subject, or a combination thereof.

According to the present invention, the X-ray can be directed to the area of interest appropriately. Thus, the amount of unnecessary exposure to the X-ray can be decreased, and the X-ray CT imaging of the area of interest can be performed with certainty.

This will be described in more detail. For example, in the case where the X-ray CT imaging is performed with a constant expansion in the length direction of the X-ray cone beam on an area of interest in which the height (length in the length direction) in the axial direction of the revolution shaft, which is revolving, varies in accordance with the revolution direction, the following occurs. When the CT imaging area by the X-ray cone beam is larger than the area of interest, an area other than the area of interest may be undesirably irradiated with the X-ray, and thus the amount of exposure to the X-ray may be unnecessarily increased. By contrast, when the CT imaging area by the X-ray cone beam is smaller than the area of interest, the area of interest may not be irradiated with the X-ray.

In order to avoid this, the length direction adjusting section is controlled by the control section such that the expansion in the length direction of the X-ray cone beam, which is to be restricted by the length direction X-ray blocking section, is adapted to the shape of the CT imaging area having an appropriate height in the length direction for the area of interest, in accordance with the revolution position of the imaging mechanism driven by the imaging mechanism driving section. Thus, the amount of unnecessary exposure to the X-ray can be decreased, and the X-ray CT imaging of the area of interest can be performed with certainty.

In an embodiment of the present invention, the length direction adjusting section may include a blocking section length direction moving section for moving the length direction X-ray blocking section in the length direction.

According to the present invention, the expansion in the length direction of the X-ray cone beam can be blocked and restricted with a simple structure and can be adapted to the shape of the CT imaging area having an appropriate height in the length direction for the area of interest.

In an embodiment of the present invention, the length direction X-ray blocking section may include a plurality of length direction blocking members independently movable in the length direction with respect to the CT imaging area; and the blocking section length direction moving section may be structured to move the length direction blocking members.

According to the present invention, the expansion in the length direction of the X-ray cone beam can be blocked and restricted, and the radiation direction of the X-ray cone beam in the length direction can be adjusted with respect to the X-ray generator.

This will be described in more detail. The plurality of length direction blocking members movable independently in the length direction with respect to the CT imaging area are shifted in the length direction from the length-direction center of the X-ray cone beam which is output from the X-ray generator. Thus, the radiation direction of the X-ray cone beam can be adjusted in the length direction with respect to the X-ray generator. Therefore, even when the area of interest is a local area such as a part of the upper jaw or the lower jaw and such a local area of interest is eccentric in the length direction with respect to the radiation direction from the X-ray generator, the shape of the CT imaging area can be adapted to the area of interest with certainty.

In an embodiment of the present invention, the imaging mechanism driving section may include a revolution shaft moving mechanism for relatively moving the revolution shaft with respect to the subject; and the length direction adjusting section may include the revolution shaft moving mechanism for adjusting a distance from the X-ray generator to the subject.

According to the present invention, the expansion in the length direction of the X-ray cone beam can be adapted to the shape of the CT imaging area having an appropriate height in the length direction for the area of interest.

In an embodiment of the present invention, the control section may be structured to control the expansion in the length direction of the X-ray cone beam to become larger when the X-ray generator approaches the CT imaging area and to become smaller when the X-ray generator is distanced from the CT imaging area.

According to the present invention, even when the length direction adjusting section includes the blocking section length direction moving section for moving the length direction X-ray blocking section in the length direction or the revolution shaft moving mechanism for adjusting the distance from the X-ray generator to the subject, the shape of the CT imaging area can be adapted to the area of interest with certainty. Thus, the amount of unnecessary exposure to the X-ray can be decreased, and the X-ray CT imaging of the area of interest can be performed with certainty.

In an embodiment of the present invention, the X-ray CT imaging device may include an X-ray detector moving section for relatively moving the X-ray detector with respect to the support. The control section may be structured to control the X-ray detector moving section in accordance with the radiation range of the X-ray cone beam.

According to the present invention, the X-ray detector can be made compact. This will be described in more detail. The expansion in the length direction of the X-ray cone beam is adjusted by the length direction adjusting section. Therefore, after the range of the X-ray detected by the X-ray detection section is adjusted, the expansion in the length direction of the X-ray cone beam is made different. Especially when the radiation range of the X-ray cone beam in the length direction is adjusted, the center of the detection range is moved.

In order to avoid this, the X-ray detector moving section for relatively moving the X-ray detector with respect to the support is provided, and is controlled by the control section in accordance with the radiation range of the X-ray cone beam. Owing to this, the X-ray detector can follow the detection range which is made different or moved, and thus a maximum possible projection range can be covered by the X-ray detector even when the X-ray detector is compact. Accordingly, the X-ray detector can be made compact as compared with the case where the size of the X-ray detector is adapted to the maximum possible projection range. Thus, the cost of the X-ray detector, which requires a highly expensive detection sensor, can be reduced.

In an embodiment of the present invention, a direction which is perpendicular to a direction from the X-ray generator to the X-ray detector and also perpendicular to the length direction is a lateral direction. The X-ray restriction section may includes a lateral direction X-ray blocking section for blocking and restricting the radiation range of the X-ray cone beam in the lateral direction with respect to the CT imaging area; and a lateral direction adjusting section for, during the X-ray CT imaging when the support is revolving, adapting the expansion in the lateral direction of the X-ray cone beam, which is to be restricted by the lateral direction X-ray blocking section, to the shape of the CT imaging area in accordance with the revolution position of the imaging mechanism driven by the imaging mechanism driving section.

According to the present invention, the X-ray can be directed to the area of interest appropriately, and the CT imaging area having a desired planar shape in accordance with the shape of the area of interest can be formed. Thus, the amount of unnecessary exposure to the X-ray can be decreased.

This will be described in more detail. During the X-ray CT imaging when the support is revolving, the lateral direction adjusting section adapts the expansion in the lateral direction of the X-ray cone beam, which is to be restricted by the lateral direction X-ray blocking section, to the shape of the CT imaging area in accordance with the revolving position of the imaging mechanism driven by the imaging mechanism driving section. Owing to this, even when the diameter of the area of interest varies with respect to the revolution shaft in accordance with the revolution direction as seen in a plan view, or even when the area of interest is eccentric with respect to the revolution shaft as seen in a plan view, the CT imaging area having a desired planar shape in accordance with the shape of the area of interest can be formed. Thus, the amount of unnecessary exposure to the X-ray can be decreased.

In an embodiment of the present invention, the lateral direction X-ray blocking section may include a plurality of lateral direction blocking members independently movable in the lateral direction with respect to the CT imaging area; and the lateral direction adjusting section may include a blocking section lateral direction moving section for moving the lateral direction blocking members.

According to the present invention, the expansion in the lateral direction of the X-ray cone beam can be blocked and restricted, and the radiation direction of the X-ray cone beam in the lateral direction can be adjusted with respect to the X-ray generator.

This will be described in more detail. The plurality of lateral direction blocking members movable independently in the lateral direction with respect to the CT imaging area are shifted in the lateral direction from the lateral-direction center of the X-ray cone beam which is output from the X-ray generator. Thus, the radiation direction of the X-ray cone beam can be adjusted in the lateral direction with respect to the X-ray generator. Therefore, even when the area of interest is shifted in the lateral direction with respect to the revolution shaft, the shape of the CT imaging area can be adapted to the area of interest with certainty.

In an embodiment of the present invention, the control section may be structured to control at least the lateral direction X-ray blocking section in accordance with revolution driven by the imaging mechanism driving section, such that the CT imaging area has a generally triangular shape as seen in a plan view.

According to the present invention, the lateral direction X-ray blocking section is controlled, so that the shape of the CT imaging area is made generally triangular in accordance with the shape of the area of interest. Thus, the amount of unnecessary exposure to the X-ray can be decreased, and the detection plane section can be made small.

In an embodiment of the present invention, the CT imaging area formed to have the generally triangular shape as seen in a plan view may be set to accommodate anterior teeth and left and right posterior teeth of a dental arch.

According to the present invention, the anterior teeth and left and right posterior teeth of the dental arch are accommodated in the CT imaging area. Therefore, the X-ray CT imaging can be performed with certainty on a site which needs to be imaged.

In an embodiment of the present invention, in the generally triangular shape as seen in a plan view, at least one of three corners may be formed of an arc convexed outward and thus is rounded.

The shape in which "at least one of three corners is formed of an arc convexed outward and thus is rounded" may be a shape of an isosceles triangle in which the apex facing the base side is formed of an arc convexed outward and thus is rounded, or a shape of the isosceles triangle in which corners at both of two ends of the base side are each formed of an arc convexed outward and thus is rounded.

According to the present invention, even when the area of interest includes a generally semicircular (encompassing generally semi-elliptical) imaging target, the shape of the CT imaging area can be adapted to the shape of the area of interest. Thus, the amount of unnecessary exposure to the X-ray can be decreased.

In an embodiment of the present invention, in the generally triangular shape as seen in a plan view, at least one of three sides may include an arc convexed outward at a central part thereof.

The shape in which "at least one of three sides includes an arc convexed outward at a central part thereof" may be a shape of the isosceles triangle in which two sides other than the base side each include an arc convexed outward at a central part thereof, or a shape of the isosceles triangle in which either one of the three sides includes an arc convexed outward at a central part thereof.

According to the present invention, even when the area of interest includes a generally semicircular imaging target, the shape of the CT imaging area can be adapted to the shape of the area of interest with higher precision. Thus, the amount of unnecessary exposure to the X-ray can be further decreased.

In an embodiment of the present invention, in the generally triangular shape as seen in a plan view, one of three sides may have outward protrusions at both of two ends thereof, and an apex facing the one side and each of the protrusions are connected to each other by a curved line; and the generally triangular shape may be bilaterally symmetrical with respect to an axis of symmetry passing through the apex and the center of the one side.

According to the present invention, even when the area of interest includes a generally semicircular imaging target, the shape of the CT imaging area can be adapted to the shape of the area of interest with higher precision. Thus, the amount of unnecessary exposure to the X-ray can be further decreased.

In an embodiment of the present invention, the control section may change the radiation range restricted by the X-ray restriction section, such that a generally triangular imaging area X-ray CT imaging performed on the CT imaging area in the case where the CT imaging area has the generally triangular shape as seen in a plan view, or another-shaped imaging area X-ray CT imaging performed on the CT imaging area in the case where the CT imaging area has another shape, is selectable.

According to the present invention, for example, the CT imaging area having a generally triangular shape as seen in a plan view in which the anterior teeth and the left and right posterior teeth of the dental arch are accommodated, or the CT imaging area having an elliptical shape as seen in a plan view in which a local site of only the posterior teeth is accommodated, can be selected. Therefore, the X-ray CT imaging device is applicable to any type of X-ray CT imaging, and the applicability of the X-ray CT imaging device which can decrease the amount of unnecessary exposure to the X-ray is improved.

In an embodiment of the present invention, the control section may change the radiation range restricted by the X-ray restriction section, such that first X-ray CT imaging or second X-ray CT imaging is selectable. The first X-ray CT imaging is an imaging for first area of interest which is entirety of an area of interest of the subject, and the second X-ray CT imaging is an imaging for second area of interest which is a part of the first area of interest.

According to the present invention, for example, the first X-ray CT imaging in which the first area of interest is the entirety of the anterior teeth and the left and right posterior teeth of the dental arch, which is the CT imaging area having a generally triangular shape as seen in a plan view, or the second X-ray CT imaging in which the second area of interest is a local site of only the posterior teeth, which is the CT imaging area having a circular (encompassing elliptical) shape as seen in a plan view, can be selected. Therefore, the applicability of the X-ray CT imaging device which can decrease the amount of unnecessary exposure to the X-ray is improved.

In an embodiment of the present invention, the control section may control the movement of the X-ray restriction section to output an X-ray slit beam formed by changing the radiation range restricted by the X-ray restriction section, and may control the imaging mechanism driving section to revolve the support, such that the output X-ray slit beam forms a locus for panorama X-ray imaging, and such that panorama X-ray imaging is performed by the X-ray slit beam.

According to the present invention, even when a panorama image is required, it is not necessary to prepare another X-ray imaging device. The X-ray CT imaging device which can decrease the amount of unnecessary exposure to the X-ray is usable to perform panorama X-ray imaging by use of an X-ray slit beam.

Effect of the Invention

According to the present invention, an X-ray CT imaging device is provided which can direct X-ray to an area of interest appropriately even when, for example, the height of the area of interest with respect to the X-ray detector, which is revolving, varies with respect to the revolution direction, and thus can reduce the amount of unnecessary exposure to the X-ray and can perform X-ray imaging of the area of interest with certainty.

BRIEF DESCRIPTION OF DRAWINGS

FIGS. 5A and 5B provide schematic isometric views of an X-ray generation section in the state of outputting an X-ray cone beam with a restricted radiation range.
FIGS. 6A, 6B, and 6C show positional adjustment of length direction blocking plates and lateral direction blocking plates.
FIGS. 7 A, 7A, 7C show positional adjustment of length direction blocking plates and lateral direction blocking plates in another embodiment.
FIGS. 8A, 8B, and 8C show an X-ray detection sections.
FIGS. 9A and 9B show local X-ray CT imaging of imaging a local imaging target.
FIGS. 10A and 10B show local X-ray CT imaging of imaging a local imaging target.
FIGS. 11A and 11B show local X-ray CT imaging of imaging a local imaging target.
FIGS. 23A-23E show adjustment of an amount of X-ray to be directed to the subject during X-ray CT imaging.
FIGS. 24A-24G show CT imaging areas which are generally triangular as seen in a plan view.
FIGS. 25A and 25B show restriction on an expansion of the X-ray cone beam performed by a beam formation mechanism in another embodiment.
FIGS. 27A and 27B show restriction on the expansion of the X-ray cone beam when the revolution center is moved.

FIGS. 35A and 35B provide schematic views as seen in an x-axis direction of an X-ray cone beam BX restricted regarding the length direction radiation range when an X-ray generator is at prescribed positions.

DESCRIPTION OF THE PREFERRED EMBODIMENTS

Hereinafter, an X-ray CT imaging device 1 according to the present invention will be described with reference to FIG. 1 through FIG. 8.

Figure 1:
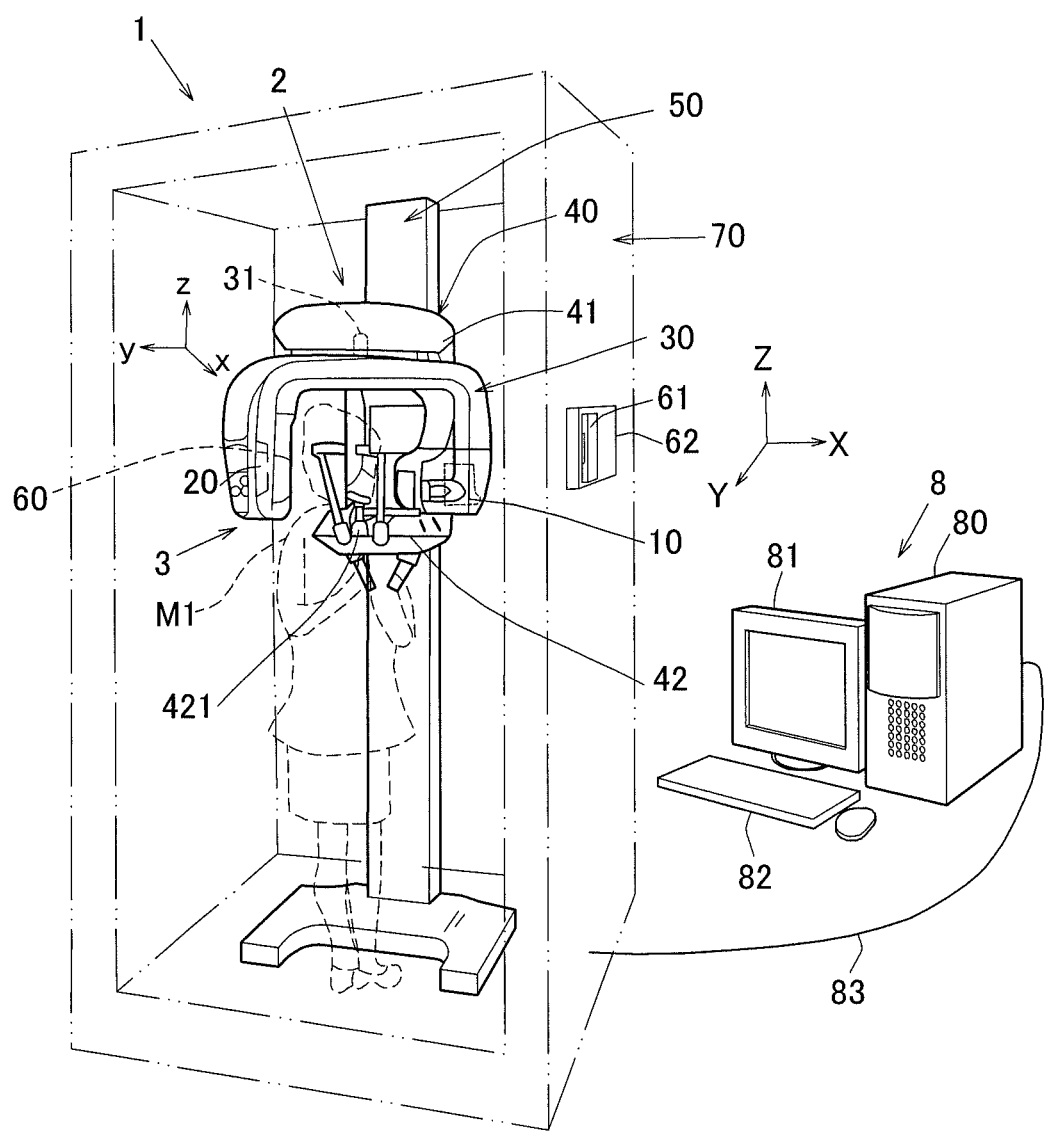
FIG. 1 is a schematic isometric view of an X-ray CT imaging device.
Figure 2:
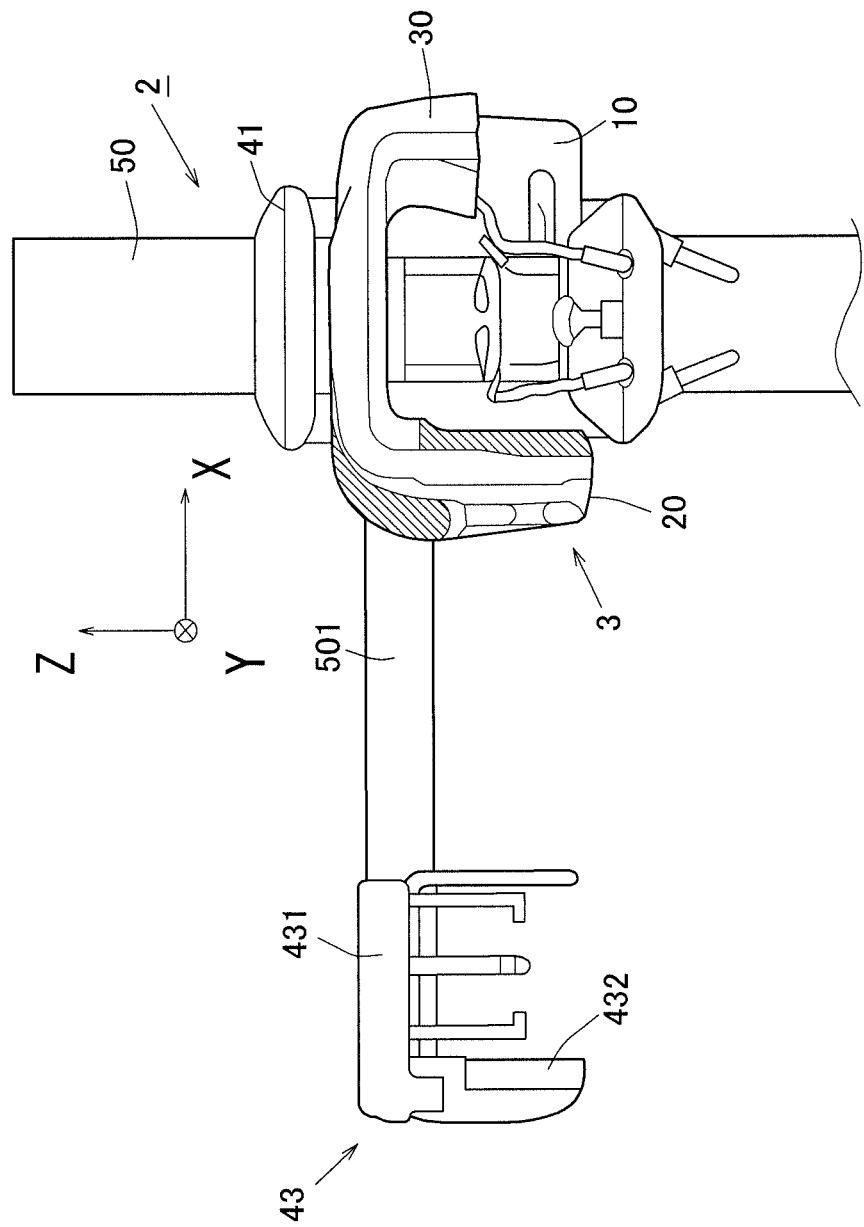
FIG. 2 is a partial front view of the X-ray CT imaging device having a cephalostat mounted thereon.
Figure 3:
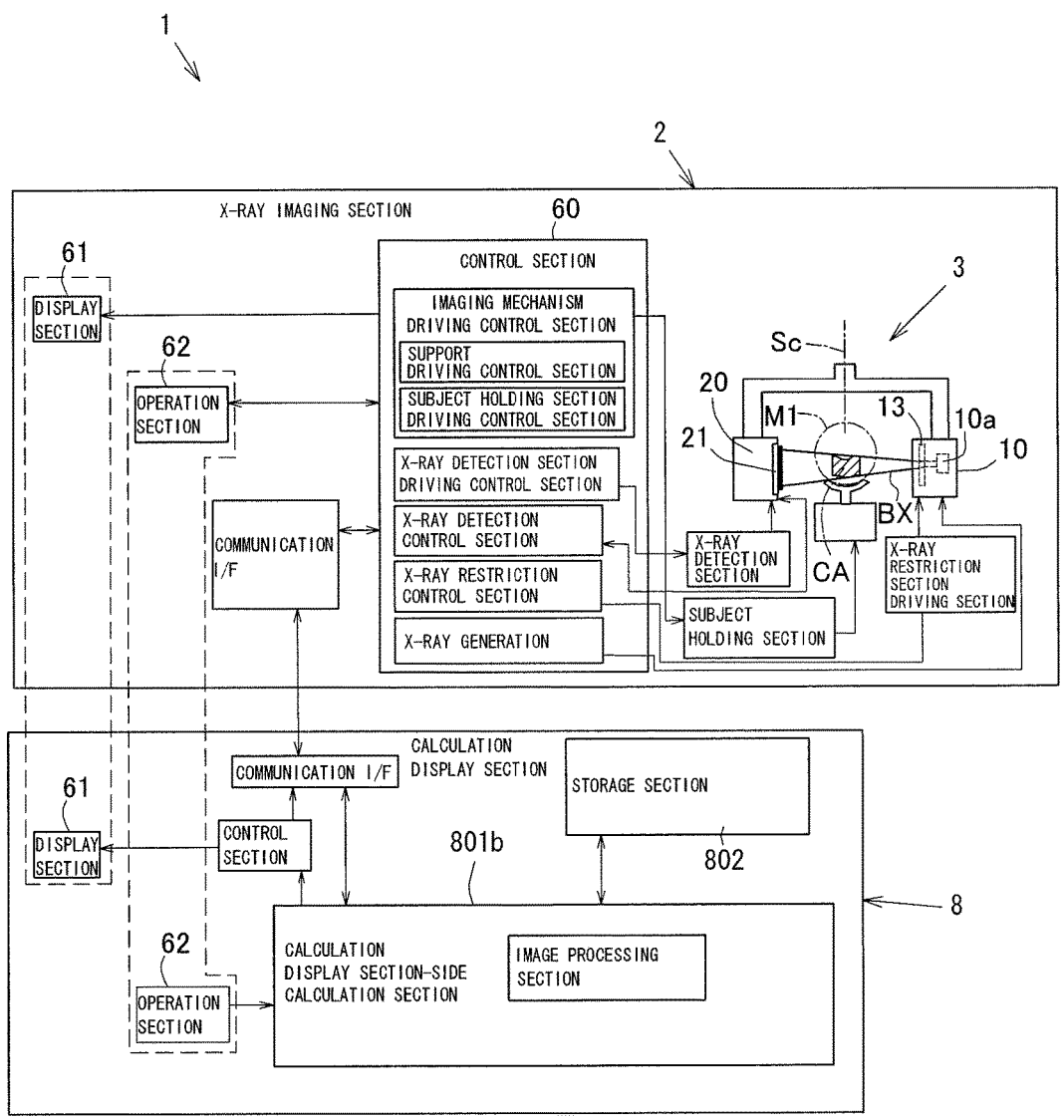
FIG. 3 is a block diagram showing a structure of the X-ray CT imaging device.
Figure 4:
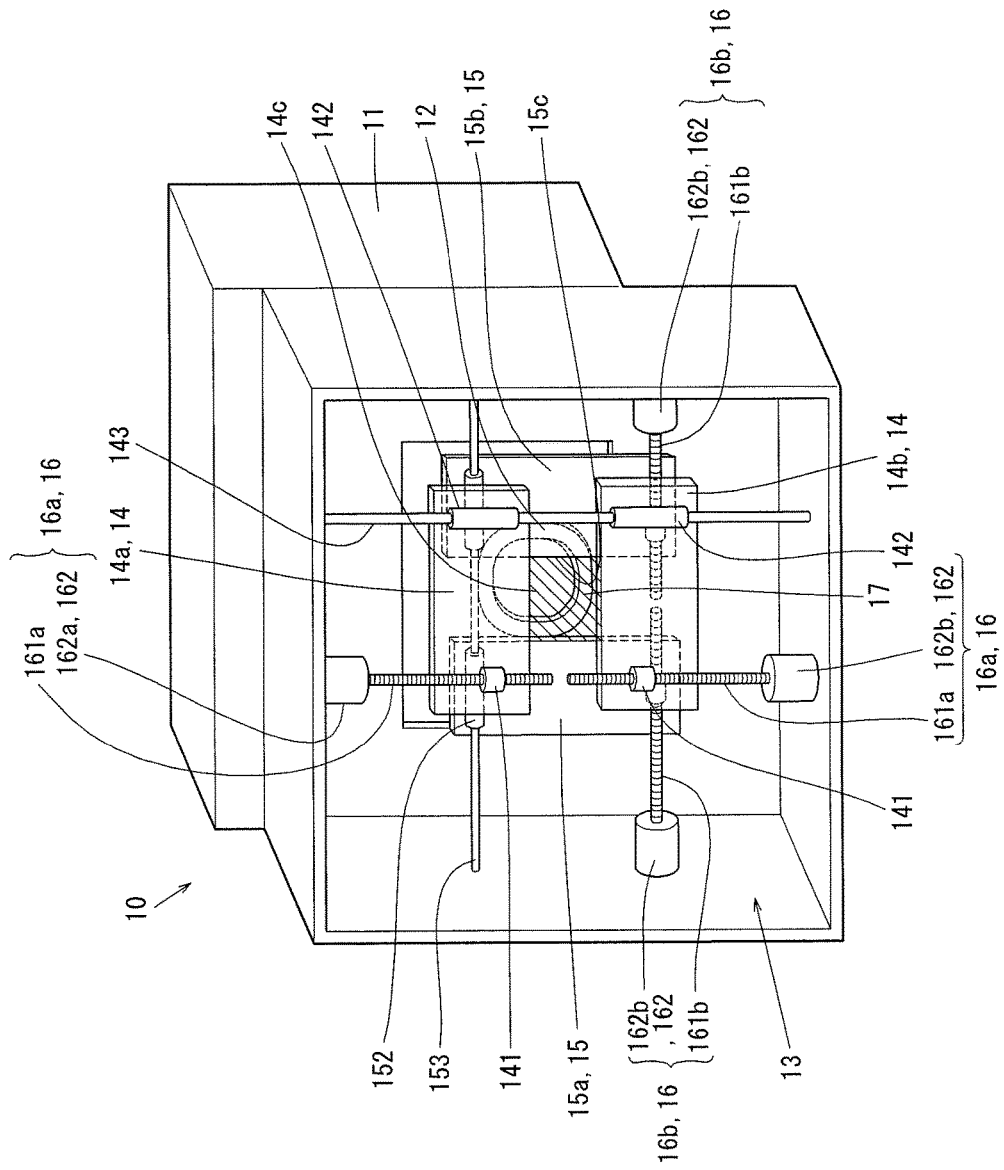
FIG. 4 is a schematic isometric view of a beam formation mechanism.

FIG. 1 is a schematic isometric view of the X-ray CT imaging device 1, and FIG. 2 is a partial front view of the X-ray CT imaging device 1 having a cephalostat 43 mounted thereon. FIG. 3 is a block diagram showing a structure of the X-ray CT imaging device 1, and FIG. 4 is a schematic isometric view of a beam formation mechanism 13.

FIG. 5 provides schematic isometric views of an X-ray generation section 10 in the state of outputting an X-ray cone beam BX with a restricted radiation range. FIG. 6 and FIG. 7 show positional adjustment of length direction blocking plates 14 and lateral direction blocking plates 15. FIG. 8 shows an X-ray detection section 20.

In more detail, FIG. 5(*a*) is a schematic isometric view of the X-ray generation section 10 in the state of outputting an X-ray cone beam BX1 for a large radiation field CT, and FIG. 5(*b*) is a schematic isometric view of the X-ray generation section 10 in the state of outputting an X-ray cone beam BX2 for a small radiation field CT.

FIG. 6(*a*) is a front view showing positional adjustment of the length direction blocking plates 14 and the lateral direction blocking plates 15, which is performed for restricting the radiation range of the X-ray cone beam BX to a radiation range for the large radiation field CT. FIG. 6(*b*) is a front view showing positional adjustment of the length direction blocking plates 14 and the lateral direction blocking plates 15, which is performed for restricting the radiation range of the X-ray cone beam BX to a radiation range for the small radiation field CT. FIG. 6(*c*) is a front view showing positional adjustment of the length direction blocking plates 14 and the lateral direction blocking plates 15, which is performed for restricting the radiation range of the X-ray to a radiation range for panorama imaging, thus providing an X-ray slit beam BXP. FIGS. 7(*a*), 7(*b*) and 7(*c*) respectively show positional adjustment substantially the same as that shown in FIGS. 6(*a*), 6(*b*) and 6(*c*) but performed with L-shaped blocking plates.

FIG. 8(*a*) is a schematic isometric view of the X-ray detection section 20. FIG. 8(*b*) is a cross-sectional view taken along line A-A shown in FIG. (a), and FIG. 8(*c*) is a cross-sectional view taken along line B-B shown in FIG. (a).

The X-ray CT imaging device 1 roughly includes a main body 2 for performing X-ray CT imaging and collecting projection data, and an information processing device 8 for processing the projection data collected by the main body 2 and generating various types of images. Preferably, the main body 2 is accommodated in a hollow parallelepiped X-ray-proof chamber 70 longer in a height direction and is connected to the information processing device 8 located outside the X-ray-proof chamber 70 via a connection cable 83.

The main body 2 includes the X-ray generation section 10 for outputting an X-ray cone beam BX or an X-ray slit beam BXP, formed of a flux of X-rays, toward a subject M1, the X-ray detection section 20 for detecting the X-ray output by the X-ray generation section 10, a revolving arm 30 for supporting the X-ray generation section 10 and the X-ray detection section 20, a support pillar 50 extending in the vertical direction, an elevation section 40 for suspending the revolving arm 30 and capable of elevating up and down in the vertical direction with respect to the support pillar 50, and a main body control section 60. The X-ray generation section 10, the X-ray detection section 20 and the beam formation mechanism 13 located at a position close to the X-ray generation section 10 on the X-ray detection section 20 side are included in an imaging mechanism 3.

The X-ray generation section 10 and the X-ray detection section 20 are secured while being suspended from both of two ends of the revolving arm 30 respectively, and are supported so as to face each other. The revolving arm 30 is secured while being suspended by the elevation section 40 via a revolution shaft 31 extending in the vertical direction.

The revolving arm 30 is generally inverted U-shaped as seen in a front view, and is revolvable about the revolution shaft 31 provided at an upper end thereof as a revolution center Sc. At both of two ends of the revolving arm 30 which is generally inverted U-shaped, the X-ray generation section 10 and the X-ray detection section 20 are attached respectively. The revolving arm 30 is not limited to having such a shape. For example, the revolving arm 30 may be an annular arm rotatable about the center thereof, and may support the X-ray generation section 10 and the X-ray detection section 20 facing each other.

Hereinafter, a direction parallel to an axial direction of the revolving shaft 31 (herein, the vertical direction) is defined as the "Z-axis direction", and a direction intersecting the Z-axis direction is defined as the "X-axis direction". A direction intersecting the X-axis direction and the Z-axis direction is defined as the "Y-axis direction". The X-axis direction and the Y-axis direction may be defined arbitrarily. Herein, where a test subject, namely, the subject M1, stands facing the support pillar 50 as being positioned by the X-ray CT imaging device 1, the left-right direction of the subject M1 is defined as the "X-axis direction", and the front-rear direction of the subject M1 is defined as the "Y-axis direction". In this embodiment, the X-axis direction, the Y-axis direction and the Z-axis direction are perpendicular to each other. Hereinafter, the Z-axis direction may be referred to as the "vertical direction", and a direction of a plane defined by the X-axis direction and the Y-axis direction may be referred to as the "horizontal direction".

In the meantime, regarding a three-dimensional coordinate system for the revolving arm 30, a direction in which the X-ray generation section 10 and the X-ray detection section 20 face each other is defined as the "y-axis direction", a horizontal direction perpendicular to the y-axis direction is defined as the "x-axis direction". The vertical direction perpendicular to the x-axis direction and the y-axis direction is defined as the "z-axis direction". In this and the following embodiments, the Z-axis direction is the same as the z-axis direction. In this embodiment, the revolving arm 30 revolves about the revolution shaft 31, extending in the vertical direction, as the revolution axis. Therefore, the xyz Cartesian coordinate system rotates about the Z-axis (=z-axis) with respect to the XYZ Cartesian coordinate system. The "z-axis direction" is also referred to as the "length direction", and the "x-axis direction" is also referred to as the "lateral direction".

Where the X-ray generation section 10 and the X-ray detection section 20 shown in FIG. 1 are seen in a plan view, a direction from the X-ray generation section 10 to the X-ray detection section 20 is defined as the "(+y) direction". A horizontal rightward direction perpendicular to the (+y) direction (forward from the subject M1 when the revolving arm 30 is directed as shown in FIG. 1) is set as the "(+x)

direction", and the upward direction of the vertical direction is defined as the "(+z) direction".

The elevation section 40 includes an upper frame 41 and a lower frame 42, and protrudes in a direction opposite to the side on which the elevation section 40 is in engagement with the support pillar 50 standing in the vertical direction, namely, protrudes toward the front side of the X-ray-proof chamber 70.

To the upper frame 41, the revolution shaft 31 for the revolving arm 30 is attached. The elevation section 40 moves in the vertical direction along the support pillar 50, and thus the revolving arm 30 can be moved up and down.

The upper frame 41 includes a revolution motor 37 for revolving the revolving arm 30 about the revolution shaft 31 as the center. A rotation force provided by the revolution motor 37 is transmitted to the revolving arm 30 by use of a transmission mechanism (not shown) including a belt, a pulley, a rotation shaft and the like and passing through the revolution shaft 31. Thus, the revolving arm 30 is revolved. The revolution shaft 31 is structured to extend in the vertical direction in this embodiment, but the revolving shaft 31 may be inclined at any angle with respect to the vertical direction.

In the example shown in the figure, the upper frame 41 includes a mechanical element for driving the revolving arm 30 and acts as an imaging mechanism driving section. The upper frame 41 as the imaging mechanism driving section drives the imaging mechanism 3 by driving the revolving arm 30.

The revolution motor 37 may be secured in the upper frame 41, or may be secured in the revolving arm 30 to have a pivoting force on the revolution shaft 31.

A bearing 38 (see FIG. 28) is located between the revolution shaft 31 and the revolving arm 30, so that the revolving arm 30 revolves smoothly with respect to the revolution shaft 31.

The revolution shaft 31, the bearing 38, the transmission mechanism including the belt, the pulley, the rotation shaft and the like, and the revolution motor 37 (see FIG. 28) form an example of revolution mechanism for revolving the revolving arm 30. With this revolution mechanism, the revolving arm 30 revolves with respect to the revolution shaft 31, which is not rotated. The revolution mechanism is not limited to such a structure.

For example, the revolution shaft 31 may be rotatably attached to the revolving arm 30, and the revolving arm 30 may be revolved by a rotation of the revolution shaft 31 with respect to the upper frame 41.

The lower frame 42 accommodates a subject securing section 421 including a head holder for securing the subject M1 (herein, the head of the human body) from left and right, a chin rest for securing the chin, or the like. The subject securing section 421 may include an ear rod including a part insertable into left and right earholes of the head of the human body.

The revolving arm 30 is elevated up and down along with the elevating movement of the elevation section 40, so as to be located at an appropriate position suitable to the height of the subject M1. In this state, the subject M1 is secured by the subject securing section 421. In the example shown in FIG. 1, the subject securing section 421 secures the subject M1 such that the body axis of the subject M1 is almost the same direction as the axial direction of the revolution axis 31.

The main control section 60 is a control section for controlling an operation of elements of the main body 2. As shown in FIG. 1, the main control section 60 is located inside the X-ray detection section 20.

To an outer surface of a wall of the X-ray-proof chamber 70 for accommodating the main body 2, a display section 61 including a liquid crystal monitor or the like for displaying various types of information based on the control of the main body control section 60 and an operation panel 62 including buttons or the like usable for inputting various types of instructions to the main body control section 60 are attached.

The operation panel 62 is also usable for, for example, specifying the position or the like of an imaging area of a biological organ or the like. X-ray imaging may be performed in various modes. The modes can be made selectable by an operation on the operation panel 62.

The operation panel 62 may be provided in the main body 2 or may be provided both on the outer surface of the wall of the X-ray-proof chamber 70 and in the main body 2.

The information processing device 8 includes an information processing main body 80, an display section 81 including a display device such as a liquid crystal monitor or the like, and an operation section 82 including a keyboard, a mouse or the like. An operator can input various types of instructions to the information processing device 8 via the operation section 82. The display section 81 may include a touch panel. In this case, the display section 81 has a part of, or the entirety of, the functions of the operation section 82.

The information processing main body 80 includes, for example, a computer, a work station or the like, and can transmit or receive various types of data to or from the main body 2 via the connection cable 83, which is a communication cable. Alternatively, the main body 2 and the information processing device 8 may transmit or receive data wirelessly.

The information processing device 8 is a processing device for processing the projection data acquired by the main body 2 and reconstructing three-dimensional data (volume data) represented by voxel. For example, the information processing device 8 can set a specific plane in the three-dimensional data and reconstruct a tomography image of the specific plane.

As shown in FIG. 2, the cephalostat 43 may be mounted on the X-ray CT imaging device 1. In more detail, the cephalostat 43 is attached to, for example, an arm 501 extending horizontally from a position in the middle of the support pillar 50. The cephalostat 43 includes a securing tool 431 for securing the head of the human body at a defined position and an X-ray detector 432 for cephalo imaging. As the cephalostat 43, any of various types, for example, a cephalostat disclosed in Japanese Laid-Open Patent Publication No. 2003-245277, can be adopted.

Now, with reference to FIG. 4 through FIG. 7, the beam formation mechanism 13 for blocking and restricting the radiation range of the X-ray generated by the X-ray generation section 10 to form an X-ray cone beam expanding in a cone shape toward the X-ray detection section 20 will be described.

The X-ray generation section 10 suspended from the revolving arm 30 so as to face the X-ray detection section 20 includes an X-ray generator 10a accommodated in a housing 11, and the X-ray generator 10a includes an X-ray tube. In a front surface of the housing 11, an output opening 12 for transmitting the X-ray generated in the X-ray generator 10a accommodated in the housing 11 is formed. Forward to the output opening 12 (toward the viewer of FIG. 4), the beam formation mechanism 13 is provided.

The beam formation mechanism 13 includes the length direction blocking plates 14 (14a, 14b) for blocking the radiation range of the X-ray in the length direction (z direction), the lateral direction blocking plates 15 (15a, 15b)

for blocking the radiation range of the X-ray in a lateral direction (x-axis direction), and blocking plate moving mechanisms 16 (16a, 16b) for moving the length direction blocking plates 14 and the lateral direction blocking plates 15.

The length direction blocking plates 14 include an upper length direction blocking plate 14a and a lower length direction blocking plate 14b which are longer in the lateral direction and are respectively located above and below the output opening 12 as seen in the front view. The lateral direction blocking plates 15 include a left lateral direction blocking plate 15a and a right lateral direction blocking plate 15b which are longer in the length direction and are respectively located to the left and to the right of the output opening 12 as seen in the front view. As shown in FIG. 4, the lateral direction blocking plates 15 are located on the X-ray generation section 10 side with respect to the length direction blocking plates 14. Alternatively, the length direction blocking plates 14 may be located on the X-ray generation section 10 side with respect to the lateral direction blocking plates 15.

The blocking plate moving mechanisms 16 include blocking plate length direction moving mechanisms 16a for moving the two length direction blocking plates 14 in the length direction, and blocking plate lateral direction moving mechanisms 16b for moving the two lateral direction blocking plates 15 in the lateral direction.

Each blocking plate length direction moving mechanism 16a acts as follows. A length direction screw shaft 161a which is in screw engagement with a screw groove 141 (to-be-guided member having a female thread in an inner surface thereof) provided on the length direction blocking plate 14 in the length direction is rotated by a positional adjustment motor 162a (162), and thus each length direction blocking plate 14 is moved in the length direction. One of the blocking plate length direction moving mechanisms 16a is located at an upper position in correspondence with the upper length direction blocking plate 14a, and the other blocking plate length direction moving mechanism 16a is located at a lower position in correspondence with the lower length direction blocking plate 14b. Therefore, the upper length direction blocking plate 14a and the lower length direction blocking plate 14b can move in the length direction independently from each other.

The blocking plate length direction moving mechanisms 16a are located offset in the lateral direction from the lateral-direction center of the length direction blocking plates 14 which are longer in the lateral direction. At a position offset in the lateral direction from the lateral-direction center of the length direction blocking plates 14 in the opposite direction, an inclination restriction shaft 143 is provided. The inclination restriction shaft 143 is inserted through inclination restriction holes 142 (to-be-guided members each having a length direction through-hole) in correspondence with the upper length direction blocking plate 14a and the lower length direction blocking plate 14b. Therefore, the length direction blocking plates 14 can be moved in the length direction by the blocking plate length direction moving mechanisms 16a without being inclined.

Each blocking plate lateral direction moving mechanism 16b acts as follows. A lateral direction screw shaft 161b which is in screw engagement with a screw groove 161 (to-be-guided member having a female thread in an inner surface thereof) provided on the lateral direction blocking plate 15 in the lateral direction is rotated by a positional adjustment motor 162a (162), and thus each lateral direction blocking plate 15 is moved in the lateral direction. One of the blocking plate lateral direction moving mechanisms 16b is located at a left position in correspondence with the left lateral direction blocking plate 15a, and the other blocking plate lateral direction moving mechanism 16b is located at a right position in correspondence with the right lateral direction blocking plate 15b. Therefore, the left lateral direction blocking plate 15a and the right lateral direction blocking plate 15b can move in the lateral direction independent from each other.

The blocking plate lateral direction moving mechanisms 16b are located offset in the length direction from the length-direction center of the lateral direction blocking plates 15 which are longer in the length direction. At a position offset in the length direction from the length-direction center of the lateral direction blocking plates 15 in the opposite direction, an inclination restriction shaft 153 is provided. The inclination restriction shaft 153 is inserted through inclination restriction holes 152 (to-be-guided members each having a lateral direction through-hole) in correspondence with the left lateral direction blocking plate 15a and the right lateral direction blocking plate 15b. Therefore, the lateral direction blocking plates 15 can be moved in the lateral direction by the blocking plate lateral direction moving mechanisms 16b without being inclined.

In this manner, the beam formation mechanism 13 includes the length direction blocking plates 14, the lateral direction blocking plates 15, and the blocking plate moving mechanisms 16 and is located forward with respect to the output opening 12 of the X-ray generation section 10. Owing to this, the radiation range of the X-ray generated by the X-ray generation section 10 is blocked and restricted, and thus the X-ray cone beam BX expanding in a cone shape toward the X-ray detection section 20 can be formed.

This will be described in more detail. The distance between edges 14c, facing each other, of the upper length direction blocking plate 14a and the lower length direction blocking plate 14b is adjusted by the blocking plate length direction moving mechanisms 16a, and the distance between edges 15c, facing each other, of the left lateral direction blocking plate 15a and the right lateral direction blocking plate 15b is adjusted by the blocking plate lateral direction moving mechanisms 16b. Thus, an opening 17 having a square shape as seen in a front view for forming the X-ray cone beam having a desired shape can be formed by the edges 14c, facing each other, of the upper length direction blocking plate 14a and the lower length direction blocking plate 14b and the edges 15c, facing each other, of the left lateral direction blocking plate 15a and the right lateral direction blocking plate 15b.

This will be described more specifically. As shown in FIG. 5(a) and FIG. 6(a), the distance between the edges 14c, facing each other, of the upper length direction blocking plate 14a and the lower length direction blocking plate 14b is adjusted to be large, and the distance between the edges 15c, facing each other, of the left lateral direction blocking plate 15a and the right lateral direction blocking plate 15b is adjusted to be large. In this case, a large radiation field opening 17a has a large square shape as seen in a front view. The X-ray transmitted through the large radiation field opening 17a has a large square cross-section. Thus, a large radiation field X-ray cone beam BX1 expanding in a cone shape can be directed to the X-ray detection section 20.

By contrast, as shown in FIG. 5(b) and FIG. 6(b), the distance between the edges 14c, facing each other, of the upper length direction blocking plate 14a and the lower length direction blocking plate 14b is adjusted to be small, and the distance between the edges 15c, facing each other, of the left lateral direction blocking plate 15a and the right lateral direction blocking plate 15b is adjusted to be small. In this case, a small radiation field opening 17b has a small square shape as seen in a front view. The X-ray transmitted through the small radiation field opening 17b has a small square cross-section. Thus, a small radiation field X-ray cone beam BX2 expanding in a cone shape can be directed to the X-ray detection section 20.

As shown in FIG. 6(c), the distance between the edges 14c, facing each other, of the upper length direction blocking plate 14a and the lower length direction blocking plate 14b is adjusted to be large, and the distance between the edges 15c, facing each other, of the left lateral direction blocking plate 15a and the right lateral direction blocking plate 15b is adjusted to be small. In this case, a panorama imaging opening 17c has a rectangular shape longer in the length direction as seen in a front view. The X-ray transmitted through the panorama opening 17c has a rectangular cross-section longer in the length direction. Thus, an X-ray slit beam BXP expanding in a cone shape longer in the length direction can be directed to the X-ray detection section 20.

The beam formation mechanism 13 described above moves the two length direction blocking plates 14 and the two lateral direction blocking plates 15 by use of the blocking plate moving mechanisms 16 to form the opening 17 for outputting a desired X-ray cone beam BX. Alternatively, as shown in FIG. 7, two L-shaped blocking plates 18 having an L-shape as seen in a front view may be located in point symmetry around a position which is to be the center of the opening 17, and the opening 17 can be formed by edges 18a along interior angle portions of the L-shaped blocking plates 18.

In this case, both of the blocking plate length direction moving mechanism 16a and the blocking plate lateral direction moving mechanism 16b are provided for each of the L-shaped blocking plates 18, and each L-shaped blocking plate 18 is moved in the length direction and the lateral direction. Thus, the shape of the opening 17 can be adjusted.

Now, with reference to FIG. 8, the X-ray detection section 20 will be described.

The X-ray detection section 20 suspended from the revolving arm 30 so as to face the X-ray generation section 10 includes an X-ray detector 21 for detecting X-ray, detector holders 22 for holding the X-ray detector 21 therein, and moving mechanisms 23 for sliding the X-ray detector 21 with respect to the detector holders 22.

The X-ray detector 21 includes an X-ray sensor which forms a detection plane 21a including semiconductor imaging elements, which are detection elements for detecting the X-ray, in a two-dimensional array, namely, in the length direction and the lateral direction. The X-ray sensor may be, for example, a MOS sensor or a CCD sensor, but is not limited to these. As the X-ray sensor, a flat panel detector (FPD) such as a CMOS sensor or the like, an X-ray fluorescent image intensifier tube (XII), any other solid-state imaging element, or any of various other sensors may be adopted.

The detector holders 22 hold the X-ray detector 21 such that the X-ray detector 21 is movable in the length direction and the lateral direction, by use of the moving mechanisms 23. In more detail, the detector holders 22 include a first holder 22a for holding the X-ray detector 21 such that the X-ray detector 21 is movable in the lateral direction and a second holder 22b for holding the first holder 22a which holds the X-ray detector 21 such that that the first holder 22a is movable in the length direction. The first holder 22a has a lateral direction groove 221 which is fit to the X-ray detector 21 such that the X-ray detector 21 is slidable in the lateral direction. The second holder 22b has a length direction groove 222 which is fit to the first holder 22a such that the first holder 22a is slidable in the length direction.

A lateral direction moving mechanism 23a for moving the X-ray detector 21 in the lateral direction with respect to the first holder 22a, and a length direction moving mechanism 23b for moving the first holder 22a in the length direction with respect to the second holder 22b, may have substantially the same structure as that of, for example, the blocking plate moving mechanisms 16 for moving the length direction blocking plates 14 and the lateral direction blocking plates 15 in the beam formation mechanism 13.

Owing to such a structure of the X-ray detection section 20, the X-ray detector 21 is moved with respect to the detector holders 22 in accordance with the shape of the X-ray cone beam output from the X-ray generator 10 or the position irradiated with the X-ray cone beam. Therefore, the X-ray cone beam BX can be projected to the detection plane 21a with certainty.

In the X-ray CT imaging device 1 having the above-described structure, as shown in FIG. 3, the beam formation mechanism 13, the revolution motor 37 (see FIG. 28), the X-ray generation section 10 and the X-ray detection section 20 are connected to the main body control section 60. These elements are driven in accordance with a predetermined program, and thus X-ray CT imaging of a local imaging target OB1 can be performed appropriately. Hereinafter, a form in which X-ray CT imaging of the local imaging target OB1 is performed by the X-ray CT imaging device 1 will be described.

In the following description, the local imaging target OB1 is the following. The dental arch of the upper jaw includes anterior teeth-side teeth T1 including the anterior teeth, left posterior teeth-side teeth T2 including the left posterior teeth, and right posterior teeth-side teeth T3 including the right posterior teeth (hereinafter, referred to as the "anterior teeth T1", the "left posterior teeth T2", and the "right posterior teeth T3"). Among the left posterior teeth T1, one left posterior tooth T2A is the local imaging target OB1. In order to perform X-ray CT imaging of the left posterior tooth T2A as the local imaging target OB1, an area of interest including the left posterior tooth T2A is subjected to X-ray CT imaging as a cylindrical local CT imaging area CAa.

Figure 32:
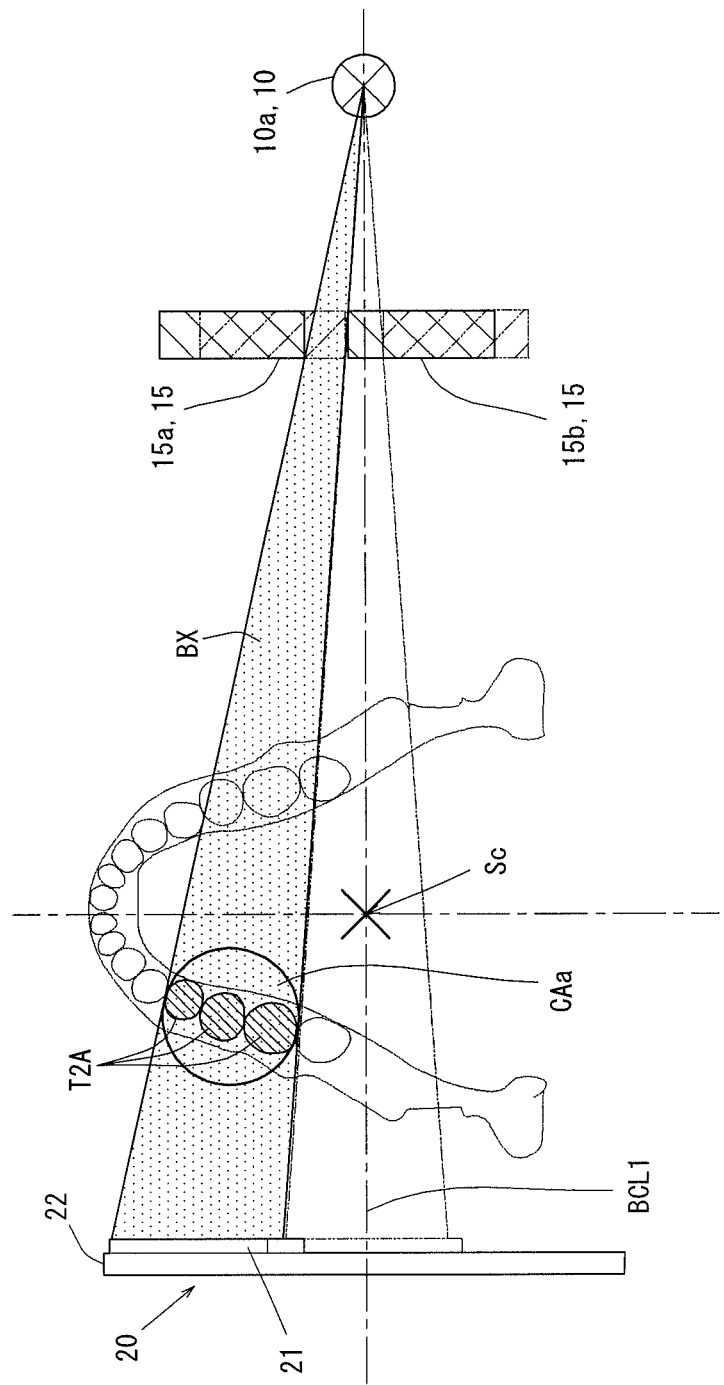
FIG. 32 is a schematic plan view of local X-ray CT imaging of imaging a local imaging target in another embodiment with a different range of target.

In this specification, the imaging target is one tooth for the purpose of simplifying the explanation. In the actual examination, however, the imaging target is often a plurality of teeth as shown in FIG. 32 referred to later.

The local CT imaging area CAa is often set to have a width in the length direction which sufficiently accommodate an area from the crown to the root of the tooth (such an area may include the jawbone).

The local CT imaging area CAa may be set to accommodate an area including either a tooth of the upper jaw or a tooth of the lower jaw, or to accommodate an area including both of a tooth of the upper jaw and a tooth of the lower jaw. This is also applicable to the width in the length direction of a CT imaging area Cab described later.

Figure 12:
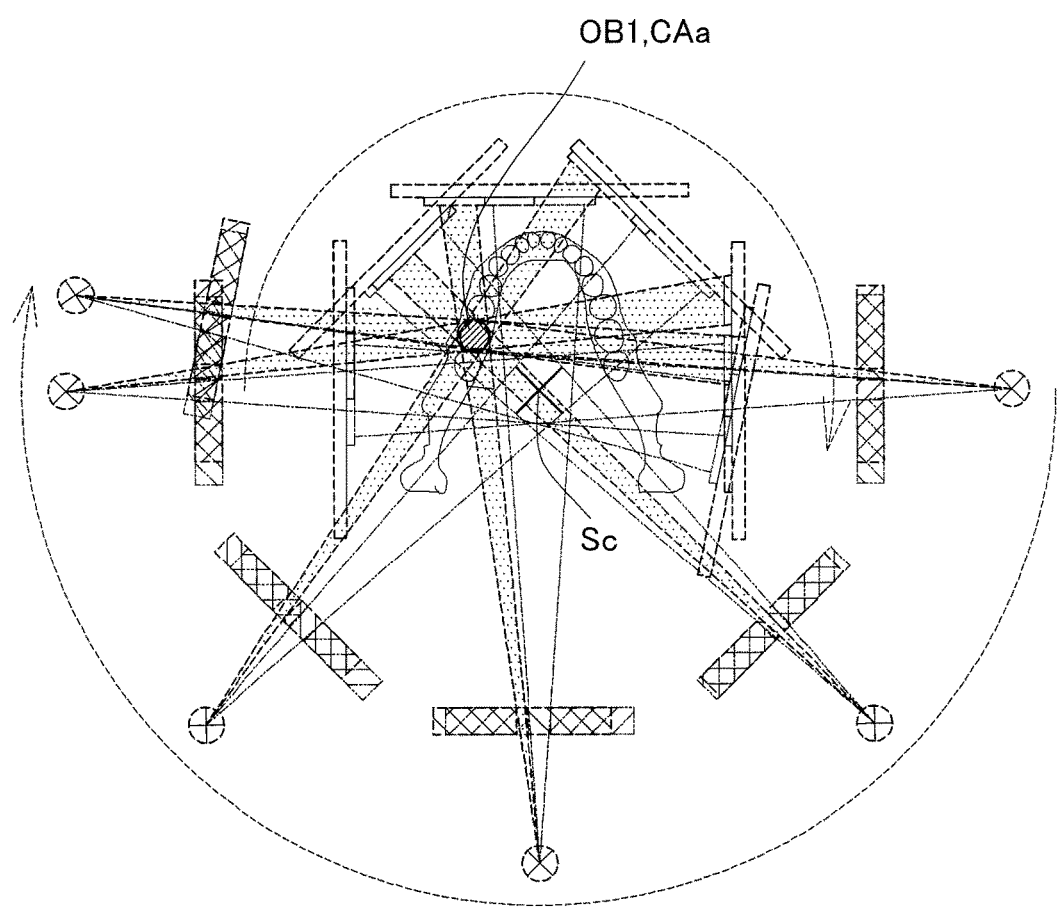
FIG. 12 is a schematic plan view showing a locus of local X-ray CT imaging of imaging a local imaging target.

First, the X-ray CT imaging of the local imaging target OB1 is performed as follows. In the state where the subject M1 is at a prescribed position in the X-ray CT imaging device 1 (see FIG. 1), the revolving arm 30 is at an initial position where the X-ray generation section 10 is on the side of the right posterior teeth T3 and the X-ray detection section 20 is on the side of the left posterior teeth T2 (first revolution position). As shown in FIG. 12, the X-ray CT imaging is performed with the revolving arm 30 being revolved from the initial position by 180 degrees or more about the revolution shaft 31 as the revolution center Sc.

The position of the revolution center Sc is fixed.

This will be described in more detail. While the revolving arm 30 is revolving about the revolution shaft 31 as the revolution center Sc and thus the X-ray cone beam BX is revolving, the X-ray CT imaging device 1 collects projection data by the X-ray detection section 20 for a predetermined number of cycles of revolution. Specifically, the main body control section 60 monitors the revolution motor 37. Each time the revolving arm 30 revolves by a prescribed angle about the revolution shaft 31, X-ray detection data detected by the X-ray detector 21 is collected as the projection data.

The X-ray generation section 10 may be structured such that the X-ray cone beam BX is always output to the subject while the revolving arm 30 is revolving, or such that the X-ray cone beam BX is output to the subject intermittently at the timing when the X-ray detection section 20 detects the X-ray. In the latter case, the X-ray is output to the subject M1 intermittently. Therefore, the amount of exposure to the X-ray can be decreased for the subject M1.

The collected projection data is sequentially transferred to the information processing device 8, and is stored in, for example, a storage section 802. The collected projection data is processed by a computation processing section 801b and reconstructed into three-dimensional data. The computation processing for reconstruction performed by the computation processing section 801b includes prescribed preprocessing, filtering, inverse projection processing and the like. For such computation processing, any of various computation processing technologies including the well-known technologies is applicable.

FIG. 9(a) is a schematic plan view in the case where the revolving arm 30 is at the initial position (first revolution position), and FIG. 9(b) is a schematic plan view in the case where the revolving arm 30 is at a second revolution position. Similarly, FIG. 10(a) is a schematic plan view in the case where the revolving arm 30 is at a third position, and FIG. 10(b) is a schematic plan view in the case where the revolving arm 30 is at a fourth revolution position. FIG. 11(a) is a schematic plan view in the case where the revolving arm 30 is at a fifth position, and FIG. 11(b) is a schematic plan view in the case where the revolving arm 30 is at a sixth revolution position. FIG. 12 represents a locus from the initial position to the sixth revolution position by dashed line.

In this specification, the blocking plates of the beam formation mechanism 13 are shown thick for easier understanding, but in actuality, the blocking plates are much thinner than shown in the figures.

Figure 13A:
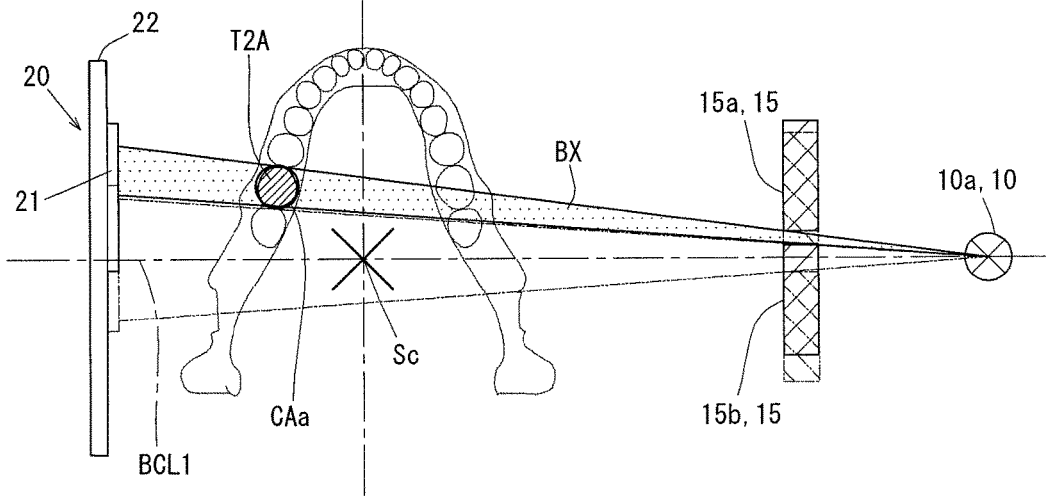
FIGS. 13A and 13B show local X-ray CT imaging at a first revolution position.
Figure 13B:
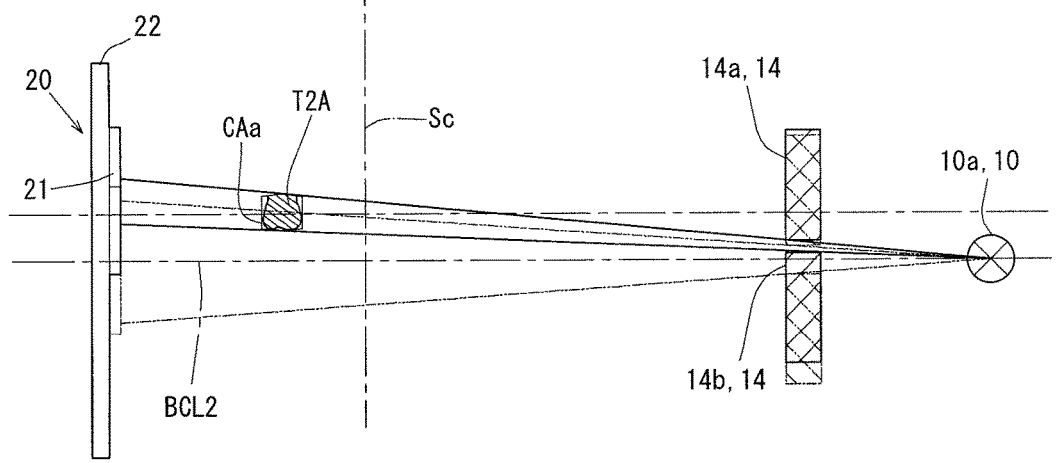
Figure 14A:
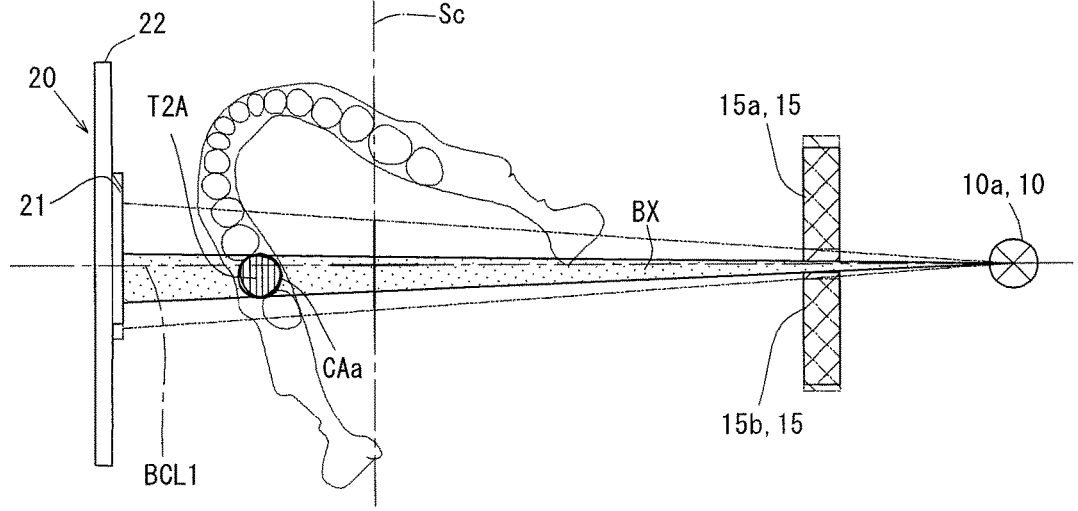
FIGS. 14A and 14B show local X-ray CT imaging at a second revolution position.
Figure 14B:
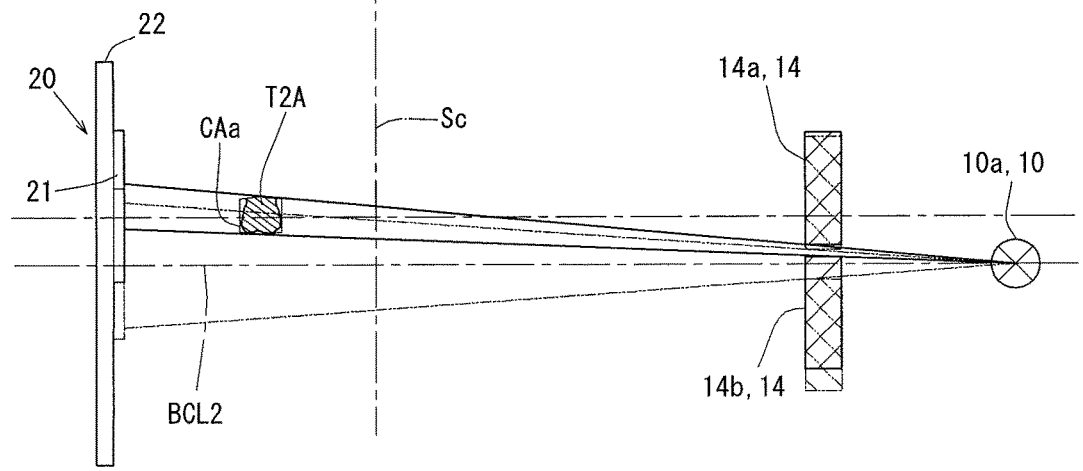
Figure 15A:
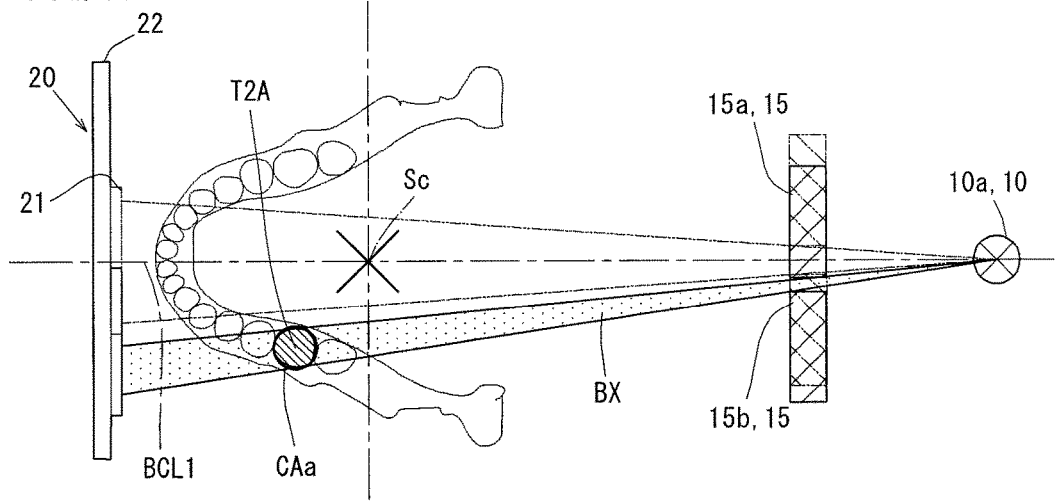
FIGS. 15A and 15B show local X-ray CT imaging at a third revolution position.
Figure 15B:
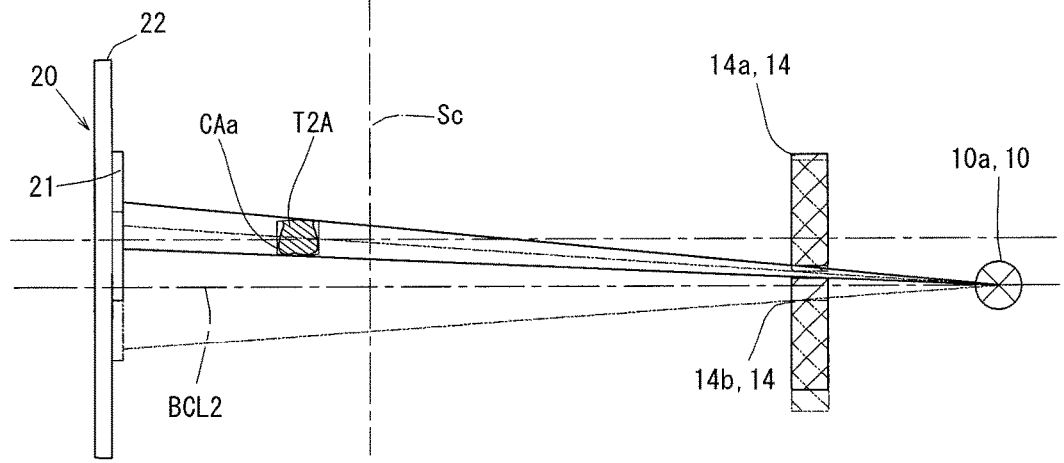
Figure 16A:
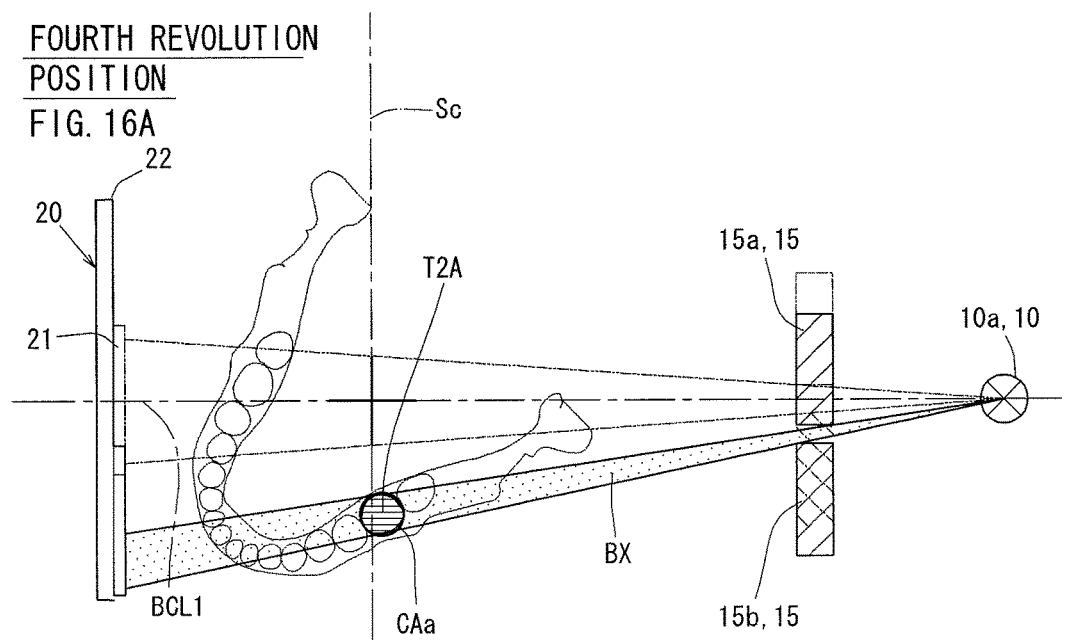
FIGS. 16A and 16B show local X-ray CT imaging at a fourth revolution position.
Figure 16B:
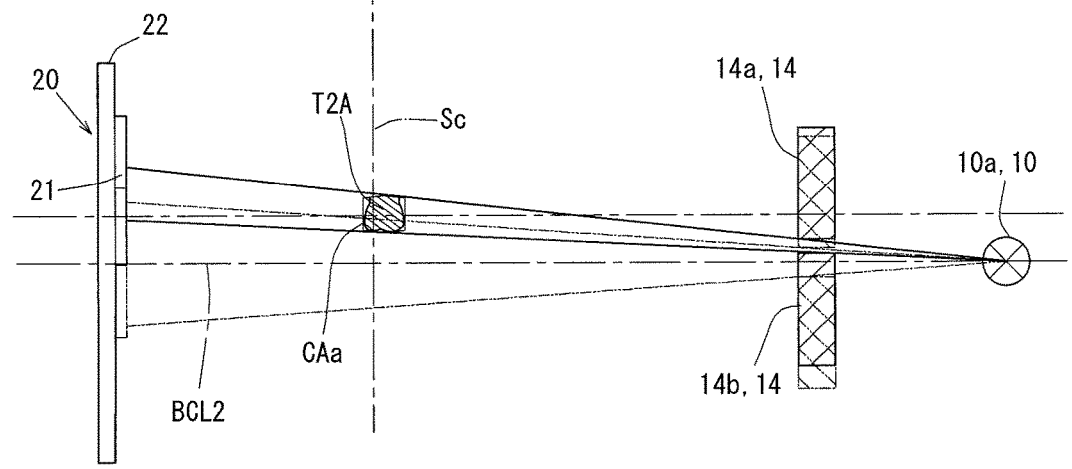
Figure 17A:
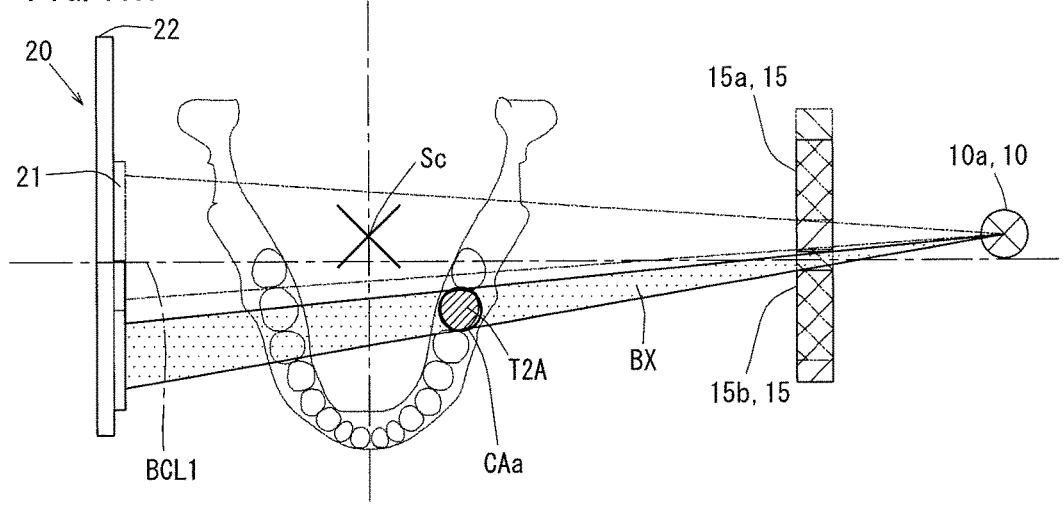
FIGS. 17A and 17B show local X-ray CT imaging at a fifth revolution position.
Figure 17B:
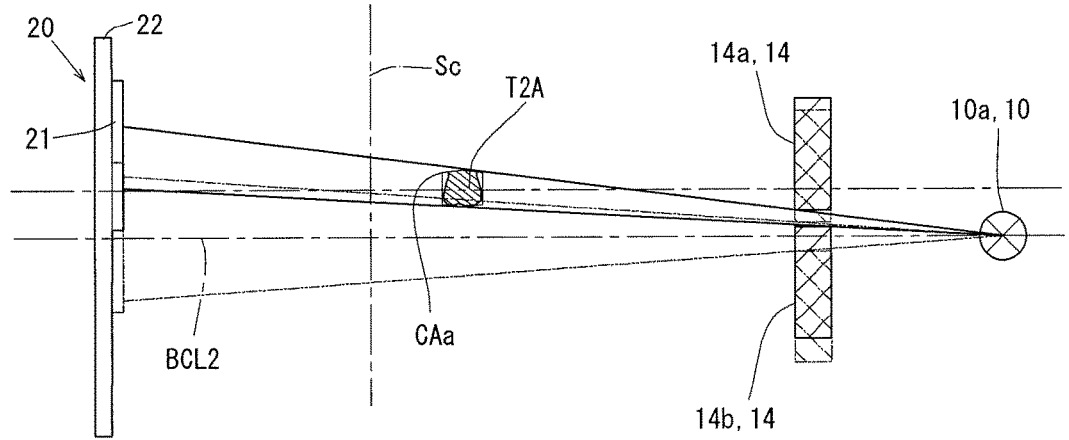
Figure 18A:
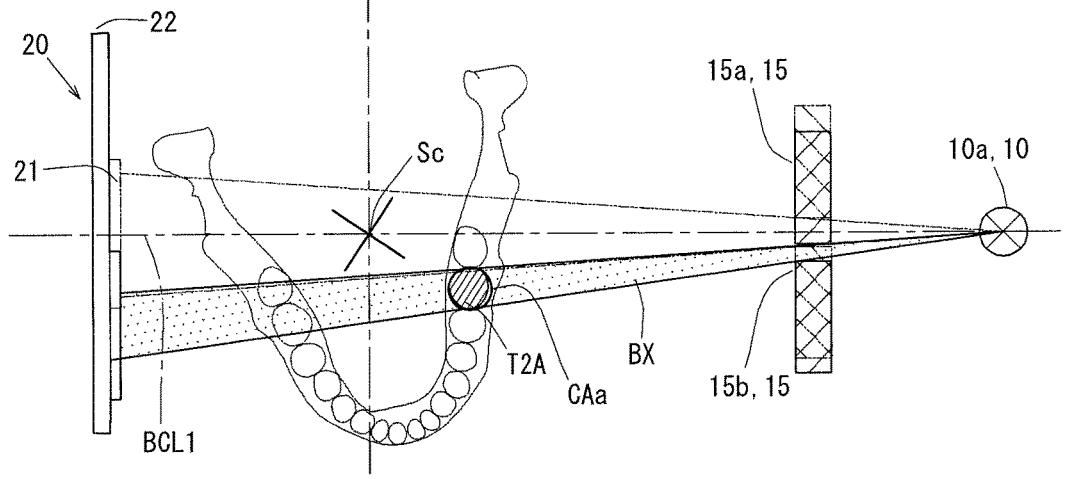
FIGS. 18A and 18B show local X-ray CT imaging at a sixth revolution position.
Figure 18B:
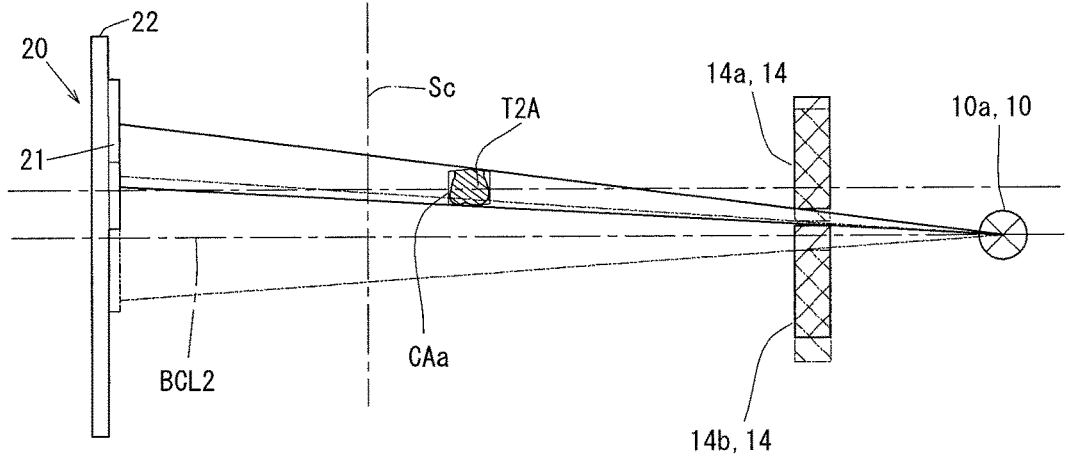

The revolution positions shown in FIG. 9 through FIG. 12 are shown more specifically in FIG. 13 through FIG. 18. In each of FIG. 13 through FIG. 18, (a) is a schematic plan view of the X-ray cone beam BX, and (b) is a schematic side view of the X-ray cone beam BX. FIG. 13 shows the first revolution position, and FIG. 14 shows the second revolution position. FIG. 15 shows the third revolution position, and FIG. 16 shows the fourth revolution position. FIG. 17 shows the fifth revolution position, and FIG. 18 shows the sixth revolution position.

The revolution positions in FIG. 9 through FIG. 12 are merely shown for each of prescribed angles in order to facilitate the explanation of the state of the X-ray CT imaging. The sixth revolution position shown in FIG. 11(b) is symmetrical to the initial position (first position) of the X-ray generation section 10 with respect to the local imaging target OB1.

As shown in FIG. 11, with the revolving arm 30 revolving about the revolution center Sc from the initial position, the X-ray cone beam BX is directed from the X-ray generation section 10 along the y-axis direction. A horizontal direction reference radiation central line BCL1 of the X-ray cone beam BX passes through the revolution center Sc and is directed to the X-ray detection section 20. However, the cylindrical local CT imaging area CAa including the local imaging target OB1 is eccentric with respect to the revolution center Sc. Therefore, the radiation direction in the horizontal direction of the X-ray cone beam BX which is output from the X-ray generation section 10 is adjusted by the beam formation mechanism 13.

A width in the lateral direction of the cylindrical local CT imaging area CAa including the local imaging target OB1 is smaller than that of the X-ray cone beam BX when the expansion thereof in the lateral direction is not restricted. Therefore, the expansion in the lateral direction of the X-ray cone beam BX is adjusted to be small so as to be suitable to the width of the cylindrical local CT imaging area CAa.

This will be described in more detail. The position of the lateral direction blocking plates 15 (15a, 15b) in the lateral direction with respect to the output opening 12 is adjusted respectively by the blocking plate lateral direction moving mechanisms 16b to reduce the expansion in the lateral direction of the X-ray cone beam BX such that the expansion is made suitable to the width of the local CT imaging area CAa. In addition, the opening 17 is shifted rightward with respect to the output opening 12 in the direction from the X-ray generation section 10 to the X-ray detection section 20. Thus, the radiation direction of the X-ray cone beam BX is adjusted to be suitable to the local CT imaging area CAa.

In accordance with the radiation direction of the X-ray cone beam BX adjusted in the lateral direction to be suitable to the local CT imaging area CAa, the X-ray detector 21 of the X-ray detection section 20 is moved by the moving mechanism 23 in the lateral direction with respect to the detector holders 22.

The position of the local CT imaging area CAa with respect to the horizontal direction reference radiation central line BCL1 of the X-ray cone beam BX, directed from the X-ray generation section 10 to the X-ray detection section 20, changes in accordance with the revolution position of the revolving arm 30. Therefore, the position of the lateral direction blocking plates 15 (15a, 15b) in the lateral direction with respect to the output opening 12 is adjusted respectively by the blocking plate lateral direction moving mechanisms 16b in accordance with the revolution position of the revolving arm 30. In addition, the opening 17 is shifted rightward with respect to the output opening 12 in the direction from the X-ray generation section 10 to the X-ray detection section 20. Thus, the radiation direction of the X-ray cone beam BX is adjusted to be suitable to the local CT imaging area CAa.

As shown in FIG. 13, the cylindrical local CT imaging area CAa including the local imaging target OB1, which is the left posterior tooth T2A of the upper jaw, is eccentric in the length direction with respect to a vertical direction reference radiation central line BCL2 of the X-ray cone beam BX which is horizontally directed from the X-ray generation section 10 to the X-ray detection section 20. Therefore, the radiation direction in the vertical direction of the X-ray cone beam BX which is output from the X-ray generation section 10 is adjusted by the beam formation mechanism 13.

A height in the length direction of the cylindrical local CT imaging area CAa including the local imaging target OB1 is smaller than that of the X-ray cone beam BX when the expansion thereof in the length direction is not restricted. Therefore, the expansion in the length direction of the X-ray cone beam BX is adjusted to be small so as to be suitable to the height of the cylindrical local CT imaging area CAa.

This will be described in more detail. The position of the length direction blocking plates 14 (14a, 14b) in the length direction with respect to the output opening 12 is adjusted respectively by the blocking plate length direction moving mechanisms 16a to reduce the expansion in the length direction of the X-ray cone beam BX such that the expansion is made suitable to the height of the local CT imaging area CAa. In addition, the opening 17 is shifted upward with respect to the output opening 12 in the direction from the X-ray generation section 10 to the X-ray detection section 20. Thus, the radiation direction of the X-ray cone beam BX is adjusted to be suitable to the local CT imaging area CAa.

In accordance with the radiation direction of the X-ray cone beam BX adjusted in the length direction to be suitable to the local CT imaging area CAa, the X-ray detector 21 of the X-ray detection section 20 is moved by the moving mechanism 23 in the length direction with respect to the detector holders 22.

The position of the local CT imaging area CAa with respect to the vertical direction reference radiation central line BCL2 of the X-ray cone beam BX, directed from the X-ray generation section 10 to the X-ray detection section 20, changes in accordance with the revolution position of the revolving arm 30. Therefore, the position of the length direction blocking plates 14 (14a, 14b) in the length direction with respect to the output opening 12 is adjusted respectively by the blocking plate length direction moving mechanisms 16a in accordance with the revolution position of the revolving arm 30. In addition, the opening 17 is shifted rightward with respect to the output opening 12 in the direction from the X-ray generation section 10 to the X-ray detection section 20. Thus, the radiation direction of the X-ray cone beam BX is adjusted to be suitable to the local CT imaging area CAa.

As described above, the local CT imaging area CAa is eccentric in the horizontal direction with respect to the revolution center Sc and the horizontal direction reference radiation central line BCL1, and is smaller than the X-ray cone beam BX when the expansion thereof in the lateral direction is not restricted. Thus, the position of the lateral direction blocking plates 15 (15a, 15b) in the lateral direction with respect to the output opening 12 is adjusted respectively by the blocking plate lateral direction moving mechanisms 16b in accordance with the revolution position of the revolving arm 30 to reduce the expansion in the lateral direction of the X-ray cone beam BX such that the expansion is made suitable to the width of the local CT imaging area CAa. In addition, the opening 17 is shifted rightward with respect to the output opening 12 in the direction from the X-ray generation section 10 to the X-ray detection section 20. Thus, the radiation direction of the X-ray cone beam BX is adjusted to be suitable to the local CT imaging area CAa. In this manner, the X-ray cone beam BX can be directed appropriately in the horizontal direction to the local imaging target OB1, which is the area of interest. Thus, the amount of unnecessary exposure to the X-ray can be decreased, and the X-ray CT imaging of the area of interest can be performed with certainty.

The local CT imaging area CAa is eccentric in the vertical direction with respect to the vertical direction reference radiation central line BCL2, and is smaller in height than the X-ray cone beam BX when the expansion thereof in the length direction is not restricted. Thus, the position of the length direction blocking plates 14 (14a, 14b) in the length direction with respect to the output opening 12 is adjusted respectively by the blocking plate length direction moving mechanisms 16a in accordance with the revolution position of the revolving arm 30 to reduce the expansion in the length direction of the X-ray cone beam BX such that the expansion is made suitable to the height of the local CT imaging area CAa. In addition, the opening 17 is shifted upward with respect to the output opening 12 in the direction from the X-ray generation section 10 to the X-ray detection section 20. Thus, the radiation direction of the X-ray cone beam BX is adjusted to be suitable to the local CT imaging area CAa. In this manner, the X-ray cone beam BX can be directed appropriately in the vertical direction to the local imaging target OB1, which is the area of interest. Thus, the amount of unnecessary exposure to the X-ray can be decreased, and the X-ray CT imaging of the area of interest can be performed with certainty.

The position of the opening 17 is changed in accordance with the position of the local CT imaging area CAa, which is in accordance with the position of the revolution position, as specifically shown in (b) in each of FIG. 13 through FIG. 18.

At the first revolution position, the opening 17 is eccentric upward, and the eccentricity angle is larger than that at the second revolution position (see FIG. 13). At the second revolution position, the opening 17 is eccentric upward, and the eccentricity angle is smaller than that at the first revolution position (see FIG. 14).

The eccentricity angle is the angle of the center beam of the X-ray cone beam BX with respect to the vertical direction reference radiation central line BCL2.

At the third revolution position, the opening 17 is eccentric upward, and the eccentricity angle is approximately equal to that at the first revolution position (see FIG. 15). At the fourth revolution position, the opening 17 is eccentric upward, and the eccentricity angle is larger than that at the first revolution position (see FIG. 16).

At the fifth revolution position, the opening 17 is eccentric upward, and the eccentricity angle is larger than that at the fourth revolution position (see FIG. 17). At the sixth revolution position, the opening 17 is eccentric upward, and the eccentricity angle is approximately equal to that at the fifth revolution position (see FIG. 18).

Regarding the first through sixth revolution positions, a line segment FC1 (not shown) connecting the center of the local CT imaging area CAa and the X-ray tube focal point of the X-ray generator 10a as seen in the x-axis direction is assumed. In this case, as variable angle θ1 made by the vertical direction reference radiation central line BCL2 and the line segment FC1 has a larger absolute value, the degree of eccentricity is larger.

The position of the opening 17 is changed in accordance with the position of the local CT imaging area CAa, which is in accordance with the position of the revolution position, as specifically shown in (a) in each of FIG. 13 through FIG. 18.

At the first revolution position, the opening 17 is eccentric rightward when seen in the direction from the X-ray generation section 10 to the X-ray detection section 20 (see FIG. 13). At the second revolution position, the opening 17 is eccentric leftward when seen in the direction from the X-ray generation section 10 to the X-ray detection section 20 (see FIG. 14).

The eccentricity angle is the angle of the center beam of the X-ray cone beam BX with respect to the horizontal direction reference radiation central line BCL1.

At the third revolution position, the opening 17 is eccentric further leftward than at the second revolution position when seen in the direction from the X-ray generation section 10 to the X-ray detection section 20 (see FIG. 15). At the fourth revolution position, the opening 17 is eccentric further leftward than at the third revolution position when seen in the direction from the X-ray generation section 10 to the X-ray detection section 20 (see FIG. 16).

At the fifth revolution position, the opening 17 is eccentric leftward when seen in the direction from the X-ray generation section 10 to the X-ray detection section 20, but is back rightward from the position at the fourth revolution position (see FIG. 17). At the sixth revolution position, the opening 17 is eccentric leftward when seen in the direction from the X-ray generation section 10 to the X-ray detection section 20, but is back rightward from the position at the fifth revolution position (see FIG. 18).

Regarding the first through sixth revolution positions, a line segment FC2 (not shown) connecting the center of the local CT imaging area CAa and the X-ray tube focal point of the X-ray generator 10a as seen in the z-axis direction is assumed. In this case, as variable angle θ2 made by the vertical direction reference radiation central line BCL2 and the line segment FC2 has a larger absolute value, the degree of eccentricity is larger.

The expansion of the opening 17 in the length direction is changed in accordance with the position of the local CT imaging area CAa, which is in accordance with the position of the revolution position, as specifically shown in (b) in each of FIG. 13 through FIG. 18.

At the first revolution position, the expansion of the opening 17 is smaller than that at the second revolution position (see FIG. 13). At the second revolution position, the expansion of the opening 17 is larger than that at the first revolution position (see FIG. 14).

At the third revolution position, the expansion of the opening 17 is still larger than that at the second revolution position (see FIG. 15). At the fourth revolution position, the expansion of the opening 17 is still larger than that at the third revolution position (see FIG. 16).

At the fifth revolution position, the expansion of the opening 17 is still larger than that at the fourth revolution position (see FIG. 17). At the sixth revolution position, the expansion of the opening 17 is approximately equal to that at the fifth revolution position (see FIG. 18).

Regarding the first through sixth revolution positions, as seen in the x-axis direction, as the distance between the center of the local CT imaging area CAa and the X-ray tube focal point of the X-ray generator 10a is shorter, the degree of expansion of the opening 17 is larger, or as the distance between the edge of the local CT imaging area CAa on the X-ray generator 10a side and the X-ray tube focal point of the X-ray generator 10a is shorter, the degree of expansion of the opening 17 is larger.

As shown in (a) in each of FIG. 13 through FIG. 18, the expansion in the lateral direction of the opening 17 changes as specifically described below as the position of the local CT imaging area CAa changes in accordance with the revolution position.

The expansion of the opening 17 at the first revolution position is slightly larger than that at the second revolution position (see FIG. 13), and the expansion of the opening 17 at the second revolution position is slightly smaller than that at the first revolution position (see FIG. 14).

The expansion of the opening 17 at the third revolution position is approximately equal to that at the first revolution position (see FIG. 15), and the expansion of the opening 17 at the fourth revolution position is larger than that at the third revolution position (see FIG. 16).

The expansion of the opening 17 at the fifth revolution position is still larger than that at the fourth revolution position (see FIG. 17), and the expansion of the opening 17 at the sixth revolution position is approximately equal to that at the fifth revolution position (see FIG. 18).

Regarding the first through sixth revolution positions, as seen in the z-axis direction, as the distance between the center of the local CT imaging area CAa and the X-ray tube focal point of the X-ray generator 10a is shorter, the degree of expansion of the opening 17 is larger, or as the distance between the edge of the local CT imaging area CAa on the X-ray generator 10a side and the X-ray tube focal point of the X-ray generator 10a is shorter, the degree of expansion of the opening 17 is larger.

The X-ray detector 21 of the X-ray detection section 20 is moved in the length direction and the lateral direction with respect to the detector holders 22 by the moving mechanisms 23 in accordance with the radiation direction of the X-ray cone beam BX, which is adjusted in the length direction and the lateral direction to be suitable to the local CT imaging area CAa. Thus, even the X-ray detector 21, which is made compact, can project the X-ray cone beam BX on the detection plane 21a and can perform X-ray CT imaging of the area of interest with certainty.

Owing to the moving mechanisms 23, the X-ray detector 21 having a relatively small detection plane 21a can be used, and thus the cost of the device can be reduced. Needless to say, the X-ray detector 21 having a large detection plane 21a is usable. The X-ray detection section 20 may include the X-ray detector 21 having a detection plane 21a which is sufficiently large to receive all of the X-ray cone beam BX and the X-ray slit beam BXP without moving, so that the moving mechanisms 23 can be omitted. In this case, the X-ray detector 21 may cost high. However, since the moving mechanisms 23 can be omitted, the load on the movement control and the cost of the device can be suppressed low.

Now, with respect to FIG. 19 through FIG. 24, a form in which X-ray CT imaging of an imaging target OB2 is performed by the X-ray CT imaging device 1 will be described. The imaging target OB2 is the entirety of the dental arch including the anterior teeth T1, the left posterior teeth T2, and the right posterior teeth T3.

Figure 19:
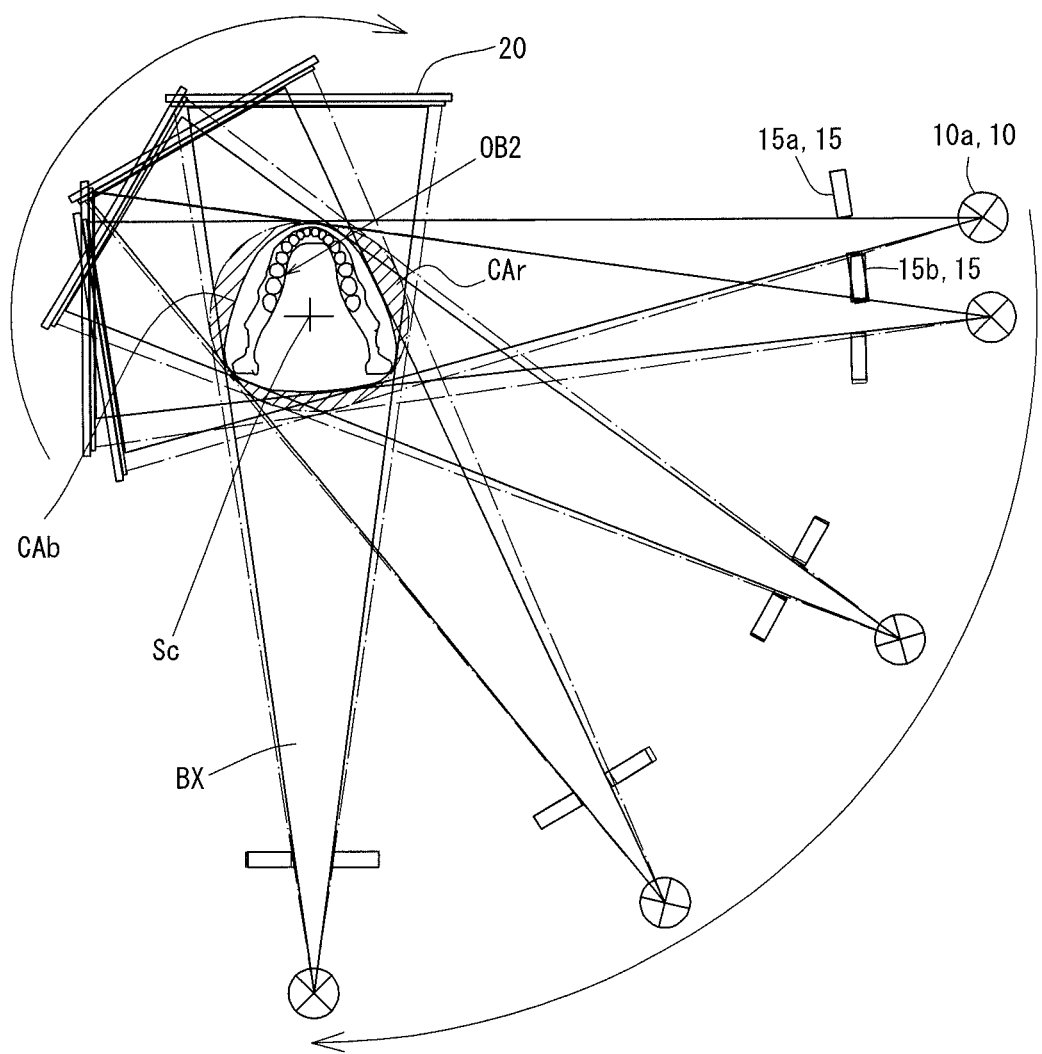
FIG. 19 is a schematic plan view showing a locus of X-ray CT imaging of imaging an imaging target.
Figure 20:
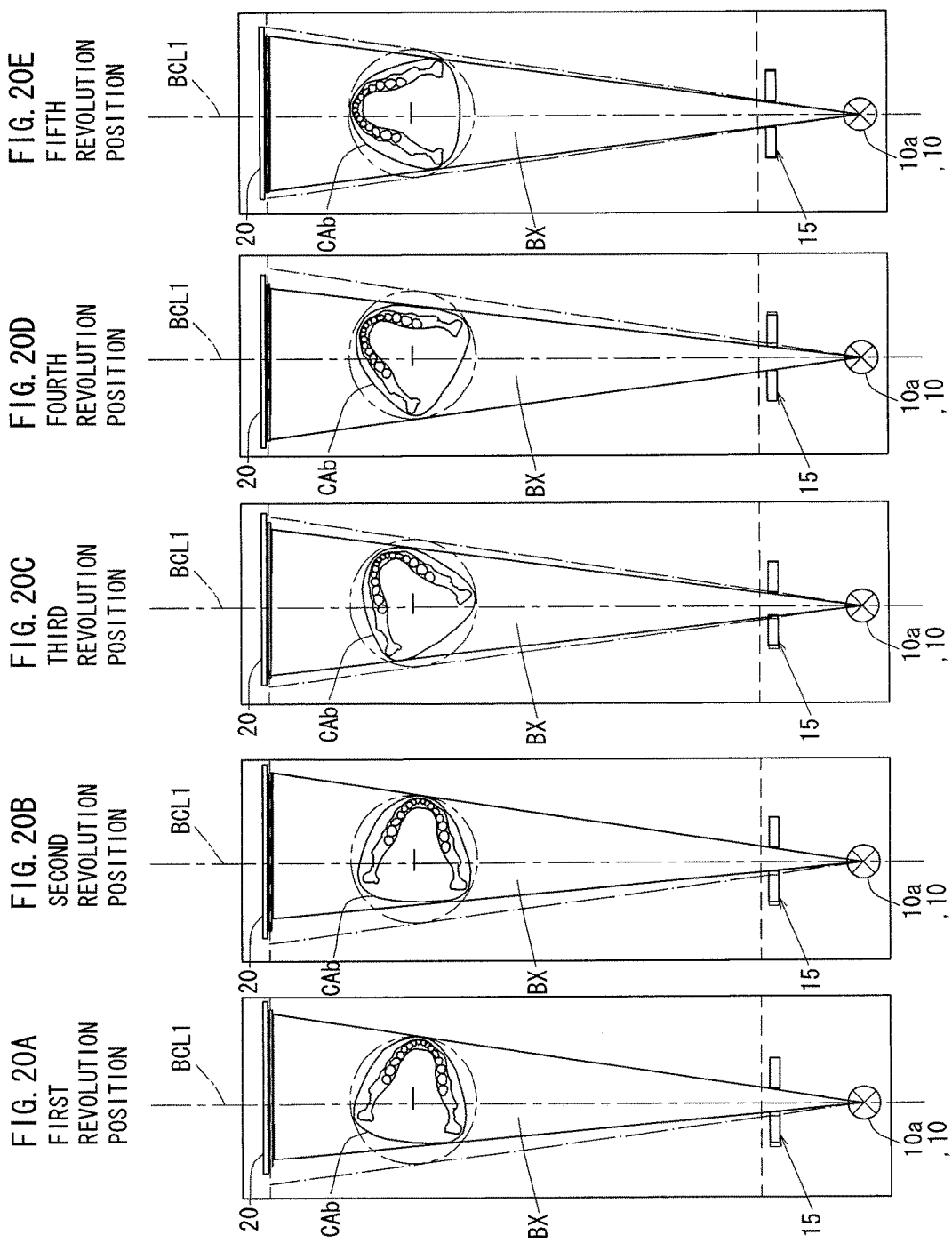
FIGS. 20A-20E show X-ray CT imaging of imaging an imaging target.
Figure 21:
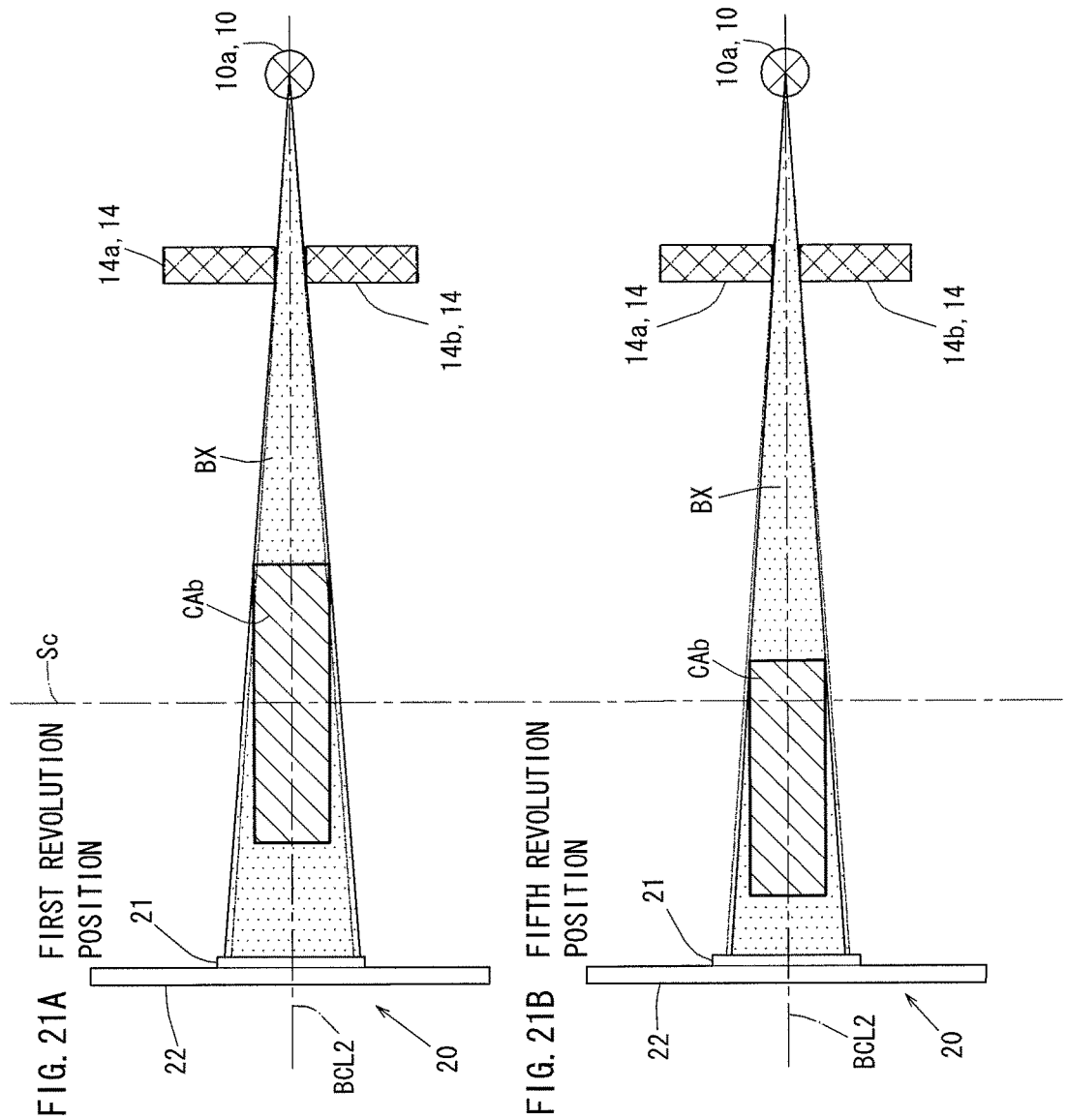
FIGS. 21A and 21B show an X-ray cone beam restricted regarding a length direction radiation range with respect to the imaging target.
Figure 22:
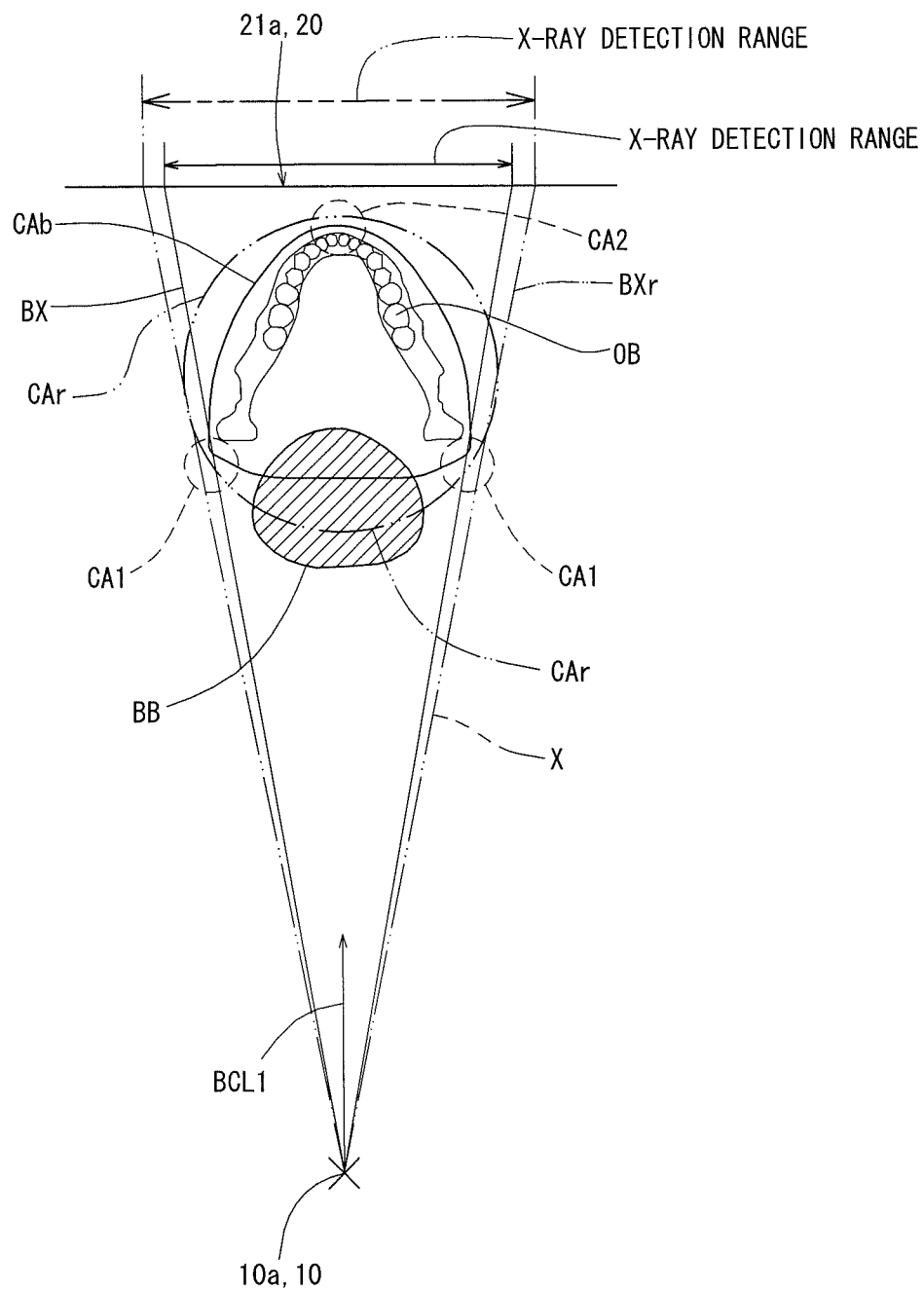
FIG. 22 is a plan view showing, in comparison, a case where the CT imaging area is a cylindrical CT imaging area having a circular cross-section and a case where the CT imaging area is a triangular CT imaging area.

FIG. 19 is a schematic plan view showing a locus of X-ray CT imaging of the imaging target OB2. FIG. 20 shows the X-ray CT imaging of the imaging target OB2. FIG. 21 shows the X-ray cone beam BX directed to the imaging target OB2, which is restricted in the length direction regarding the radiation range. FIG. 22 is a plan view showing, in comparison, a case where the CT imaging area is a cylindrical CT imaging area CAr having a circular cross-section and a case where the CT imaging area is a triangular CT imaging area CAb. FIG. 23 shows adjustment of the X-ray amount directed to the subject during the X-ray CT imaging. FIG. 24 shows CT imaging areas which are generally triangular as seen in a plan view.

In more detail, FIG. 20(a) through FIG. 20(e) are each a schematic plan view showing the radiation range and the radiation direction of the X-ray cone beam BX at each revolution position. FIG. 21(a) is a schematic view, as seen in the x-axis direction, of the X-ray cone beam which is restricted in the length direction regarding the radiation range at the first revolution position. Similarly, FIG. 21(b) is a schematic view, as seen in the x-axis direction, of the X-ray cone beam which is restricted in the length direction regarding the radiation range at the fifth position.

FIG. 20(a) shows a state where the position of the revolving arm 30 is controlled such that the X-ray generation section 10 is located to the right of the head of the human body and the X-ray detection section 20 located to the left of the head of the human body. FIG. 20(e) shows a state where the X-ray generation section 10 has revolved by 90° from the state in FIG. 20(a) to a position rear to the head. FIG. 20(b) through FIG. 20(d) show different revolution positions during the revolution.

FIG. 23 provides graphs showing the X-ray output and the revolution speed of the revolving arm 30 regarding the adjustment of the X-ray amount directed to the subject at the first revolution position, the third revolution position and the fifth revolution position. FIG. 24 provides schematic views showing CT imaging areas having various generally triangular shapes as seen in a plan view.

In the following description, the imaging target OB2 is the entirety of the dental arch including the anterior teeth T1, the left posterior teeth T2, and the right posterior teeth T3. Therefore, the area of interest is of a prism shape which is generally triangular as seen in a plan view. The X-ray CT imaging is performed on the triangular CT imaging area CAb of the triangular prism shape. The generally triangular prism of the triangular CT imaging area CAb has a cross-section which is generally isosceles triangular as shown in FIG. 22. The generally isosceles triangular cross-section has protrusions CA1 at both of left and right ends of the base side and an apex CA2.

In other words, the generally triangular cross-section of the triangular CT imaging area CAb has the shape of the Reuleaux triangle, or has a generally triangular shape close to the Reuleaux triangle which is obtained as a result of rounding the apexes of the Reuleaux triangle or as a result of slightly deforming the Reuleaux triangle.

First, the X-ray CT imaging of the imaging target OB2 is performed as follows. In the state where the subject M1 is at a prescribed position in the X-ray CT imaging device 1 (see FIG. 1), the revolving arm 30 is at the initial position (first revolution position) where the X-ray generation section 10 is on the side of the right posterior teeth T3 and the X-ray detection section 20 is on the side of the left posterior teeth T2. As shown in FIG. 12, the X-ray CT imaging is performed with the revolving arm 30 being revolved from the initial position by 180 degrees or more about the revolution shaft 31 as the revolution center Sc.

In this case, unlike in the case of the local CT imaging area CAa which includes the local imaging target OB1 and is eccentric with respect to the revolution center Sc, the revolution center Sc is in the vicinity of the gravitational center in the horizontal direction of the triangular CT image area CAb of the triangular prism shape (generally triangular prism shape) including the imaging target OB2. However, the width in the lateral direction of the general triangular shape as seen in a plan view of the triangular CT imaging area CAb, and the relative position of the triangular CT imaging area CAb with respect to each of the left and right edges of the triangular CT imaging area CAb and with respect to the revolution center Sc, change in accordance with the revolution position. Therefore, the position of the lateral direction blocking plates 15 (15a, 15b) in the lateral direction with respect to the output opening 12 is adjusted respectively by the blocking plate lateral direction moving mechanisms 16b to adjust the expansion in the lateral direction of the X-ray cone beam BX such that the expansion is made suitable to the width of the triangular CT imaging area CAb. In addition, the opening 17 is shifted with respect to the output opening 12 in the lateral direction when seen in the direction from the X-ray generation section 10 to the X-ray detection section 20. Thus, the radiation direction of the X-ray cone beam BX is adjusted to be suitable to the triangular CT imaging area CAb.

In accordance with the radiation direction of the X-ray cone beam BX adjusted in the lateral direction to be suitable to the triangular CT imaging area CAb, the X-ray detector 21 of the X-ray detection section 20 is moved in the lateral direction by the moving mechanism 23 in accordance with the detector holders 22.

The triangular CT imaging area CAb is of a triangular prism and thus has a uniform height. However, as shown in FIG. 21, the distance from the revolution center Sc to the edge of the triangular CT imaging area CAb on the X-ray generation section 10 side is changed in accordance with the revolution position. Therefore, the expansion in the length direction of the X-ray cone beam BX which is output from the X-ray generation section 10 is adjusted by the beam formation mechanism 13 to be suitable to the height of the edge of the triangular CT imaging area CAb on the X-ray generation section 10 side.

This will be described in more detail. The position of the length direction blocking plates 14 (14a, 14b) in the length direction with respect to the output opening 12 is adjusted respectively by the blocking plate length direction moving mechanisms 16a to adjust the expansion in the length direction of the X-ray cone beam BX to be suitable to the height of the edge of the triangular CT imaging area CAb on the X-ray generation section 10 side.

This will be described more specifically. The edge of the triangular CT imaging area CAb on the X-ray generation section 10 side shown in FIG. 21(a) is closer to the X-ray generator 10a than the edge of the triangular CT imaging area CAb on the X-ray generation section 10 side shown in FIG. 21(b). Therefore, the expansion in the length direction of the X-ray cone beam BX in FIG. 21(a) is made larger than that in FIG. 21(b).

Namely, the expansion in the length direction of the X-ray cone beam BX is controlled to become larger when the triangular CT imaging area CAb approaches the X-ray generation section 10, and is controlled to become smaller when the triangular CT imaging area CAb is distanced from the X-ray generation section 10.

As described above, the width in the lateral direction, and the relative position with respect to the revolution center Sc, of the triangular CT imaging area CAb having a triangular shape as seen in a plan view are changed in accordance with the revolution position. Thus, the position of the lateral direction blocking plates 15 (15a, 15b) in the lateral direction with respect to the output opening 12 is adjusted respectively by the blocking plate lateral direction moving mechanisms 16b to adjust the expansion in the lateral direction of the X-ray cone beam BX such that the expansion is made suitable to the width of the triangular CT imaging area CAb. In addition, the opening 17 is shifted with respect to the output opening 12 in the lateral direction when seen in the direction from the X-ray generation section 10 to the X-ray detection section 20. Thus, the radiation direction of the X-ray cone beam BX is adjusted to be suitable to the triangular CT imaging area CAb. In this manner, the X-ray cone beam BX can be directed appropriately in the horizontal direction to the imaging target OB2, which is the area of interest. Thus, the amount of unnecessary exposure to the X-ray can be decreased, and the X-ray CT imaging of the area of interest can be performed with certainty.

This will be described in more detail. FIG. 22 is a plan view showing, in comparison, a case where the CT imaging area CA is circular and a case where CT imaging area CA is generally triangular. As shown in FIG. 22, in the case where the CT imaging area CA is a cylindrical CT imaging area CAr having a circular cross-section which includes the entire area of the interest including the entire imaging target OB, an X-ray cone beam BXr directed to the cylindrical CT imaging area CAr has a larger radiation range than the X-ray cone beam BX directed to the triangular CT imaging area CAb.

Therefore, in the case where the triangular CT imaging area CAb of the triangular prism shape is set as the CT imaging area, as compared with the case where the cylindrical CT imaging area CAr having a circular cross-section is set as the CT imaging area, a range of the X-ray detected by the X-ray detector 21 is smaller as shown in FIG. 22. In this manner, according to this embodiment, the detection plane of the X-ray detector 21 can be made smaller, and thus the cost of the device can be suppressed low.

As shown in FIG. 22, in the case where the triangular CT imaging area CAb of the triangular prism shape is set as the CT imaging area, an area which is inside the circle of the cylindrical CT imaging area CAr and is outside the general triangle of the triangular CT imaging area CAb is not irradiated with the X-ray unnecessarily. Thus, the amount of exposure can be reduced.

As shown in FIG. 22, the cervical vertebra BB is located rearward to the jawbone. Since the triangular CT imaging area CAb is generally triangular, the base side of the generally triangle is inside the circle of the cylindrical CT imaging area CAr. Thus, it is seen that the amount of exposure to the X-ray of the area of the cervical vertebra BB can be decreased.

As is clear from a comparison between the X-ray cone beams BX and BXJ, in the case where the triangular CT imaging area CAb of the triangular prism shape is set as the CT imaging area CA, as compared with the case where the cylindrical CT imaging area CAr having a circular cross-section is set as the CT imaging area CA, the radiation range of the X-ray can be reduced.

As seen from the above, regarding the jawbone including the dental arch, which is the imaging target OB2, the following occurs in the case where the generally triangular CT imaging area CAb is set as the CT imaging area CA. The left and right temporomandibular joints are accommodated in the vicinity of the left and right protrusions CA1, the anterior teeth are accommodated in the vicinity of the apex CA2, and the curved jawbone is accommodated along a curved line extending from each of the left and right protrusions CA1 to the apex CA2 so as to project upward. By contrast, in the case where the cylindrical CT imaging area CAr having a circular cross-section is set as the CT imaging area CA, as compared with the case where the generally triangular CT imaging area CAb is set as the CT imaging area CA, the area of the CT imaging area CA outside the jawbone is larger. Therefore, in the case where the CT imaging area CA is the generally triangular CT imaging area CAb, the amount of the X-ray directed to an area other than the imaging target OB can be decreased, and thus the amount of exposure to the X-ray can be decreased for the subject.

FIG. 23 shows how the X-ray amount directed to the subject is adjusted. As shown in FIG. 23, the X-ray amount is adjusted or controlled in accordance with the revolution position. Therefore, even when there is a site in which the X-ray amount is relatively large, CT imaging can be performed with the influence thereof being alleviated. Thus, a satisfactory CT image can be acquired.

FIG. 23(a) through FIG. 23(c) are each a plan view showing the positional relationship between the X-ray cone beam BX which is output when the revolving arm 30 is at each of the first revolution position, the second revolution position and the third revolution position, and the cervical vertebra BB in the body of the subject.

The first through third revolution positions shown in FIG. 23(a) through FIG. 23(c) do not directly correspond to the first through third revolution positions shown in FIG. 20(a) through FIG. 20(c).

FIG. 23(d) is a graph plotting the intensity of the X-ray output. The vertical axis represents the intensity of the X-ray output, whereas the horizontal axis represents the revolution position. FIG. 23(e) is a graph plotting the revolution speed of the X-ray cone beam BX. The vertical axis represents the revolution speed, whereas the horizontal axis represents the revolution position. The distance in the horizontal direction between the dental arch and the cervical vertebra of the human body is not actually as far as shown in FIG. 23. For easier understanding, the distance in the horizontal direction between the dental arch and the cervical vertebra is shown large.

In the case where the imaging target OB is the jawbone including the dental arch, the cervical vertebra BB, which is a site absorbing the X-ray, is behind the jawbone in the body of the subject. Regarding CT imaging, when there are a state where the X-ray reaches the imaging target OB2 after passing through such an X-ray absorbing site and also a state where the X-ray reaches the imaging target OB2 without passing through such an X-ray absorbing site, it is preferable to control the X-ray amount.

For example, in the state where the X-ray generation section 10 is at each of the first revolution position and the third revolution position as shown in FIG. 23(a) and FIG. 23(c), the cervical vertebra BB, which is likely to absorb the X-ray, is not contained in the radiation area of the X-ray cone beam BX. Therefore, even when the X-ray amount is relatively small, good projection data can be acquired on the triangular CT imaging area CAb. However, in the state where the X-ray generation section 10 is at the second revolution position (behind the subject) as shown in FIG. 23(b), the cervical vertebra BB is contained in the radiation area of the X-ray cone beam BX. Therefore, the X-ray reaches the triangular CT imaging area CAb after passing through the cervical vertebra BB. In order to acquire good projection data on the triangular CT imaging area CAb, it is preferable to direct the X-ray of a relative large amount.

In order to change the X-ray amount in accordance with the positional relationship between the X-ray cone beam BX and an X-ray absorbing site such as the cervical vertebra BB or the like, namely, in accordance with the revolution position of the revolving arm 30, it is preferable in this embodiment that at least one of the X-ray output and the revolution speed is adjusted as shown in FIG. 23(d) or FIG. 23(e).

In the case where, for example, the X-ray output is adjusted, as shown in FIG. 23(d), the X-ray amount output from the X-ray generation section 10 is controlled to become larger in the state of FIG. 23(b) than in the state of FIG. 23(a) or FIG. 23(c). In the case where the revolution speed is adjusted, as shown in FIG. 23(e), the revolution speed (revolution speed of the revolving arm 30) is controlled to be lower, so that the X-ray amount directed to the triangular CT imaging area CAb is larger, in the state of FIG. 23(b) than in the state of FIG. 23(a) or FIG. 23(c).

Owing to such control, even when there is a site having a relatively high X-ray absorbability, CT imaging can be performed with the influence thereof being alleviated. Thus, a satisfactory CT image can be acquired.

The triangular CT imaging area CAb has a uniform height in the vertical direction, but the distance from the revolution center Sc to the edge of the triangular CT imaging area CAb on the X-ray generation section 10 side is changed in accordance with the revolution position. The expansion in the length direction of the X-ray cone beam BX which is output from the X-ray generation section 10 is adjusted by the beam formation mechanism 13 to be suitable to the height of the edge of the triangular CT imaging area CAb on the X-ray generation section 10 side in accordance with the revolution position. Owing to this, the X-ray cone beam BX can be directed appropriately in the vertical direction to the imaging target OB2, which is the area of interest. Thus, the amount of unnecessary exposure to the X-ray can be decreased, and the X-ray CT imaging of the area of interest can be performed with certainty.

In accordance with the radiation direction of the X-ray cone beam which is adjusted in the lateral direction to be suitable to the triangular CT imaging area CAb, the X-ray detector 21 of the X-ray detection section 20 is moved in the length direction and the lateral direction by the moving mechanism 23 with respect to the detection holders 22. Thus, even the X-ray detector 21, which is made compact, can project the X-ray cone beam BX on the detection plane 21a and can perform X-ray CT imaging of the area of interest with certainty.

In the above description, the triangular CT imaging area CAb has a triangular prism shape which is generally triangular as seen in a plan view. As shown in, for example, FIG. 24, the triangular CT imaging area may have any of various generally triangular shapes as seen in a plan view.

In more detail, the triangular CT imaging area CAb may have a shape as shown in each of FIG. 24(a) through FIG. 24(g), which are provided as examples which are explained with reference to triangle ABC shown in FIG. 24(f).

First, triangle ABC shown in FIG. 24(f) will be described. Triangle ABC shown in FIG. 24(f) is formed of apexes A, B and C, and lines AB, AC and BC connecting the apexes A, B and C.

In the example shown here, side BC is the bottom side, and apex A made by contact of sides AB and AC faces bottom side BC.

Side AB is formed of line ABa in an area in the vicinity of apex A, line ABb in an area in the vicinity of apex B, and line AB1 in a center area far from apexes A and B.

Side AC is formed of line ACa in an area in the vicinity of apex A, line ACb in an area in the vicinity of apex C, and line AC1 in a center area far from apexes A and C.

Side BC is formed of line BCa in an area in the vicinity of apex B, line BCb in an area in the vicinity of apex C, and line BC1 in a center area far from apexes B and C.

Apexes A, B and C may be defined arbitrarily, but are basically set to be located such that the dental arch as seen in a plan view is accommodated in an area enclosed by sides AB, AC and BC.

Specifically, the anterior teeth T1 are accommodated in the vicinity of apex A, the left posterior teeth T2 are accommodated in the vicinity of apex B, and the right posterior teeth T3 are accommodated in the vicinity of apex C.

Since the dental arch is bilaterally symmetrical, triangle ABC may be an isosceles triangle or specifically a regular triangle.

In summary, the triangular CT imaging area CAb may have any of various shapes which conform to the idea that the entirety of the dental arch including the anterior teeth T1 and the left and right posterior teeth T2 and T3 are accommodated with no waste.

First, FIG. 24(a) shows a CT imaging area CA having the shape of triangle ABC formed of apexes A, B and C and sides AB, AC and BC. In order to describe the example of FIG. 24(a) in more detail, FIG. 24(f) is referred to. The CT imaging area CA in the example of FIG. 24(a) has the shape of triangle ABC formed of apexes A, B and C and sides AB, AC and BC in FIG. 24(f). In the example shown here, side BC is the bottom side. Apex A formed by a contact of sides AB and AC faces bottom side BC. Triangle ABC is preferably an isosceles triangle. Needless to say, triangle ABC may an equilateral triangle. Like the protrusions CA1 shown in FIG. 22, protrusions CA1x are located in the vicinity of apexes B and C.

FIG. 24(b) shows a CT imaging area CA in another example. The shape of the CT imaging area CA in this example is partially different from the shape of the CT imaging area CA in FIG. 24(a). Specifically, whereas apex A of triangle ABC in FIG. 24(a) is pierced, the corresponding part in FIG. 24(b) is rounded. Namely, in the CT imaging area CA in FIG. 24(b), sides AB and AC are not connected to each other by apex A, but by a curved line convexed outward.

The line connecting sides AB and AC to each other is not limited to a curved line, and may be a straight line (in this case, the CT imaging area CA is trapezoidal) or a partially straight line. Such a straight line may be a single straight line or formed of a plurality of straight lines.

In order to describe the example of FIG. 24(b) in more detail, FIG. 24(f) is referred to. The CT imaging area CA in the example of FIG. 24(b) has a shape enclosed by bottom side BC, line ABb, line AB1, line AR, line AC1 and line ACb in FIG. 24(f). Side AB is formed of line ABa of an area close to apex A, line ABb of an area close to apex B, and line AB1 of an area far from apexes A and B. Side AC is formed of line ACa of an area close to apex A, line ACb of an area close to apex C, and line AC1 of an area far from apexes A and C. Line AB1 and line AC1 are connected to each other by line AR, which is preferably inside triangle ABC and thus is inner to apex A. In the example shown here, line AB1 and line AC1 are connected to each other by arc AR. Arc AR has a convexed side and a concaved side. In this example, the convexed side of arc AR is directed outward with respect to triangle ABC. Namely, arc AR is convexed outward.

FIG. 24(c) shows a CT imaging area CA in still another example. The shape of the CT imaging area CA in this example is partially different from the shape of the CT imaging area CA in FIG. 24(b). Specifically, whereas apexes B and C of the triangle, namely, both of left and right ends of bottom side BC in FIG. 24(b), are pierced, the corresponding parts in FIG. 24(c) are rounded. Namely, in the CT imaging area CA in FIG. 24(c), sides AB and BC are not connected to each other by apex B but by a curved line convexed outward, and sides AC and BC are not connected to each other by apex C but by a curved line convexed outward, while straight lines AB1 and AC1 are left.

The line connecting sides AB and BC to each other and the line connecting sides AC and BC to each other are not each limited to a curved line, and may be a straight line or a partially straight line. Such a straight line may be a single straight line or formed of a plurality of straight lines.

In order to describe the example of FIG. 24(c) in more detail, FIG. 24(f) is referred to. The CT imaging area CA in the example of FIG. 24(c) has a shape enclosed by line BC1, line BR, line AB1, line AR, line AC1, and line CR in FIG. 24(f). Side BC is formed of line BCa of an area close to apex B, line BCb of an area close to apex C, and line BC1 of an area far from apexes B and C. Side AC is formed of line ACa of an area close to apex A, line ACb of an area close to apex C, and line AC1 of an area far from apexes A and C. Line AB is substantially the same as those in FIG. 24(b) and will not be described in detail.

Line AB1 and line BC1 are connected to each other by line BR, which is preferably inside triangle ABC and thus is inner to apex B. Line AC1 and line BC1 are connected to each other by line CR, which is preferably inside triangle ABC and thus is inner to apex C. In the example shown here, line AB1 and line BC1 are connected to each other by arc BR, and line AC1 and line BC1 are connected to each other by arc CR. Arcs BR and CR each have a convexed side and a concaved side. In this example, the convexed side of arc BR and the convexed side of arc CR are directed outward with respect to triangle ABC. Namely, arcs BR and CR are convexed outward.

FIG. 24(d) shows a CT imaging area CA in still another example. The shape of the CT imaging area CA in this example is partially different from the shape of the CT imaging area CA in FIG. 24(c). Specifically, whereas lines AB1 and AC1 in FIG. 24(c) are straight lines, the corresponding parts in FIG. 24(d) are deformed to be curved lines convexed outward.

Such deformed lines AB1 and AC1 are not each limited to a curved line, and may be a partially straight line. Such a straight line may be a single straight line or formed of a plurality of straight lines.

In order to describe the example of FIG. 24(d) in more detail, FIG. 24(f) is referred to. The CT imaging area CA in the example of FIG. 24(d) has a shape enclosed by line BC1, line BR, line ABR, line AR, line ACR, and line CR in FIG. 24(f). As compared with the example in FIG. 24(c), lines AB1 and AC1 are replaced with lines ABR and ACR. The other elements are substantially the same as those in FIG. 24(c) and will not be described in more detail.

As compared with the example in FIG. 24(c), lines AB1 and AC1 are replaced with lines ABR and ACR, which are outside triangle ABC. In the example shown here, lines ABR and ACR are arcs. Arcs ABR and ACR each have a convexed side and a concaved side. In this example, the convexed side of arc ABR and the convexed side of arc ACR are directed outward with respect to triangle ABC. Namely, arcs ABR and ACR are convexed outward.

Namely, line ABR is a curved line connecting both of two ends of line AB1 with an arcked line convexed outward, and line ACR is a curved line connecting both of two ends of line AC1 with an arcked line convexed outward.

Arcs ABR and ACR may be each deformed to be a straight line convexed outward which is formed of a plurality of straight lines.

As long as the imaging target OB2 is accommodated in the CT imaging area CA efficiently, arcs BR, ABR, AR, ACR and CR may have substantially the same curvature, so that a generally semicircle shape, encompassing a semicircle, is formed. Herein, the term "generally semicircle shape" is not limited to a semicircle of a perfect circle, and may encompass a semicircle including an arc portion having a partially different curvature or a horseshoe shape.

Preferably, arcs BR, ABR, AR, ACR and CR are connected smoothly with no inflection point. In this case, the CT imaging area CA is generally half-moon-shaped as shown in FIG. 24(g).

FIG. 24(e) shows a CT imaging area CA in still another example. The shape of the CT imaging area CA in this example is partially different from the shape of the CT imaging area CA in FIG. 24(d). Specifically, whereas side BC in FIG. 24(d) is a straight line, the corresponding part in FIG. 24(e) is deformed to be a curved line convexed outward. Such deformed side BC is not limited to a curved line, and may be a partially straight line. Such a straight line may be a single straight line or formed of a plurality of straight lines.

In order to describe the example of FIG. 24(e) in more detail, FIG. 24(f) is referred to. The CT imaging area CA in the example of FIG. 24(e) has a shape enclosed by lines BCR, BR, ABR, AR, ACR and CR in FIG. 24(f). As compared with the example in FIG. 24(d), line BC1 is replaced with line BCR. The other elements are substantially the same as those in FIG. 24(d) and will not be described in more detail.

As compared with the example in FIG. 24(d), line BC1 is replaced with line BCR, which is outside triangle ABC. Line BCR is the bottom side of general triangle ABC. In the example shown here, line BCR is an arc. Arc BCR has a convexed side and a concaved side. In this example, the convexed side of arc BCR is directed outward with respect to triangle ABC. Namely, arc BCR is convexed outward.

The line BCR is a curved line connecting both of two ends of line BC1 with an arcked line convexed outward. Arc BCR may be deformed to be a straight line convexed outward which is formed of a plurality of straight lines.

As long as the imaging target OB2 is accommodated in the CT imaging area CA efficiently, arcs BR, ABR, AR, ACR and CR may have substantially the same curvature, so that a generally semicircle shape, encompassing a semicircle, is formed. Herein, the term "generally semicircle shape" is not limited to a semicircle of a perfect circle, and may encompass a semicircle including an arc portion having a partially different curvature or a horseshoe shape.

Preferably, arcs BR, ABR, AR, ACR and CR are connected smoothly with no inflection point. In this case, the CT imaging area CA is generally shaped like a half moon (strictly, shaped like a moon of the thirteenth night).

In any of FIG. 24(a) through FIG. 24(g), the CT imaging area CA includes protrusions CA1x like the protrusions CA1 in FIG. 22. The CT imaging area CA in each of FIG. 24(d) and FIG. 24(e) includes the protrusions CA1x at both of left and right ends of side BC or line BCR, which is the lower side, namely, the bottom side. In such a generally triangular shape, the left and right protrusions CA1x are each connected to an area in the vicinity of apex A by curved lines ABR and ACR. Such a generally triangular shape is bilaterally symmetrical.

Needless to say, it is sufficient that the imaging target OB2 is accommodated in the CT imaging area CA efficiently and appropriately. The shape of the CT imaging area CA may be slightly deformed as long as this purpose is not spoiled. For example, the curvature of arcs AR, BR, CR, ABR, ACR and BCR may be set variously. The curvature of arcs AR, BR and CR may be smaller than the curvature of arcs ABR, ACR and BCR.

In the above description, the position of the lateral direction blocking plates 15 (15a, 15b) in the lateral direction is changed respectively by the blocking plate lateral direction moving mechanisms 16b to restrict the expansion in the lateral direction of the X-ray cone beam BX and adjust the radiation direction thereof. Alternatively, as shown in FIG. 25, the distance from the lateral direction blocking plates 15 (15a, 15b) of the beam formation mechanism 13 to the X-ray generation section 10 may be adjusted to restrict the expansion in the lateral direction of the X-ray cone beam BX to have a desired width.

Figure 26:
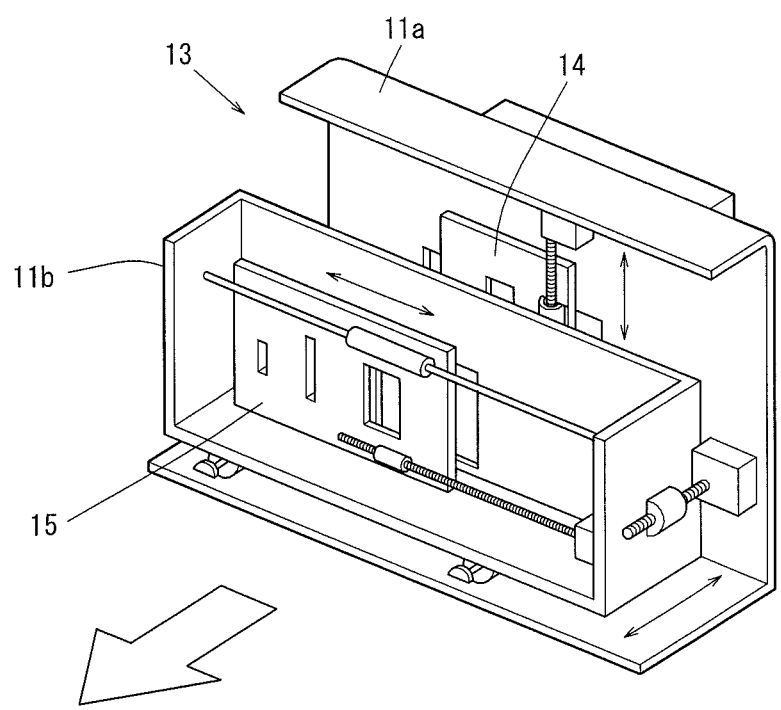
FIG. 26 is a schematic isometric view of a beam formation mechanism in another embodiment.

In this case, as shown in FIG. 26, the housing 11 includes a housing 11a for the vertical direction blocking plates 14 and a housing 11b for the lateral direction blocking plates 15. The housing 11b for the lateral direction blocking plates 15 may be structured to be movable in the radiation direction of the X-ray represented by the arrow ((+y) direction) with respect to the housing 11a for the vertical direction blocking plates 14, by, for example, moving mechanisms substantially the same to the blocking plate moving mechanisms 16 (16a, 16b).

Alternatively, the expansion of the X-ray beam BX in one of the length direction and the lateral direction may be adjusted by the gap between the corresponding blocking plates (14 or 15), whereas the expansion of the X-ray beam BX in the other direction may be adjusted by the distance from the corresponding blocking plates to the X-ray generation section 10. For example, the two L-shaped blocking plates 18 shown in FIG. 7 may be movable in the in the lateral direction and also the distance form the L-shaped blocking plates 18 to the X-ray generation section 10 may be adjusted. In this case, the expansion of the X-ray cone beam BX is adjusted as follows. First, the two L-shaped blocking plates 18 are moved in the radiation direction of the X-ray cone beam BX to adjust the distance thereof to the X-ray generation section 10 and thus to adjust the expansion of the X-ray bone beam BX in the length direction. Then, the two L-shaped blocking plates 18 are moved in the lateral direction to adjust the expansion of the X-ray bone beam BX in the lateral direction.

In the above description, in the state where the revolution shaft 31 is secured as the revolution center Sc of the revolving arm 30, the length direction blocking plates 14 and the lateral direction blocking plates 15 of the beam formation mechanism 13 are moved by the blocking plate moving mechanisms 16 in accordance with the revolution position to restrict the expansion of the X-ray cone beam BX in the length direction and the lateral direction. Thus, the radiation range of the X-ray cone beam BX is adapted to the CT imaging area CA, which is to be irradiated with the X-ray cone beam BX. Alternatively, a shaft moving mechanism 34 for moving the revolution shaft 31 in the horizontal direction with respect to the upper frame 41 may be provided. In this case, the revolution shaft 31 may be moved by the shaft moving mechanism 34 so that the radiation range of the X-ray cone beam BX is adapted to the CT imaging area CA, which is to be irradiated with the X-ray cone beam BX.

Figure 28A:
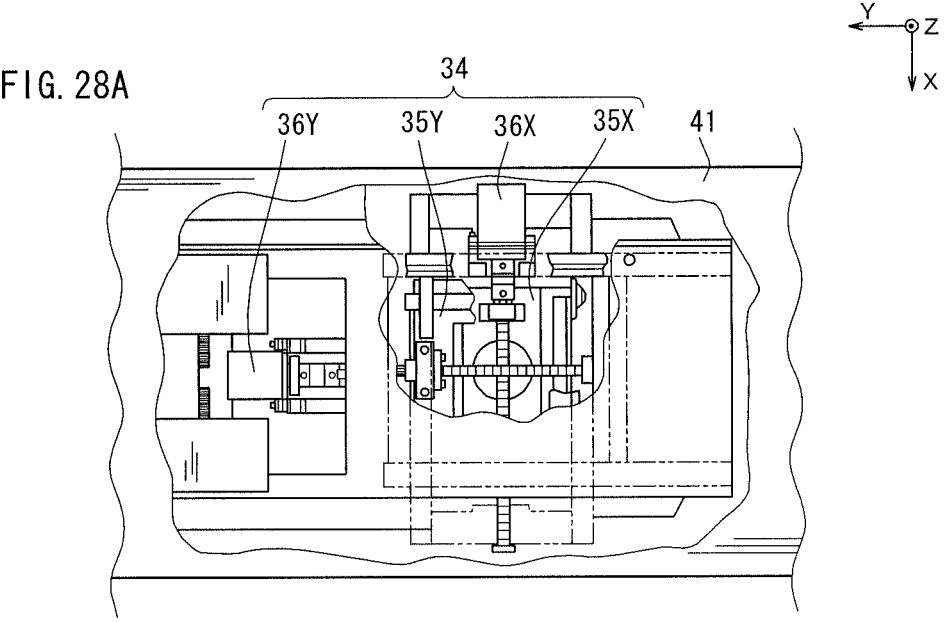
FIGS. 28A and 28B show an internal structure of a revolving arm and an upper frame for moving a revolution shaft.
Figure 28B:
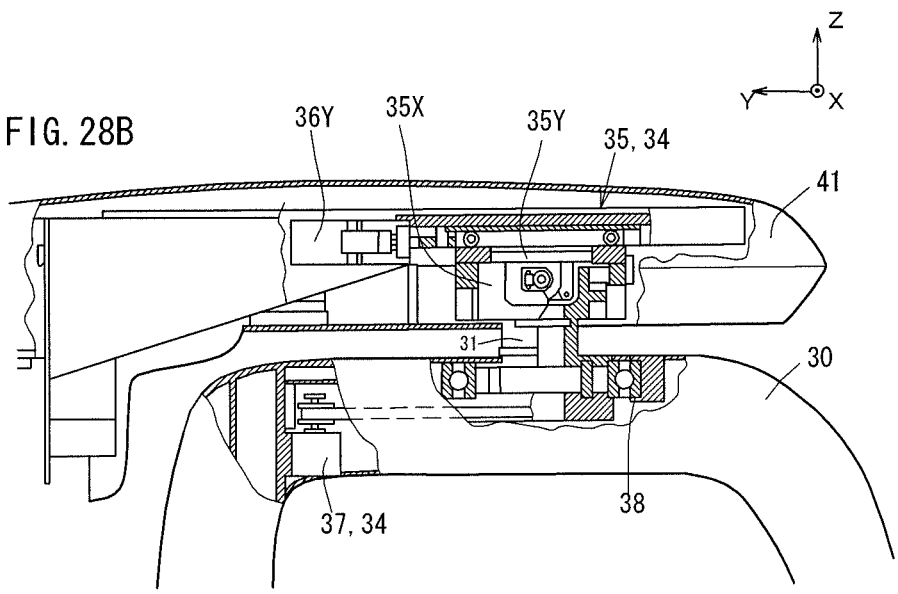
Figure 29:
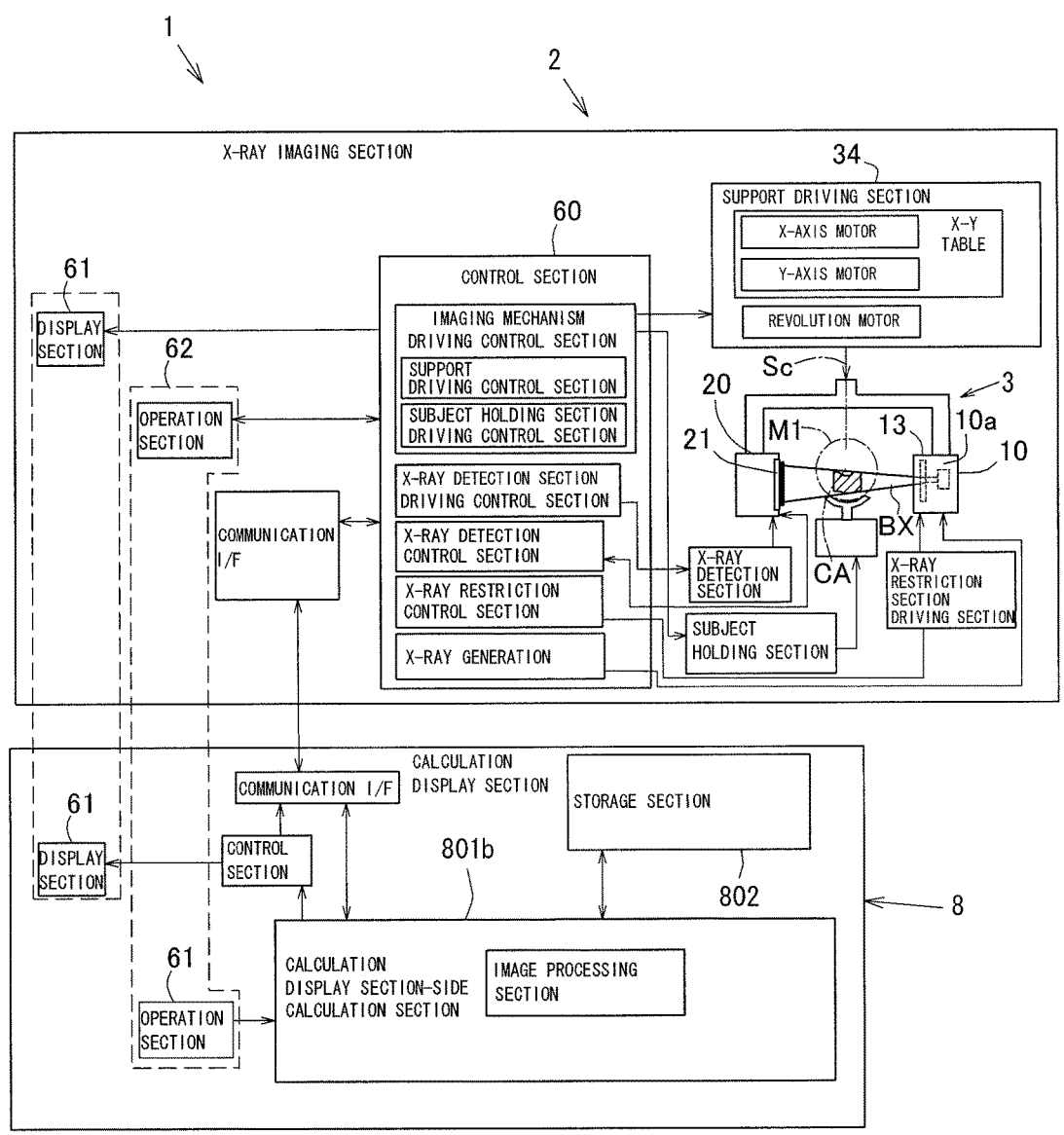
FIG. 29 is a block diagram showing a structure of the X-ray CT imaging device for restricting the expansion of the X-ray cone beam by moving the revolution shaft.

With reference to FIG. 27 through FIG. 30, the X-ray CT imaging device 1 for adjusting the expansion of the X-ray cone beam BX by moving the revolution shaft 31 by use of the shaft moving mechanism 34 will be described. FIG. 27 shows restriction of the expansion of the X-ray cone beam BX performed by moving the revolution center Sc. FIG. 28 shows an internal structure of the revolving arm 30 and the upper frame 41 for moving the revolution shaft 31. FIG. 29 is a block diagram showing a structure of the X-ray CT imaging device 1 for restricting the expansion of the X-ray cone beam BX by moving the revolution shaft 31. FIG. 30 shows another embodiment for moving the revolution shaft 31.

In more detail, FIG. 27(a) is a schematic cross-sectional view showing a state where the revolution shaft 31 is moved in such a direction that the X-ray generation section 10 is distanced from the triangular CT imaging area CAb in order to adapt the expansion of the X-ray cone beam BX in the length direction to the edge of the triangular CT imaging area CAb on the X-ray generation section 10 side. FIG. 27(b) is a schematic cross-sectional view showing a state where the revolution shaft 31 is moved in such a direction that the X-ray generation section 10 approaches the triangular CT imaging area CAb.

FIG. 28(a) is a partially cut cross-sectional view of the upper frame 41 showing an internal structure thereof. FIG. 28(b) is a partially cut cross-sectional view of the revolving arm 30 and the upper frame 41 showing an internal structure thereof. FIG. 28(b) shows the revolving arm 30 and the upper frame 41 as seen from a side of the X-ray CT imaging device 1, and FIG. 28(a) shows the upper frame 41 as seen from above.

The shaft moving mechanism 34 included in the upper frame 41 includes XY tables 35 for moving the revolution shaft 31 with the revolving arm 30 in the horizontal direction, and driving motors 36 for driving the XY tables 35.

The XY tables 35 include an Y table 35Y for moving the revolving arm 30 in the front-rear direction (Y-axis direction) and an X table 35X movable in the lateral direction (X-axis direction) while being supported by the Y table 35Y.

The driving motors 36 include a Y-axis driving motor 36Y for driving the Y table 35Y and an X-axis driving motor 36X for moving the X table 35X in the X-axis direction with respect to the Y table 35Y.

In the X-ray CT imaging device 1, as shown in FIG. 29, the driving motors 36 are connected to the main body control section 60. In accordance with a predetermined driving program, the driving motors 36 move the X table 35X in the left-right direction (X-axis direction) and the Y table 35Y in the front-rear direction (Y-axis direction) while revolving the revolving arm 30. Owing to this, the revolution shaft 31 can be controlled to move two-dimensionally in the front-rear and left-right directions, namely, in the X-axis and Y-axis directions.

In this manner, the revolution shaft 31 is moved in the horizontal direction by the shaft moving mechanism 34. As shown in FIG. 27, even in the case where, for example, the CT imaging area CA is the triangular CT imaging area CAb of the triangular prism shape which has a uniform height, the distance from the revolution center Sc to the edge of the triangular CT imaging area CAb on the X-ray generation section 10 side is changed in accordance with the position of the revolution center Sc. Therefore, the revolution shaft 31 can be moved to adjust the distance from the X-ray generation section 10 to the triangular CT imaging area CAb, so that the X-ray cone beam BX which is output from the X-ray generation section 10 and expands from in the length direction and the lateral direction can be adapted to the height and the width of the edge of the triangular CT imaging area CAb on the X-ray generation section 10 side.

In more detail, the expansion in the length direction of the X-ray cone beam BX is controlled to become larger when the X-ray generation section 10 approaches the triangular CT imaging area CAb and is controlled to become smaller when the X-ray generation section 10 is distanced from the triangular CT imaging area CAb. Owing to this control, the expansion of the X-ray cone beam BX in the length direction and the lateral direction is adapted to the height and the width of the edge of the triangular CT imaging area CAb on the X-ray generation section 10 side. Therefore, the amount of unnecessary exposure to the X-ray can be decreased, and the X-ray CT imaging of the area of interest can be performed with certainty.

FIG. 27(a) shows a state where the edge of the triangular CT imaging area CAb on the X-ray generation section 10 side is close to the X-ray generation section 10. The X-ray generation section 10, the length direction blocking plates 14, the X-ray detection section 20, and the X-ray detector 21 move in the y-axis direction from comparative positions represented by the dashed lines to the positions represented by the solid lines.

The distance of the X-ray generation section 10 from the triangular CT imaging area CAb is increased. The expansion of the X-ray cone beam BX at the edge of the triangular CT imaging area CAb on the X-ray generation section 10 side is increased than before the movement.

FIG. 27(b) shows a state where the edge of the triangular CT imaging area CAb on the X-ray generation section 10 side is far from the X-ray generation section 10. The X-ray generation section 10, the length direction blocking plates 14, the X-ray detection section 20, and the X-ray detector 21 move in the y-axis direction from comparative positions represented by the dashed lines to the positions represented by the solid lines.

The distance of the X-ray generation section 10 from the triangular CT imaging area CAb is decreased. The expansion of the X-ray cone beam BX at the edge of the triangular CT imaging area CAb on the X-ray generation section 10 side is decreased than before the movement.

Alternatively, the expansion of the X-ray cone beam BX in one of the length direction and the lateral direction may be adjusted by the gap between the blocking plates (14 or 15), whereas the expansion of the X-ray cone beam BX in the other direction may be adjusted by moving the revolution center Sc and thus changing the distance from the X-ray generation section 10 to the triangular CT imaging area CAb.

Figure 30A:
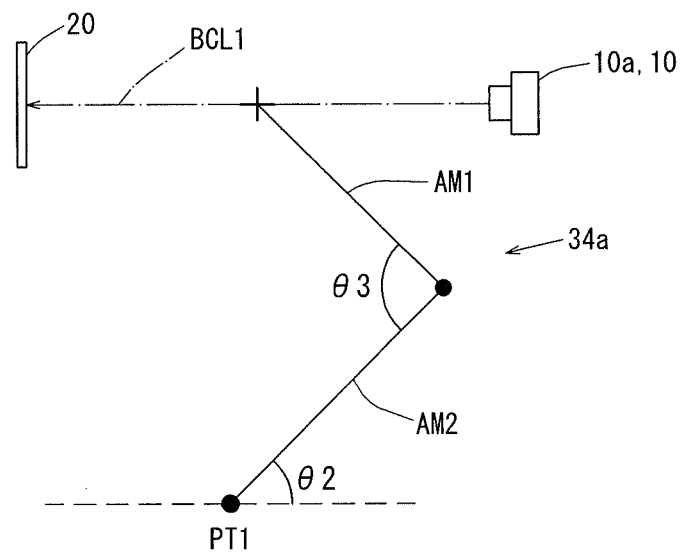
FIGS. 30A and 30B show another embodiment for moving the revolution shaft.
Figure 30B:
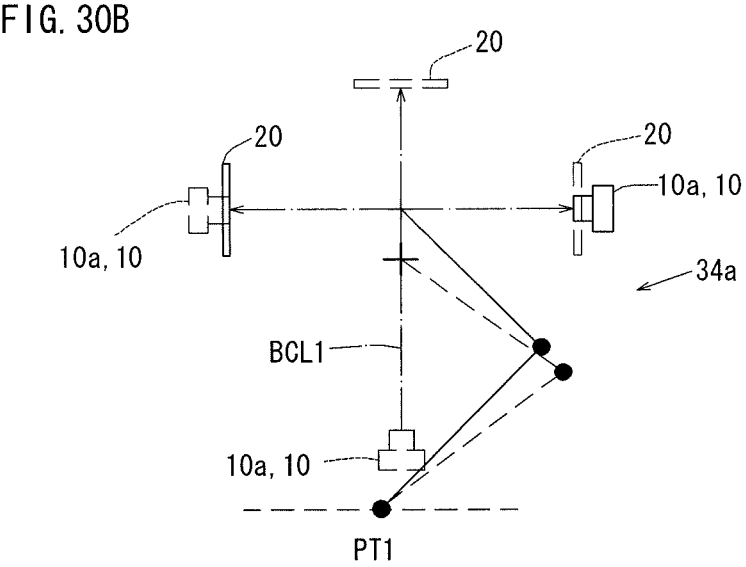

As shown in FIG. 30(b), in addition to the expansion in the lateral direction of the X-ray cone beam BX being restricted by the lateral direction blocking plates 15, the revolution center Sc is moved to adjust the distance from the X-ray generation section 10 to the triangular CT imaging area CAb, so that the expansion in the lateral direction of the X-ray cone beam BX is adapted to the triangular CT imaging area CAb. When these two types of restriction methods are used together, as compared with the case when the expansion of the X-ray cone beam BX is restricted by only the lateral direction blocking plates 15 as shown in FIG. 30(a), the amount of movement of the lateral direction blocking plates 15 can be decreased.

In the above description, the revolution shaft 31 for the revolving arm 30 is moved with respect to the upper frame 41 by the shaft moving mechanism 34. Alternatively, a chair on which the subject M1 can sit may be provided in the X-ray CT imaging device 1. In this case, the chair may be moved in the horizontal direction with respect to the revolving arm 30 which is revolving, so that the revolution center Sc is relatively moved with respect to the imaging target OB2. Still alternatively, the shaft moving mechanism 34 and the chair movable in the horizontal direction may be used together.

Figure 33:
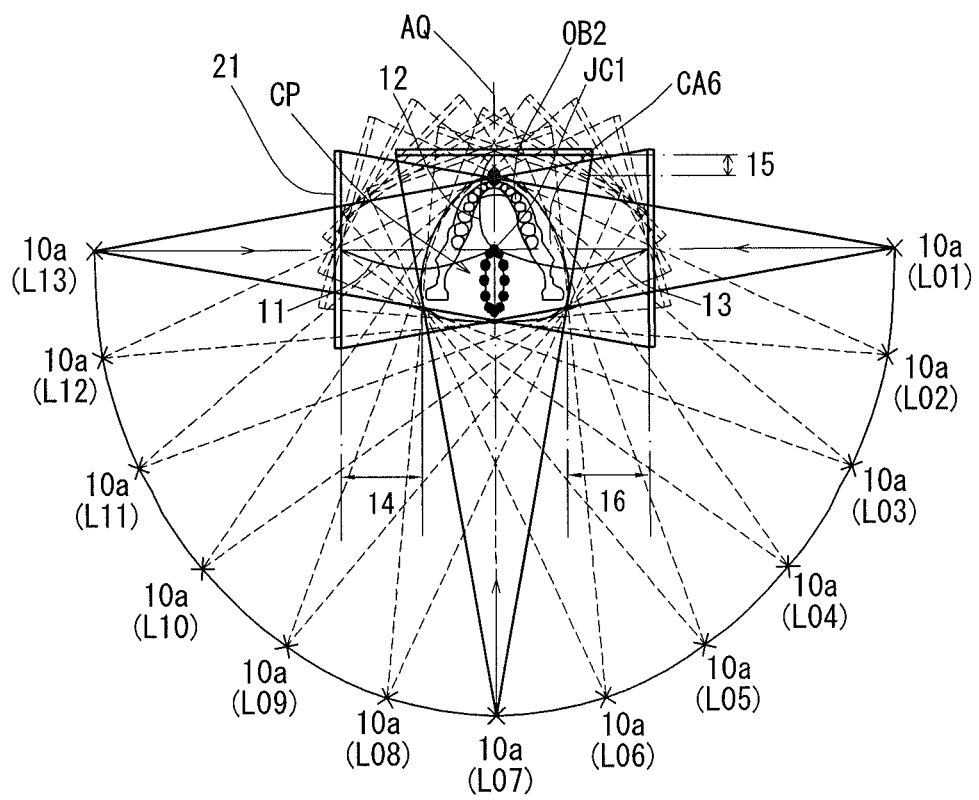
FIG. 33 is a plan view conceptually showing imaging of an imaging target.

FIG. 29 shows a device capable of controllably moving the revolution shaft 31 two-dimensionally in the X direction and the Y direction, namely, in the left-right direction and the front-rear direction. When such a device is used, as shown in FIG. 33, the X-ray generator 10a is moved closer to the imaging target OB2 while the X-ray detector 21 is moved farther from the imaging target OB2, so that the expansion in the lateral direction of the X-ray cone beam BX with respect to the imaging target OB2 is made smaller. The X-ray generator 10a is moved farther from the imaging target OB2 while the X-ray detector 21 is moved close to the imaging target OB2, so that the expansion in the lateral direction of the X-ray cone beam BX with respect to the imaging target OB2 is made larger. By such control, the CT imaging area CA can be formed to be the triangular CT imaging area CAb.

With such a structure also, the expansion in the length direction of the X-ray cone beam BX can be adjusted in accordance with the height of the triangular CT imaging area CAb.

Figure 34:
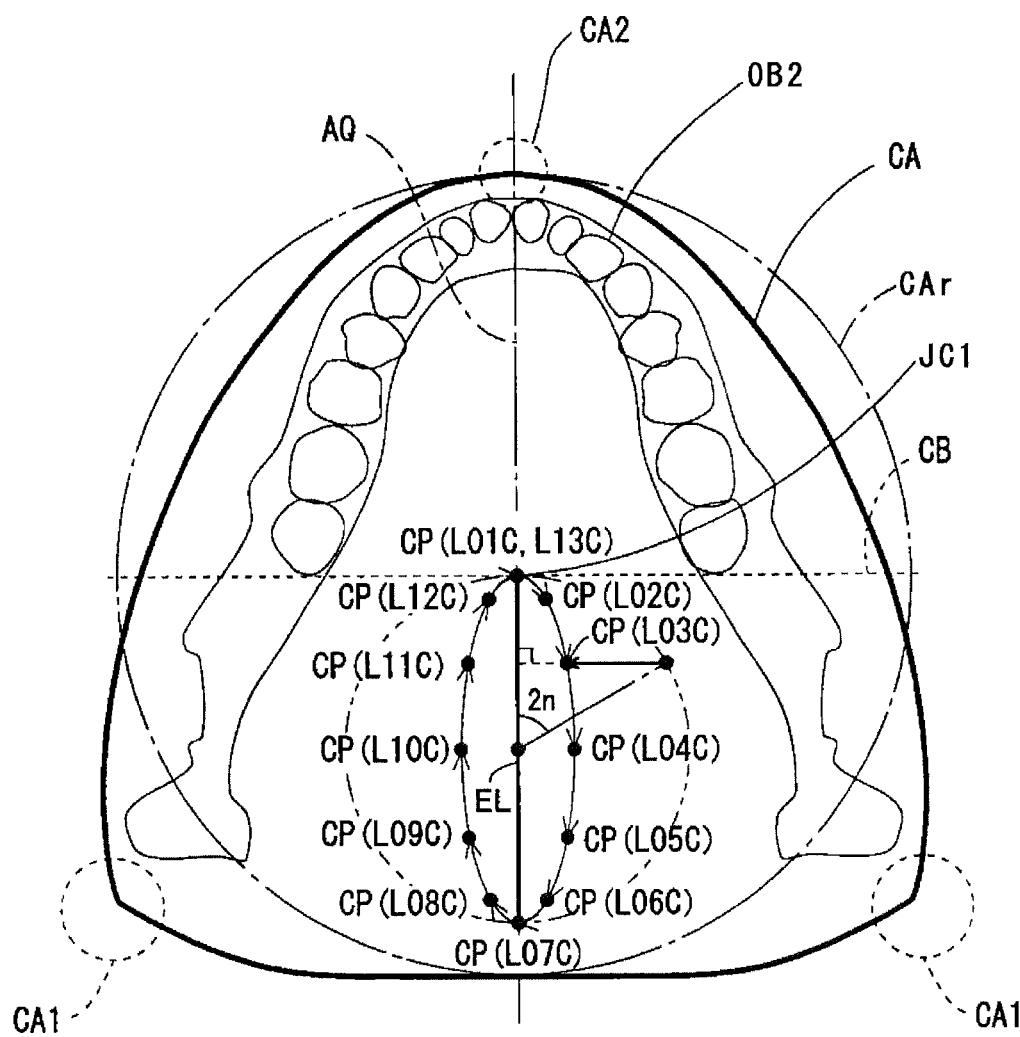
FIG. 34 is an enlarged plan view showing the locus of movement of a revolution reference point and a CT imaging area shown in FIG. 33.

FIG. 33 is a plan view conceptually showing imaging of the imaging target OB2. FIG. 34 is an enlarged plan view showing the locus of movement of a revolution reference point CP and the CT imaging area CAb shown in FIG. 33. In the CT imaging shown in FIG. 33, the imaging target OB is the upper and lower jawbones including all the teeth. FIG. 33 shows the movement of the X-ray generator 10a from position L01 to position L13 which is made while the revolving arm 30 rotates by 180 degrees about the revolution shaft 31.

FIG. 33 also shows the X-ray cone beam BX which is output from each of positions L01 through L13 of the X-ray generator 10a while the revolving arm 30 is rotated from position L01 by 15 degrees at a time. Strictly, positions L01 through L13 are the positions at which the X-ray of the X-ray tube is generated, namely, the positions of the X-ray focal point. Position L01 is the position at which the X-ray generator 10a starts moving in the CT imaging, and position L13 is the position at which the X-ray generator 10a stops moving in the CT imaging.

The X-ray generator 10a starts moving from a position just to the right of the head of the human body, passes behind the head, and reaches a position just to the left of the head. In the figure, reference sign CP represents the revolution reference point, and is the instantaneous revolution center at each position of the X-ray generator 10a and the X-ray detector 21. Herein, for easier understanding, it is assumed that the axial center of the revolution shaft 31 matches the revolution reference point CP.

As the revolving arm 30 rotates by 180 degrees, the revolution reference point CP starts moving from position L01C, sequentially passes positions L02C, L03C, L04C, . . . , and returns to position L01C. In the example shown here, while the revolving arm 30 rotates by 180 degrees, the revolution reference point CP moves around the ellipse once on a circumference thereof. The movement of the revolution reference point CP is realized by the movement of the revolution shaft 31, which is controlled to be driven by the X-axis driving motor 36X and the Y-axis driving motor 36Y.

The numerals of positions L01C through L13C respectively correspond to the numerals of positions L01 through L13.

As shown in FIG. 33, the X-ray detector 21 moves, during the CT imaging, at least from a position to the left or to the right of the imaging target OB to a position to the right or to the left of the imaging target OB, and thus forms a semicircular locus. In the example shown here, the X-ray detector 21 forms a locus starting from a position to the right of the middle of the head of the human body, which is the subject M1, passing in front of the head, and reaching a position to the left of the middle of the head; namely, a locus of moving from a right position to a left position facing each other with respect to symmetry axis AQ.

Now, it is assumed that the triangular CT imaging area CAb is the area of interest CAb which is located such that the dental arch is accommodated in the area shown in FIG. 22 as seen in a plan view. When the X-ray detector 21 is at either the left position or the right position of the semicircular locus (i.e., when the X-ray generator 10*a* is at either position L01 or L13), and when the X-ray detector 21 is at a position intermediate between the left position and the right position (i.e., when the X-ray generator 10*a* or the X-ray detector 21 is at position L07 on the symmetry axis AQ, which is the middle position), the X-ray detector 21 and the X-ray generator 10*a* have the following positional relationship. A distance 11 or 13 between the X-ray detector 21 and the area of interest CAb when the X-ray detector 21 is at either the left position or the right position, is longer than a distance 12 between the X-ray detector 21 and the area of interest CAb when the X-ray detector 21 is at the intermediate position.

The "distance between the X-ray detector 21 and the area of interest CAb" is a distance between the center area of the detection plane 21*a* of the X-ray detector 21 and one point in the area of interest CAb; for example, the distance between the center area of the detection plane 21*a* of the X-ray detector 21 and one point JC1 at the center of the jawbone (or dental arch).

When the X-ray generator 10*a* moves between position L01 and position L13, the revolution reference point CP moves between position L01C and position L13C shown in FIG. 34. Position L01C matches position L13C.

In the CT imaging shown in FIG. 33, the revolution motor 37, the X-axis driving motor 36X and the Y-axis driving motor 36Y are controlled in association with each other, such that the revolving arm 30 is revolved while the X-ray cone beam BX is output and thus the CT imaging area CA having a generally triangular shape is formed.

The structure shown in FIG. 33 and FIG. 34 has an advantage that the amount of blocking in the lateral direction by the lateral direction blocking plates 15 (15*a*, 15*b*) may be fixed and thus the structure of the lateral direction blocking plates 15 can be simplified.

Needless to say, the associated control on the revolution motor 37, the X-axis driving motor 36X and the Y-axis driving motor 36Y, and the blocking control by the lateral direction blocking plates 15 (15*a*, 15*b*), may be combined to form the triangular CT imaging area CAb.

With the structure shown in FIG. 33 and FIG. 34 also, the expansion in the length direction of the X-ray cone beam BX is adjusted in accordance with the height of the triangular CT imaging area CAb.

FIG. 35(*a*) is a schematic view as seen in the x-axis direction of the X-ray cone beam BX restricted regarding the length direction radiation range when the X-ray generator 10*a* is at position L01. Similarly, FIG. 35(*b*) is a schematic view as seen in the x-axis direction of the X-ray cone beam BX restricted regarding the length direction radiation range when the X-ray generator 10*a* is at position L07.

Line JC is a line extending in the Z-axis direction and passing the one point JC1 at the center of the jawbone (or dental arch).

In the state of FIG. 35(*a*), the distance between the X-ray generator 10*a* and an edge CAb1 of the triangular CT imaging area CAb which is closest to the X-ray generator 10*a* is short. Therefore, the expansion in the length direction of the X-ray cone beam BX (cone angle θX1 in the length direction of the X-ray cone beam BX) is set large. By contrast, in the state of FIG. 35(*b*), the distance between the X-ray generator 10*a* and an edge CAb2 of the triangular CT imaging area CAb which is closest to the X-ray generator 10*a* is long. Therefore, the expansion in the length direction of the X-ray cone beam BX (cone angle θX2 in the length direction of the X-ray cone beam BX) is set small.

In FIG. 35(*b*), the positions of the triangular CT imaging area CAb and the line JC in FIG. 35(*a*) are shown with the one-dot chain line for comparison.

The positional relationship among elements in each of FIG. 35(*a*) and FIG. 35(*b*) is shown in a slightly emphasized manner for easier understanding.

Cone angle θX1 and cone angle θX2 have the relationship of θX1>θX2. The cone angle is adjusted by adjusting the positions in the length direction of the length direction blocking plates 14 (14*a*, 14*b*) with respect to the output opening 12 by use of the blocking plate length direction moving mechanisms 16*a*.

In the above description, the revolution center Sc of the revolving arm 30 which is revolving is moved by the shaft moving mechanism 34 including the XY tables 35. The moving mechanism is not limited to having this structure, and may be a moving mechanism shown in FIG. 30.

FIG. 30(*a*) schematically shows a moving mechanism 34*a* according to a modification. FIG. 30(*b*) shows the positions of the X-ray generator 10*a*, the revolution shaft 31 (represented with (+) in the figure), and the X-ray detection section 20 in three phases in which the revolving arm 30 is revolved by 90 degrees step by step. In FIG. 30(*a*), the revolving arm and the X-ray cone bean are not shown, and only the horizontal direction reference radiation central line BCL1 is shown.

The moving mechanism 34*a* is controlled based on polar coordinates, and the revolving arm 30 is moved by driving two arms AM1 and AM2.

This will be described in more detail. The moving mechanism 34*a* has a fixed pivot reference point PT1 with respect to the main body 2 (not shown). One end of the first arm AM1 is pivotably supported at the pivot reference point PT1 as the support. At the other end of the first arm AM1, one end of the second arm AM2 is pivotably supported. At the other end of the second arm AM2, the revolution shaft 31 (represented with (+) in the figure) for the revolving arm 30 is pivotably supported. The revolving arm 30 is driven to revolve about an axis of the revolution shaft 31 by a driving motor or the like (not shown). The revolution shaft 31 may be secured so as not to pivot at the other end of the second arm AM2 so that the revolving arm 30 revolves about the revolution shaft 31.

The arms AM1 and AM2 are each controlled to pivot by an arm driving motor (not shown). The arms AM1 and AM2 are each coupled to the arm driving motor such that the pivoting angle thereof is controllable. Pivoting angle θ2 of the arm AM1 with respect to the main body 2 of the X-ray CT imaging device 1, and relative pivoting angle θ3 of the arm AM2 with respect to the arm AM1, are controlled. Thus, the position (+) of the revolution shaft 31 can be controlled in a two-dimensional plane perpendicular to the revolution shaft 31. The moving mechanism 34*a* shown in FIG. 30 also can relatively move the revolving arm 30 (i.e., the support section) with respect to the subject M1 in a two-dimensional plane perpendicular to the revolution shaft 31.

As described above, the X-ray CT imaging device 1 for performing X-ray CT imaging of a CT imaging area CA of the subject M1 includes an imaging mechanism including the X-ray generation section 10 for generating X-ray, the beam formation mechanism 13 for blocking and restricting the radiation range of the X-ray generated by the X-ray generation section 10 to form the X-ray cone beam BX to be directed to the CT imaging area CA, and the X-ray detection section 20 for detecting the X-ray cone beam BX directed to the subject M1; the revolving arm 30 for supporting the X-ray generation section 10 and the X-ray detection section 20 in the state where the X-ray generation section 10 and the X-ray detection section 20 have the subject M1 therebetween; the upper frame 41 including the revolution motor 37 for revolving the revolution arm 30 at least about an axis of the revolution shaft 31 with respect to the subject M1; and the main body control section 60 for controlling at least the X-ray generation section 10, the beam formation mechanism 13 and the upper frame 41 including the revolution motor 37. A direction parallel to a direction of the axis of the revolution shaft 31 is the length direction. The beam formation mechanism 13 includes the length direction blocking plates 14 for blocking and restricting the radiation range of the X-ray cone beam BX in the length direction with respect to the CT imaging area CA; and the blocking plate length direction moving mechanisms 16a. During the X-ray CT imaging when the revolving arm 30 is revolving, the blocking plate length direction moving mechanisms 16a adapt the expansion in the length direction of the X-ray cone beam BX, which is to be restricted by the length direction blocking plates 14, to the shape of the CT imaging area CA in accordance with the revolution position of the imaging mechanism driven by the upper frame 41 including the revolution motor 37. The blocking plate length direction moving mechanisms 16a are controlled by the main body control section 60. Owing to this, the area of interest can be irradiated with the X-ray appropriately, the amount of unnecessary exposure to the X-ray can be decreased, and the X-ray CT imaging of the area of interest can be performed with certainty.

This will be described in more detail. For example, in the case where the X-ray CT imaging is performed with a constant expansion in the length direction of the X-ray cone beam BX on an area of interest in which the height in the axial direction of the revolution shaft, which is revolving, varies in accordance with the revolution direction, the following occurs. When the CT imaging area CA by the X-ray cone beam BX is larger than the area of interest, an area other than the area of interest may be undesirably irradiated with the X-ray, and thus the amount of exposure to the X-ray may be unnecessarily increased. By contrast, when the CT imaging area CA by the X-ray cone beam BX is smaller than the area of interest, the area of interest may not be irradiated with the X-ray.

In order to avoid this, the blocking plate length direction moving mechanisms 16a is controlled by the main body control section 60 such that the expansion in the length direction of the X-ray cone beam BX, which is to be restricted by the length direction blocking plates 14, is adapted to the shape of the CT imaging area CA having an appropriate height in the length direction for the area of interest, in accordance with the revolution position of the imaging mechanism driven by the upper frame 41 including the revolution motor 37. Thus, the amount of unnecessary exposure to the X-ray can be decreased, and the X-ray CT imaging of the area of interest can be performed with certainty.

The blocking plate length direction moving mechanisms 16a for moving the length direction blocking plates 14 in the length direction allow the expansion of the X-ray cone beam BX to be adjusted with a simple structure and to be adapted to the shape of the CT imaging area CA having an appropriate height in the length direction for the area of interest.

The plurality of length direction blocking plates 14 (14a, 14b) are movable independently in the length direction with respect to the CT imaging area CA, and are moved independently by the blocking plate length direction moving mechanisms 16a. Therefore, the radiation direction of the X-ray cone beam BX in the length direction can be adjusted with respect to the X-ray generation section 10.

This will be described in more detail. The plurality of length direction blocking plates 14 movable independently in the length direction with respect to the CT imaging area CA are shifted in the length direction from the length-direction center of the X-ray cone beam BX output from the X-ray generation section 10. Thus, the radiation direction of the X-ray cone beam BX can be adjusted in the length direction with respect to the X-ray generation section 10. Therefore, even when the area of interest is a local area such as a part of the upper jaw or the lower jaw and such a local area of interest is eccentric in the length direction with respect to the radiation direction from the X-ray generation section 10, the shape of the CT imaging area CA can be adapted to the area of interest with certainty.

The upper frame 41 including the revolution motor 37 is provided with the shaft moving mechanism 34 for relatively moving the revolution shaft 31 with respect to the subject M1, and the distance from the X-ray generation section 10 to the subject M1 is adjusted by the shaft moving mechanism 34. Thus, the expansion in the length direction of the X-ray cone beam BX can be adapted to the shape of the CT imaging area CA having an appropriate height in the length direction for the area of interest.

The main body control section 60 controls the expansion in the length direction of the X-ray cone beam BX to become larger when the X-ray generation section 10 approaches the CT imaging area CA and to become smaller when the X-ray generation section 10 is distanced from the CT imaging area CA. Therefore, even when the length direction blocking plates 14 are moved in the length direction by the blocking plate length direction moving mechanisms 16a or when the distance from the X-ray generation section 10 to the subject M1 is adjusted by the shaft moving mechanism 34, the shape of the CT imaging area CA is adapted to the area of interest. Thus, the amount of unnecessary exposure to the X-ray can be decreased, and the X-ray CT imaging of the area of interest can be performed with certainty.

The moving mechanisms 23 for relatively moving the X-ray detector 21 of the X-ray detection section 20 with respect to the revolving arm 30 are provided, and are controlled by the main body control section 60 in accordance with the radiation range of the X-ray cone beam BX. Thus, the X-ray detection section 20 can be made compact.

This will be described in more detail. The expansion in the length direction of the X-ray cone beam BX is adjusted by the blocking plate length direction moving mechanisms 16a. Therefore, after the range of the X-ray detected by the X-ray detection section 20 is adjusted, the expansion in the length direction of the X-ray cone beam BX is made different. Especially when the radiation range of the X-ray cone beam BX in the length direction is adjusted, the center of the detection range is moved.

In order to avoid this, the moving mechanisms 23 for relatively moving the X-ray detection section 20 with respect to the revolving arm 30 are provided, and are controlled by the main body control section 60 in accordance with the radiation range of the X-ray cone beam BX. Owing to this, the X-ray detection section 20 can follow the detection range which is made different or moved, and thus a maximum possible projection range can be covered by the X-ray detection section 20 even when the X-ray detection section 20 is compact. Accordingly, the X-ray detection section 20 can be made compact as compared with the case where the size of the X-ray detection section is adapted to the maximum possible projection range. Thus, the cost of the X-ray detection section 20, which requires a highly expensive detection sensor, can be reduced.

A direction which is perpendicular to the direction from the X-ray generator 10 to the X-ray detector 20 and also perpendicular to the length direction is the lateral direction. The beam formation mechanism 13 includes the lateral direction blocking plates 15 for blocking and restricting the radiation range of the X-ray cone beam BX in the lateral direction with respect to the CT imaging area CA. In addition, the blocking plate lateral direction moving mechanisms 16*b* are provided. During the X-ray CT imaging when the revolving arm 30 is revolving, the blocking plate lateral direction moving mechanisms 16*b* adapt the expansion in the lateral direction of the X-ray cone beam BX, which is to be restricted by the lateral direction blocking plates 15, to the shape of the CT imaging area CA in accordance with the revolving position of the imaging mechanism driven by the upper frame 41 including the revolution motor 37. Therefore, the area of interest is irradiated with the X-ray appropriately, and the CT imaging area CA having a desired planar shape in accordance with the shape of the area of interest can be formed. Thus, the amount of unnecessary exposure to the X-ray can be decreased.

This will be described in more detail. During the X-ray CT imaging when the revolving arm 30 is revolving, the blocking plate lateral direction moving mechanisms 16*b* adapt the expansion in the lateral direction of the X-ray cone beam BX, which is to be restricted by the lateral direction blocking plates 15, to the shape of the CT imaging area CA in accordance with the revolving position of the imaging mechanism driven by the upper frame 41 including the revolution motor 37. Owing to this, even when the diameter of the area of interest varies with respect to the revolution shaft 31 in accordance with the revolution direction as seen in a plan view, or even when the area of interest is eccentric with respect to the revolution shaft 31 as seen in a plan view, the CT imaging area CA having a desired planar shape in accordance with the shape of the area of interest can be formed. Thus, the amount of unnecessary exposure to the X-ray can be decreased.

The plurality of lateral direction blocking plates 15 (15*a*, 15*b*) are movable independently in the lateral direction with respect to the CT imaging area CA, and are moved independently by the blocking plate lateral direction moving mechanisms 16*b*. Therefore, the radiation direction of the X-ray cone beam BX in the lateral direction can be adjusted with respect to the X-ray generation section 10.

This will be described in more detail. The plurality of lateral direction blocking plates 15 movable independently in the lateral direction with respect to the CT imaging area CA are shifted in the lateral direction from the lateral-direction center of the X-ray cone beam BX output from the X-ray generation section 10. Thus, the radiation direction of the X-ray cone beam BX can be adjusted in the lateral direction with respect to the X-ray generation section 10. Therefore, even when the area of interest is shifted in the lateral direction with respect to the revolution shaft 31, the shape of the CT imaging area CA can be adapted to the area of interest with certainty.

At least the lateral direction blocking plates 15 are controlled by the main body control section 60 in accordance with the revolution movement driven by the upper frame 41 including the revolution motor 37, such that the CT imaging area CA has a generally triangular shape as seen in a plan view. In this manner, the shape of the CT imaging area CA is made generally triangular in accordance with the shape of the area of interest. Thus, the amount of unnecessary exposure to the X-ray can be decreased, and the detection range detectable by the X-ray detection section 20 can be made small.

The CT imaging area CA formed to have a generally triangular shape as seen in a plan view is set to accommodate the entirety of the dental arch including the anterior teeth T1, the left posterior teeth T2, and the right posterior teeth T3. Therefore, the X-ray CT imaging can be performed with certainty on a site which needs to be imaged.

In the case where the generally triangle shape as seen in a plan view is formed such that at least one of three corners is formed of an arc convexed outward and thus is rounded, even when the area of interest includes a generally semicircular (encompassing generally semi-elliptical) imaging target OB2, the shape of the CT imaging area CA can be adapted to the shape of the area of interest. Thus, the amount of unnecessary exposure to the X-ray can be decreased.

In the case where the generally triangle shape as seen in a plan view is formed such that at least one of three sides includes an arc convexed outward at a central part thereof, even when the area of interest includes a generally semicircular imaging target OB2, the shape of the CT imaging area CA can be adapted to the shape of the area of interest with higher precision. Thus, the amount of unnecessary exposure to the X-ray can be further decreased.

The generally triangle shape as seen in a plan view may be formed as follows. One of three sides has outward protrusions at both of left and right ends thereof, the apex facing the one side and each of the protrusions are connected by a curved line, and the generally triangular shape is bilaterally symmetrical with respect to the axis of symmetry passing through the apex and the center of the one side. In this case, even when the area of interest includes a generally semicircular imaging target OB2, the shape of the CT imaging area CA can be adapted to the shape of the area of interest with higher precision. Thus, the amount of unnecessary exposure to the X-ray can be further decreased.

The main body control section 60 changes the radiation range restricted by the beam formation mechanism 13 such that either one of the following two types of X-ray CT imaging is selectable: generally triangular imaging area X-ray CT imaging performed on a generally triangular CT imaging area CAb as seen in a plan view, and X-ray CT imaging performed on a local CT imaging area CAa. Therefore, for example, the CT imaging area CA may have a generally triangular shape as seen in a plan view in which the anterior teeth T1, the left posterior teeth T2, and the right posterior teeth T3 of the dental arch are accommodated, or may have an elliptical shape as seen in a plan view in which a local area including only the posterior teeth is accommodated. In this manner, the X-ray CT imaging device 1 is applicable to any type of X-ray CT imaging. Thus, the applicability of the X-ray CT imaging device 1 which can decrease the amount of unnecessary exposure to the X-ray is improved.

An X-ray slit beam BXP for panorama imaging which is formed by changing the radiation range restricted by the beam formation mechanism 13 is output. In addition, the upper frame 41 including the revolution motor 37 is controlled to revolve the revolving arm 30 such that the output X-ray slit beam BXP forms a locus for panorama X-ray imaging. Thus, even when a panorama image is required, it is not necessary to prepare another X-ray imaging device. Thus, the X-ray CT imaging device 1 which can decrease the amount of unnecessary exposure to the X-ray is usable to perform panorama X-ray imaging by use of an X-ray slit beam BXP.

The CT imaging area according to the present invention corresponds to the CT imaging area CA, the local CT imaging area CAa, and the triangular CT imaging area CAb in the above-described embodiment; and similarly, the X-ray generator corresponds to the X-ray generator 10a, which is a main element of the X-ray generation section 10;

the X-ray cone beam corresponds to the X-ray cone beam BX, the large radiation field CT X-ray cone beam BX1, and the small radiation field CT X-ray cone beam BX2;

the X-ray restriction section corresponds to the beam formation mechanism 13;

the X-ray detector corresponds to the X-ray detector 21, which is a main element of the X-ray detection section 20;

the support corresponds to the revolving arm 30;

the imaging mechanism driving section corresponds to the upper frame 41 including the revolution motor 37;

the control section corresponds to the main body control section 60;

the length direction X-ray blocking section and the length direction blocking member correspond to the length direction blocking plate 14 and a part of the L-shaped blocking plate 18;

the length direction adjusting section and the blocking section length direction moving section correspond to the blocking plate length direction moving mechanism 16a;

the revolution shaft moving mechanism corresponds to the shaft moving mechanism 34 and the moving mechanism 34a;

the X-ray detector moving section corresponds to the moving mechanism 23;

the lateral direction X-ray blocking section and the lateral direction blocking member correspond to the lateral direction blocking plate 15 and a part of the L-shaped blocking plate 18;

the lateral direction adjusting section and the blocking section lateral direction moving section correspond to the blocking plate lateral direction moving mechanism 16b;

the left and right posterior teeth correspond to the left posterior teeth T2 and the right posterior teeth T3;

the CT imaging area CT having a generally triangular shape as seen in a plan view corresponds to the triangular CT imaging area CAb; and the another-shaped imaging area corresponds to the local CT imaging area CAa. However, the present invention is not limited to the above-described embodiment, and may be carried out in various other embodiments.

In this case, for example, the triangular CT imaging area CAb may be irradiated with the above-described X-ray cone beam BX1 for the large radiation field CT, and the local CT imaging area CAa may be irradiated with the above-described X-ray cone beam BX2 for the small radiation field CT.

For example, first X-ray CT imaging in which the imaging target OB2 is a first area of interest and the entirety of the first area of interest is the triangular CT imaging area CAb, or second X-ray CT imaging in which the local imaging target OB1, which is a part of the first area of interest, is a second area of interest and the second area of interest is the local CT imaging area CAa, may be selectable.

In this case, for example, the first X-ray CT imaging performed on the generally triangular CT imaging area CAb as seen in a plan view as the first area of interest, which is the entirety of the anterior teeth T1, the left posterior teeth T2, and the right posterior teeth T3 of the dental arch, or the second X-ray CT imaging performed on the local CT imaging area CAa as the second area of interest, which is the local site of only the posterior teeth, can be selected. Therefore, the applicability of the X-ray CT imaging device 1 which can decrease the amount of unnecessary exposure to the X-ray is improved.

Figure 31:
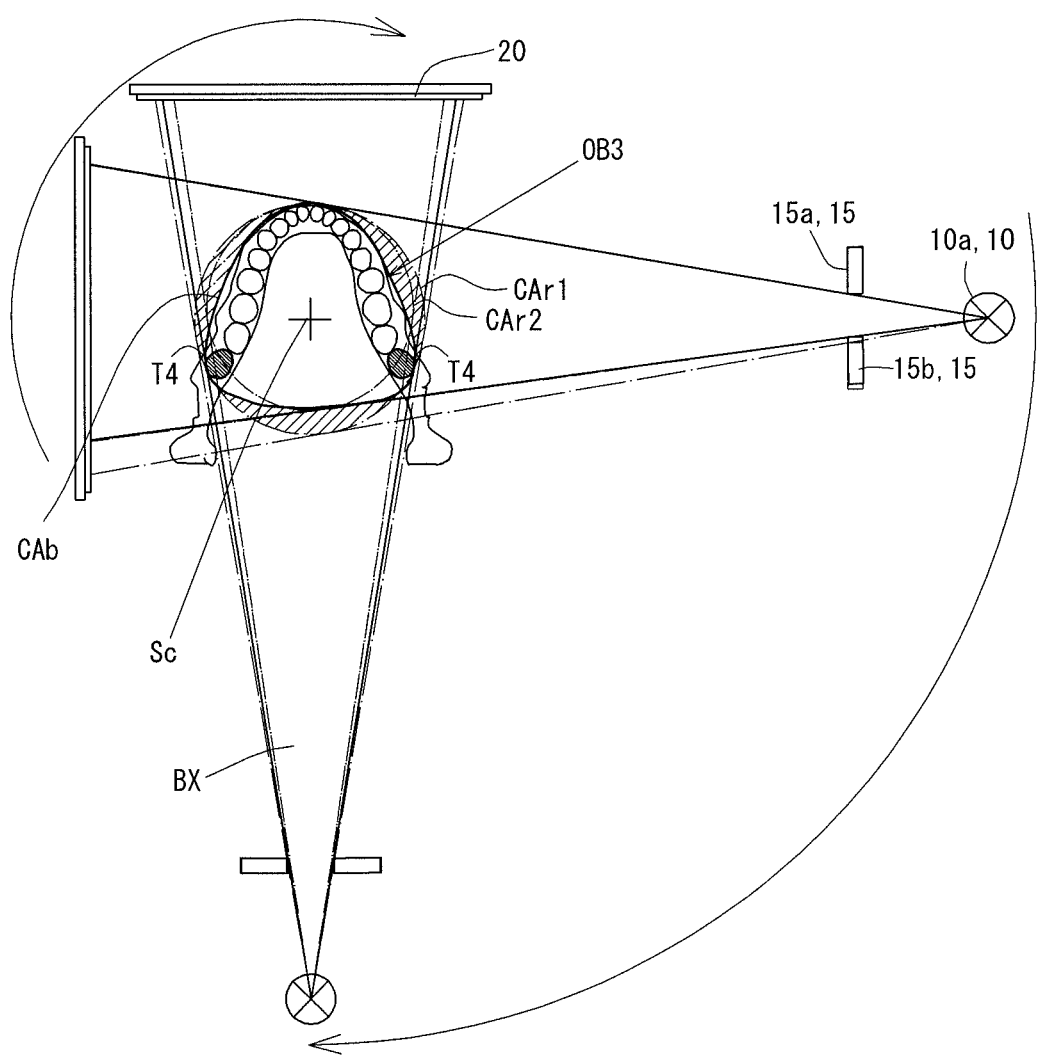
FIG. 31 is a plan view showing, in comparison, a case where the CT imaging area is circular and a case where the CT imaging area is generally triangular in another embodiment with a different range of imaging target.

In the above description, the X-ray CT imaging device 1 performs X-ray CT imaging in which the imaging target OB2 is the entirety of the dental arch including the anterior teeth T1, the left posterior teeth T2, the right posterior teeth T3, and the left and right temporomandibular joints. FIG. 31 is a plan view showing, in comparison, a case where the CT imaging area is circular and a case where the CT imaging area is generally triangular, when the imaging target is an imaging target OB3 having a different range from that of the imaging target OB2. As shown in FIG. 31, the X-ray CT imaging device 1 may perform X-ray CT imaging of the imaging target OB3, which includes the anterior teeth T1, the left posterior teeth T2, the right posterior teeth T3, and the wisdom teeth T4.

The X-ray CT imaging device 1 may be structured to be capable of performing all of CT imaging of the triangular CT imaging area CAb for the imaging target OB2, CT imaging of the triangular CT imaging area CAb for the imaging target OB3, and CT imaging of the local CT imaging area CAa.

In the case where X-ray CT imaging of the imaging target OB3 including the wisdom teeth T4 is performed by a conventional X-ray CT imaging device in which the X-ray detector has a small detection plane, the CT imaging area is a cylindrical CT imaging area CAr2 having a diameter of about 80 mm. Thus, the wisdom teeth T4 are not accommodated in the cylindrical CT imaging area CAr2, and cannot be imaged.

In order to avoid this, the detection area may be made larger such that the CT imaging area is a cylindrical CT imaging area CAr1 having a diameter of about 100 mm. In this case, the wisdom teeth T4 are accommodated in the cylindrical CT imaging area CAr1, and can be imaged.

However, the detection plane of the X-ray detector is highly expensive. Enlargement of the detection plane increases the cost of the X-ray CT imaging device.

By contrast, in the case where the CT imaging area is the triangular CT imaging area CAb having a generally triangular shape as seen in a plan view which includes the imaging target OB3, the imaging target OB3 including the wisdom teeth T4 can be imaged without enlarging the detection plane 21a of the X-ray detector 21. An area represented with hatching which is inside the cylindrical CT imaging area CAr1 and outside the triangular CT imaging area CAb is not unnecessarily irradiated with the X-ray. Thus, the amount of exposure can be decreased.

The local CT imaging area CAa imaged above by the X-ray CT imaging device 1 includes one left posterior tooth T2A as the local imaging target OB1. FIG. 32 is a schematic plan view showing local X-ray CT imaging performed on the local imaging target OB1 having a different target area from that of the above-described local imaging target OB1. As shown in FIG. 32, X-ray CT imaging may be performed on, for example, a plurality of continuous posterior teeth T2 or anterior teeth T1 as the local imaging target OB1.

The local CT imaging area CAa is not limited to having a circular shape as seen in a plan view as shown in FIG. 32, and may have a shape in accordance with the shape of the local imaging target OB1, such as, for example, an elliptical shape as seen in a plan view.

In the above description, X-ray CT imaging is performed on the dental arch, which is a dental area, as the imaging target OB. Alternatively, X-ray CT imaging may be performed only on the temporomandibular joint as the imaging target OB. Still alternatively, X-ray CT imaging may be performed on a local site of hands and feet, the head and neck, and the like, as well as the dental area.

DESCRIPTION OF THE REFERENCE NUMERALS

1 . . . X-ray CT imaging device
10 . . . X-ray generation section
13 . . . Beam forming mechanism
14 . . . Height direction blocking plate
15 . . . Lateral direction blocking plate
16a . . . Blocking plate length direction moving mechanism
16b . . . Blocking plate lateral direction moving mechanism
18 . . . L-shaped blocking plate
20 . . . X-ray detection section
23 . . . Moving mechanism
30 . . . Revolving arm
31 . . . Revolution shaft
34 . . . Shaft moving mechanism
34a . . . Moving mechanism
37 . . . Revolution motor
41 . . . Upper frame
60 . . . Main body control section
BX . . . X-ray cone beam
BX1 . . . X-ray cone beam for a large radiation field CT
BX2 . . . X-ray cone beam for a small radiation field CT
CA . . . CT imaging area
CAa . . . Local CT imaging area
CAb . . . Triangular CT imaging area
M1 . . . Subject
T1 . . . Anterior tooth
T2 . . . Left posterior tooth
T3 . . . Right posterior tooth

What is claimed is:

1. An X-ray CT imaging device for performing X-ray CT imaging of a CT imaging area of a subject, the X-ray CT imaging device comprising:
an imaging mechanism including an X-ray generator that generates an X-ray, the X-ray generator being accommodated in a housing having an output opening for transmitting the X-ray, a beam formation mechanism that blocks and restricts a radiation range of the X-ray generated by the X-ray generator to form an X-ray cone beam to be directed to the CT imaging area, the beam formation mechanism being positioned forward to the output opening of the housing, and an X-ray detector that detects the X-ray cone beam directed to the subject;
a support that supports the X-ray generator and the X-ray detector in a state where the X-ray generator and the X-ray detector have the subject therebetween;
an imaging mechanism driving section that revolves the support at least about a revolution shaft; and
a controller that controls at least the X-ray generator, the beam formation mechanism, and the imaging mechanism driving section, wherein:
the revolution shaft forms a revolution center,
the X-ray generator and the X-ray detector are revolved around the revolution center with respect to the subject,
a direction parallel to a direction of an axis of the revolution shaft is a length direction,
a direction that is perpendicular to a direction from the X-ray generator to the X-ray detector and also perpendicular to the length direction is a lateral direction,
the beam formation mechanism comprises:
a plurality of length direction X-ray blocking plates that block and restrict the radiation range of the X-ray cone beam in the length direction with respect to the CT imaging area;
a plurality of lateral direction X-ray blocking plates that block and restrict the radiation range of the X-ray cone beam in the lateral direction with respect to the CT imaging area; and
blocking plate moving mechanisms that move the plurality of length direction X-ray blocking plates and the plurality of lateral direction X-ray blocking plates,
the revolution center is fixed in the CT imaging area,
the CT imaging area has a generally triangular shape as seen from the length direction,
during the X-ray CT imaging when the support is revolving, the controller controls blocking plates moving mechanisms so that the plurality of lateral direction X-ray blocking plates restrict the radiation range of the X-ray cone beam in the lateral direction so as to make an expansion of the X-ray cone beam in the lateral direction suitable to a width of the CT imaging area as seen in a radiation direction of the X-ray cone beam from the X-ray generator at a revolution position of the support,
the plurality of lateral direction X-ray blocking plates restrict the X-ray cone beam so that each of lateral sides of expansion of the X-ray cone beam fits to each of lateral edges of the CT imaging area while a position of each of the lateral edges to the revolution center changes in accordance with the revolution position,
a first distance from a reference line to a right edge of the lateral edges and a second distance from the reference line to a left edge of the lateral edges change independently in accordance with the revolution position, and
the reference line passes from the X-ray generator through the revolution center as seen from the length direction.

2. The X-ray CT imaging device according to claim 1, wherein
the controller controls a lateral direction adjusting section that is a blocking plate lateral direction moving mechanism that moves the plurality of lateral direction X-ray blocking plates.

3. The X-ray CT imaging device according to claim 2, wherein
the blocking plate lateral direction moving mechanism independently moves the plurality of lateral direction X-ray blocking plates in the lateral direction with respect to the CT imaging area.

4. The X-ray CT imaging device according to claim 1, wherein
the CT imaging area formed to have the generally triangular shape as seen from the length direction is set to accommodate anterior teeth and left and right posterior teeth of a dental arch.

5. The X-ray CT imaging device according to claim 1, wherein
in the generally triangular shape as seen from the length direction, at least one of three corners is formed of an arc convexed outward and thus is rounded.

6. The X-ray CT imaging device according to claim 1, wherein
in the generally triangular shape as seen from the length direction, at least one of three sides includes an arc convexed outward at a central part thereof.

7. The X-ray CT imaging device according to claim 1, wherein:
in the generally triangular shape as seen from the length direction, one of three sides has outward protrusions at both of two ends thereof, and an apex facing the one side and each of the protrusions are connected to each other by a curved line; and
the generally triangular shape is bilaterally symmetrical with respect to an axis of symmetry passing through the apex and the center of the one side.

8. The X-ray CT imaging device according to claim 1, wherein
the controller changes the radiation range restricted by the, beam formation mechanism such that a generally triangular imaging area X-ray CT imaging performed on the CT imaging area in the case where the CT imaging area has the generally triangular shape as seen from the length direction, or another-shaped imaging area X-ray CT imaging performed on the CT imaging area in the case where the CT imaging area has another shape, is selectable.

9. The X-ray CT imaging device according to claim 1, wherein
the beam formation mechanism further comprises:
a length direction adjusting section that, during the X-ray CT imaging when the support is revolving, adapts an expansion in the length direction of the X-ray cone beam, which is to be restricted by the plurality of length direction X-ray blocking plates, to a shape of the CT imaging area in accordance with the revolution position of the imaging mechanism driven by the imaging mechanism driving section, the length direction adjusting section being controllable by the controller, and
wherein the length direction adjusting section is a blocking plate length direction moving mechanism that moves the plurality of length direction X-ray blocking plates in the length direction.

10. The X-ray CT imaging device according to claim 9, wherein:
each blocking plate of the plurality of length direction X-ray blocking plates is independently movable in the length direction with respect to the CT imaging area; and
the blocking plate length direction moving mechanism is structured to move the plurality of length direction X-ray blocking plates.

11. The X-ray CT imaging device according to claim 9, wherein:
the controller is structured to control the expansion in the length direction of the X-ray cone beam to become larger when the CT imaging area approaches the X-ray generator and to become smaller when the CT imaging area is distanced from the X-ray generator.

12. The X-ray CT imaging device according to claim 1, comprising
an X-ray detector moving section that relatively moves the X-ray detector with respect to the support; and wherein:
the controller is structured to control the X-ray detector moving section in accordance with the radiation range of the X-ray cone beam.

13. The X-ray CT imaging device according to claim 1, wherein
the controller changes the radiation range restricted by the beam formation mechanism, such that first X-ray CT imaging or second X-ray CT imaging is selectable, wherein the first X-ray CT imaging is an imaging for first area of interest which is entirety of an area of interest of the subject, and the second X-ray CT imaging is an imaging for second area of interest which is a part of the first area of interest.

14. The X-ray CT imaging device according to claim 1, wherein
the controller controls a movement of the beam formation mechanism to output an X-ray slit beam formed by changing the radiation range restricted by the beam formation mechanism, and controls the imaging mechanism driving section to revolve the support, such that the output X-ray slit beam forms a locus for panorama X-ray imaging, and such that panorama X-ray imaging is performed by the X-ray slit beam.

* * * * *